United States Patent
Sherman et al.

(10) Patent No.: US 11,396,505 B2
(45) Date of Patent: Jul. 26, 2022

(54) INHIBITORS OF CAMKK2 AND USES OF SAME

(71) Applicant: New York University, New York, NY (US)

(72) Inventors: Dan Sherman, New York, NY (US); Timothy J. Cardozo, New York, NY (US)

(73) Assignee: New York University, New York, NY (US)

( * ) Notice: Subject to any disclaimer, the term of this patent is extended or adjusted under 35 U.S.C. 154(b) by 7 days.

(21) Appl. No.: 16/883,985

(22) Filed: May 26, 2020

(65) Prior Publication Data

US 2020/0369656 A1 Nov. 26, 2020

Related U.S. Application Data

(60) Provisional application No. 62/852,665, filed on May 24, 2019.

(51) Int. Cl.
| | | |
|---|---|---|
| *C07D 413/14* | (2006.01) |
| *C07D 403/14* | (2006.01) |
| *C07D 401/14* | (2006.01) |
| *C07D 417/14* | (2006.01) |
| *A61P 35/00* | (2006.01) |
| *C07D 471/04* | (2006.01) |
| *C07D 417/04* | (2006.01) |
| *C07D 413/04* | (2006.01) |

(52) U.S. Cl.
CPC ............ *C07D 413/14* (2013.01); *A61P 35/00* (2018.01); *C07D 401/14* (2013.01); *C07D 403/14* (2013.01); *C07D 413/04* (2013.01); *C07D 417/04* (2013.01); *C07D 471/04* (2013.01)

(58) Field of Classification Search
CPC .. C07D 401/14; C07D 403/14; C07D 413/14; C07D 417/14; A61P 35/00
See application file for complete search history.

(56) References Cited

U.S. PATENT DOCUMENTS

| | | | | |
|---|---|---|---|---|
| 2004/0127536 A1* | 7/2004 | Bhagwat | ................. | A61P 13/12 514/406 |
| 2014/0031360 A1* | 1/2014 | Wang | ................... | C07D 405/04 514/252.11 |

* cited by examiner

*Primary Examiner* — Samira J Jean-Louis
(74) *Attorney, Agent, or Firm* — Hodgson Russ LLP

(57) ABSTRACT

The present disclosure provides compounds suitable for inhibiting CaMKK2. Also provided are compositions and methods of treating diseases associated with CaMKK2.

9 Claims, 1 Drawing Sheet

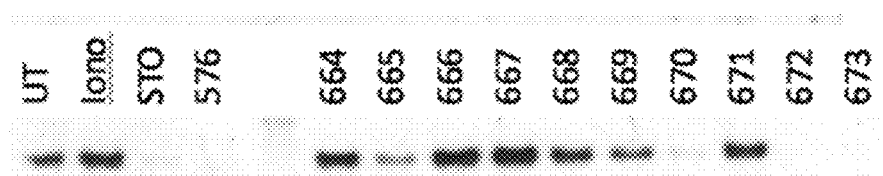

INHIBITORS OF CAMKK2 AND USES OF SAME

CROSS-REFERENCE TO RELATED APPLICATION

This application claims priority to U.S. Provisional Patent Application No. 62/852,665, filed May 24, 2019, the disclosure of which is incorporated herein.

STATEMENT REGARDING FEDERALLY SPONSORED RESEARCH

This invention was made with government support under contract no. AG008051 awarded by the National Institutes of Health. The government has certain rights in the invention.

FIELD OF THE DISCLOSURE

The disclosure generally relates to inhibitors of CaMKK2. More particularly, the disclosure relates to small molecule inhibitors of CaMKK2.

BACKGROUND OF THE DISCLOSURE $Ca^{2+}$ is the most pervasive second messenger in cell-based signaling and many proteins are involved in mediating calcium signaling. Of these, the $Ca^{2+}$/Calmodulin kinases (CaM kinases) have multiple roles many of which remain to be elucidated. The most upstream of these are the CaM-kinase kinases (CaMKKs) which consist of two known isoforms ($\alpha/\beta$ or 1/2). Both isoforms act as upstream activators of CaMK1 and CaMK4. Intriguingly, CaMKK2 has constituitive or autonomous activity, while CaMKK1 is dependent upon $Ca^{2+}$/CaM binding. The entire list of substrates of CaMKK2 is not yet known but, in addition to CaMK1 and CaMK4, this kinase has been shown to act as an upstream activator of Akt and AMPK.

Over the last decade there have been numerous studies implicating CaMKK2 in diseases. Recently CaMKK2 has been shown to play an important role in cancers, such as, for example, hepatocellular carcinoma, prostate cancer, glioma; in neurological diseases such as, for example, Alzheimer's Disease, depression and bipolar disorder; and in metabolic disorders, such as, for example, bone loss; diabetes, metabolic syndrome and obesity. In each of these cases, a high quality pharmacological probe would help elucidate the biology or potentially be a therapeutic agent.

The activity of CaMKK2 in neurodegenerative diseases is especially prominent in the literature, and suggests that a drug-like CaMKK2 inhibitor may be a therapeutic entity for treating these diseases. Accumulation of Aβ42 oligomers (42-amino acid-long amyloid beta [Aβ42o] peptide fibrils forming amyloid plaques), Tau phosphorylation (and ultimately accumulation of hyper-phosphorylated Tau in tangles [NFT]), increased/defective autophagy, abnormal calcium homeostasis and defective mitochondrial structure/function have all independently been implicated in the pathophysiology of Alzheimer's Disease (AD). Over-activation of the CAMKK2-AMPK kinase pathway represents a novel and unique unifying 'stress-response' pathway, since this kinase dyad is over-activated by Aβ42o in a calcium-dependent manner and triggers phosphorylation and activation of a myriad of downstream effectors such as Tau, MFF (mitochondria fission factor), and ULK2 (mitophagy inducing kinase) and, therefore, links at least 5 of the landmark defects reproducibly involved in early stages of AD pathophysiology. Before the formation of amyloid plaques and NFT, amyloidogenic processing of amyloid precursor protein (APP) by β- and γ-secretase produces abnormal accumulation of Aβ42 peptides, which have a strong ability to oligomerize and form dimers, trimers, and higher-order oligomers that ultimately fibrillate to form Aβ plaques. Soluble, oligomeric forms of Aβ42 (Aβ42o) lead to early loss of excitatory synapses (synaptotoxic effects) in cortical and hippocampal pyramidal neurons (PNs) before plaque formation and without compromising neuronal viability, strongly suggesting that synaptotoxicity is an early event in the disease progression triggered by soluble Aβ42o. A second class of pathological cellular events reported in brain of AD patients are thought to affect mitochondrial structure and function, including altered axonal mitochondria motility, defective mitochondrial function and imbalanced mitochondrial fission and fusion. Aβ42o overactivates the stress-response AMP-activated kinase (AMPK) in a CAMKK2-dependent manner and inhibition of CAMKK2 or AMPK protects hippocampal PNs from Aβ42-mediated loss of excitatory synapses observed in the hAPP$^{SWE,IND}$ transgenic AD mouse model (J20) in vivo. Importantly, the effects of Aβ42o-dependent CAMKK2-AMPK over-activation on synaptic loss require the ability of AMPK to phosphorylate Tau on a specific Serine residue (S262) providing the first link between Aβ42o and Tau phosphorylation in early stages of AD pathophysiology. In addition, upon AMPK-dependent phosphorylation, mitochondrial fission factor (MFF) enhances the recruitment of the mitochondrial fission effector Drp1, suggesting a connection to neuronal mitophagy (autophagy of mitochondria) and that blocking CAMKK2-AMPK blocks the ability of Aβ42o to induce synaptic loss. AMPK is ubiquitously expressed by all cells in the body, but CAMKK2 expression is largely restricted to neurons in the central nervous system and, thus, constitutes a drug target for AD. The CAMKK2-AMPK-phosphoTau pathway is, thus, the only pathway known that links Aβ to tau phosphorylation, suggesting that this unique pathway is not just a surrogate of Aβ but an actual pathophysiological mechanism of AD development and maintenance. This effect may apply to other neurodegenerative diseases, as CAMKK2 overactivation appears also to be associated with prion disease maintenance.

The most well-known inhibitor of CaMKK2 is STO-609. This agent, while reasonably potent biochemically, has poor potency in cells. For example, it was previously used at 100 to 1000-fold over it is known $IC_{50}$ to observe effects in cells. The selectivity of this agent over other kinases is poor and, at such high concentrations as have been used in cells in published studies, other targets are being engaged, confounding interpretation to some extent. It has therefore been acknowledged in the extant literature that a dose of caution should be employed when interpreting the results of experiments with this agent, due to its poor selectivity. Furthermore, STO-609 has poor permeability. These issues may disqualify STO-609 from use in vivo evaluation.

As of yet, no licensed drug specifically targets CAMKK2, and an in vivo CAMKK2 chemical probe (a selective, pharmacokinetically suitable agent that can be used in animal studies to draw conclusions about in vivo phenotype of CAMKK2 inhibition) does not currently exist, yet such a probe is required for preclinical studies. As a serine/threonine kinase, CAMKK2 falls within the druggable genome: over 25 kinase inhibitors targeting a variety of kinases already are FDA-approved drugs, many of which have revolutionized the treatment of multiple diseases. In a published PK study, STO-609 fails to enter the brain despite achieving plasma concentrations >30 μM with a 9.4 mg/kg ip dose. In fact, this agent displayed generally poor tissue penetration with $C_{max}$ values at or below 1 μM with elimination completed in 8 hour (h) or less. This is well below the putative cell-based $IC_{50}$ of this agent. The effects of plasma protein binding were not considered but would undoubtedly render these concentrations insufficient to deliver efficacious free concentrations of this agent. The poor permeability of STO-609 is in large part due to the carboxylate moiety which is required for CaMKK2 potency. A previously published paper on the Phase I clinical trial of the TORC1/2 inhibitor OSI-027 which, like STO-609, has a pendent free carboxylate moiety, demonstrated poor tissue and tumor penetration despite achieving high plasma concentrations. Although drugs with carboxylic acids are known, they are not common and are generally considered a liability for entry into the central nervous system (CNS). STO-609 is also a potent agonist of the ArH receptor (43 nM) leading to the induction of CYP1A1, 1B1 and other ArH target genes in multiple cell lines. It was demonstrated that STO-609 also activates CaMK1 through ArH activity—an especially confounding observation as CaMK1 is a substrate of CaMKK2 and should be indirectly inhibited. Taken together, these data rules out STO-609 for CNS applications. A CaMKK2 inhibitor was previously disclosed by scientists at the University of North Carolina; however, this agent, like STO-609, also has a carboxylate on which its potency depends. It observed that it has even poorer cell-based activity that STO-609. In short, while CaMKK2 is an important target, no suitable in vivo probe exists for this target in AD, and other diseases/pathologies associated with CaMKK2.

Based on the foregoing, there exists an ongoing and unmet need for improved CaMKK2 inhibitors.

SUMMARY OF THE DISCLOSURE

The present disclosure provides compounds suitable for inhibiting CaMKK2. Also provided are compositions and methods of treating diseases associated with CaMKK2.

In an aspect, the present disclosure provides compounds. The compounds may be inhibitors of CaMKK2. The compounds comprise an indazole core. The indazole core is substituted at the 3-position and the 5-position. The indazole core may have additional substitution as described herein.

In an aspect, the present disclosure provides compositions comprising one or more compound of the present disclosure. The compositions may comprise one or more pharmaceutically acceptable carrier.

In an aspect, the present disclosure provides methods of using one or more compounds of the present disclosure. For example, the compounds can be used to treat an individual having cancer, a neurologic disease, a metabolic condition, an orthopedic condition, a mental health condition, a viral infection, or a combination thereof.

For example, a method of treating comprises administering to an individual one or more compound of the present disclosure or a composition comprising one or more compounds of the present disclosure.

The method may be carried out in an individual who has been diagnosed with or is suspected of having cancer (e.g., prostate cancer, ovarian cancer, pymphoma, lung, colorectal, glioma, hepatocellular, and the like, and combinations thereof), neurologic diseases (e.g., neurodegenerative diseases such as, for example, Alzheimer's Disease and the like), metabolic conditions (e.g., obesity, type-2 diabetes, non-alcoholic fatty liver disease (NAFLD), and the like, and combinations thereof), orthopedic conditions (e.g., for treating fractures, for treating muscle atrophy, and the like, and combinations thereof), mental health conditions (e.g., anxiety, depression, obsessive compulsive disorder, bipolar disorder, schizophrenia, and the like, and combinations thereof), a viral infection (i.e., therapeutic use) (e.g., human immunodeficiency virus (HIV), tuberculosis (TB), and the like, and combinations), or a combination thereof.

A method of the present disclosure comprises administering to an individual in need of treatment one or more compounds or a composition comprising one or more compounds of the present disclosure. Compositions comprising the compounds described herein may be administered to an individual using any known method and route, including oral, parenteral, subcutaneous, intraperitoneal, intrapulmonary, intranasal, and intracranial injections. Parenteral infusions include, but are not limited to, intramuscular, intravenous, intraarterial, intraperitoneal, subcutaneous administration, and the like. Administration may also include, but is not limited to, topical and/or transdermal administrations.

BRIEF DESCRIPTION OF THE FIGURES

For a fuller understanding of the nature and objects of the disclosure, reference should be made to the following detailed description taken in conjunction with the accompanying FIGURES.

FIG. 1 shows an image of a western blot of Hela cells stimulated with ionomycin (Iono) and treated with vehicle (UT; untreated) or the indicated compounds (STO=STO-609; other compound numbers omit the "CL-" designation, so 576=CL=576. Bands indicate reactivity with anti-phospho-AMPK, which is a target of CaMKK2: disappearance of band is indicative of CaMKK2 inhibiton.

DETAILED DESCRIPTION OF THE DISCLOSURE

Although claimed subject matter will be described in terms of certain embodiments, other embodiments, including embodiments that do not provide all of the benefits and features set forth herein, are also within the scope of this disclosure. Various structural, logical, and method step changes may be made without departing from the scope of the disclosure.

Ranges of values are disclosed herein. The ranges set out a lower limit value and an upper limit value. Unless otherwise stated, the ranges include all values to the magnitude of the smallest value (either lower limit value or upper limit value) and ranges between the values of the stated range.

The present disclosure provides compounds suitable for inhibiting CaMKK2. Also provided are methods of treating diseases associated with CaMKK2.

As used herein, unless otherwise stated, the term "group" refers to a chemical entity that is monovalent (i.e., has one terminus that can be covalently bonded to other chemical species), divalent, or polyvalent (i.e., has two or more termini that can be covalently bonded to other chemical species). The term "group" includes radicalts (e.g., monovalent and multivalent, such as, for example, divalent radicals, trivalent radicals, and the like). Illustrative examples of groups include:

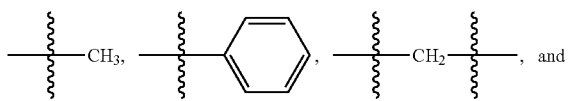

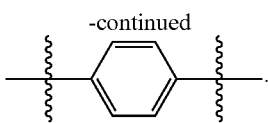

As used herein, unless otherwise indicated, the term "alkyl group" refers to branched or unbranched saturated hydrocarbon groups. Examples of alkyl groups include, but are not limited to, methyl groups, ethyl groups, propyl groups, butyl groups, isopropyl groups, tert-butyl groups, and the like. For example, the alkyl group is $C_1$ to $C_{12}$, including all integer numbers of carbons and ranges of numbers of carbons therebetween (e.g., $C_1$, $C_2$, $C_3$, $C_4$, $C_5$, $C_6$, $C_7$, $C_8$, $C_9$, $C_{10}$, $C_{11}$, and $C_{12}$,). The alkyl group may be unsubstituted or substituted with one or more substituent. Examples of substituents include, but are not limited to, various substituents such as, for example, halogens (—F, —Cl, —Br, and —I), aliphatic groups (e.g., alkyl groups, alkenyl groups, alkynyl groups, and the like), aryl groups, alkoxide groups, carboxylate groups, carboxylic acids, ether groups, amine groups, alcohol groups, alkyne groups (e.g., acetylenyl groups and the like), and the like, and combinations thereof.

As used herein, unless otherwise indicated, the term "aryl group" refers to $C_5$ to $C_{14}$ aromatic or partially aromatic carbocyclic groups, including all integer numbers of carbons and ranges of numbers of carbons therebetween (e.g., $C_5$, $C_6$, $C_7$, $C_8$, $C_9$, $C_{10}$, $C_{11}$, $C_{12}$, $C_{13}$, and $C_{14}$). An aryl group may also be referred to as an aromatic group. The aryl groups may comprise polyaryl groups such as, for example, fused ring, biaryl groups, or a combination thereof. The aryl group may be unsubstituted or substituted with one or more substituent. Examples of substituents include, but are not limited to, substituents such as, for example, halogens (—F, —Cl, —Br, and —I), aliphatic groups (e.g., alkyl groups, alkenyl groups, alkynyl groups, and the like), aryl groups, alkoxides, carboxylates, carboxylic acids, ether groups, and the like, and combinations thereof. Aryl groups may contain heteroatoms, such as, for example, nitrogen (e.g., pyridinyl groups and the like). Examples of aryl groups include, but are not limited to, phenyl groups, biaryl groups (e.g., biphenyl groups and the like), fused ring groups (e.g., naphthyl groups and the like), hydroxybenzyl groups, tolyl groups, xylyl groups, furanyl groups, benzofuranyl groups, indolyl groups, imidazolyl groups, benzimidazolyl groups, pyridinyl groups, and the like.

As used herein, unless otherwise indicated, the term "heteroaryl" refers to a $C_1$ to $C_{14}$ monocyclic, polycyclic, or bicyclic ring groups (e.g., aryl groups) comprising one or two aromatic rings containing at least one heteroatom (e.g., nitrogen, oxygen, sulfur, and the like) in the aromatic ring(s), including all integer numbers of carbons and ranges of numbers of carbons therebetween (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, and $C_{14}$). The heteroaryl groups can be substituted or unsubstituted. Examples of heteroaromatic groups include, but are not limited to, benzofuranyl groups, thienyl groups, furyl groups, pyridyl groups, pyrimidyl groups, oxazolyl groups, quinolyl groups, thiophenyl groups, isoquinolyl groups, indolyl groups, triazinyl groups, triazolyl groups, isothiazolyl groups, isoxazolyl groups, imidazolyl groups, benzothiazolyl groups, pyrazinyl groups, pyrimidinyl groups, thiazolyl groups, and thiadiazolyl groups, and the like. Examples of substituents include, but are not limited to, substituents such as, for example, halogens (—F, —Cl, —Br, and —I), aliphatic groups (e.g., alkyl groups, alkenyl groups, alkynyl groups, and the like), aryl groups, alkoxide groups, amine groups, carboxylate groups, carboxylic acids, ether groups, alcohol groups, alkyne groups (e.g., acetylenyl groups and the like), and the like, and combinations thereof.

In an aspect, the present disclosure provides compounds. The compounds may be inhibitors of CaMKK2. The compounds comprise an indazole core. The indazole core is substituted at the 3-position and the 5-position. The indazole core may have additional substitution as described herein.

In various other examples, compounds of the present disclosure has the following structure:

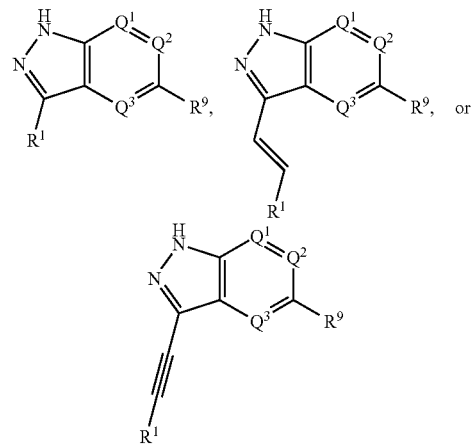

where $R^9$ is

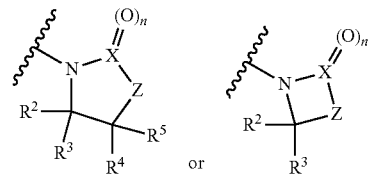

where $R^1$ is chosen from halogens (e.g., F, Cl, Br, and I), substituted (as described herein) or unsubstituted aliphatic groups (e.g., —$CH_3$, —$CF_3$, —$CH_2CH_3$, —$CH_2CF_3$, —CH=$CH_2$, —CH=$CHR^6$, n-propyl, i-propyl, ethynyl, —$CCR^6$, and the like), substituted or unsubstituted benzyl groups, substituted or unsubstituted cycloalkyl groups (e.g., $C_3$ to $C_7$ cycloalkyl groups, including $C_1$, $C_2$, $C_3$, $C_4$, $C_5$, $C_6$, and $C_7$), substituted or unsubstituted heterocycloalkyl groups (e.g., a 3 to 7 member ring containing at least 1 heteroatom, such as, for example, oxygen, nitrogen, and the like, including a 3-membered ring containing at least 1 heteroatom, a 4-membered ring containing at least 1 heteroatom, a 5-membered ring containing at least 1 heteroatom, a 6-membered ring containing at least 1 heteroatom, and a 7-membered ring containing at least 1 heteroatom), substituted or unsubstituted aryl groups (e.g., phenyl, naphthyl, substituted derivatives thereof, and the like), substituted or unsubstituted heteroaryl groups (e.g., pyridinyl, indolyl, benzofuranyl, benzothiophenyl, quinolinyl, isoquinolinyl, quinoxylinyl, imidazopyridinyl, pyrrolyl, pyrazolyl, oxazolyl, imidazolyl, and substituted (e.g., substituted as described herein) derivatives thereof, and the like), —$COR^6$, —$CO_2R^7$, —$CONHR^7$, $CONR^7R^8$, and —$NHR^6$. $Q^1$, $Q^2$, and $Q^3$ are independently chosen from C—H, C—F, or N. $R^2$, $R^3$, $R^4$, and $R^5$ are independently chosen from hydrogen, substituted or unsubstituted aliphatic groups, benzyl groups, —OR$^6$ groups, and the like, and combinations thereof. Examples of R$^2$, R$^3$, R$^4$, and R$^5$ groups include, but are not limited to, —CH$_3$, —CH$_2$CH$_3$, benzyl, i-isopropyl, —CH$_2$OH, —CH$_2$NH$_2$, —CH$_2$NHR$^6$, —CH$_2$NR$^6$R$^7$, —CH$_2$CONH$_2$, —CH$_2$CONHMe, —OR$^6$, —(CH$_2$)$_x$OR$^6$ (where x=1-5, including 1, 2, 3, 4, and 5), —CH$_2$CH$_2$CH$_3$, —CH$_2$CH$_2$OH, —CH$_2$CH$_2$NH$_2$, —CH$_2$CH$_2$NHR$^6$, —CH$_2$CH$_2$R$^6$R$^7$, —CH$_2$CH$_2$CONH$_2$, and —CH$_2$CH$_2$CONHMe, and the like, and combinations thereof. R$^6$ is chosen from hydrogen, OH, substituted or unsubstituted alkyl groups, substituted or unsubstituted cycloalkyl groups, substituted or unsubstituted aryl groups (e.g., phenyl), substituted or unsubstituted heteroaryl groups (e.g., 2-pyridyl, 3-pyridyl, 4-pyridyl, pyrimidin-2-yl, pyrimidin-4-yl, pyrimidin-5-yl, pyrazol-3-yl, and pyrazol-4-yl, and the like, and combinations thereof), where each (except hydrogen) is optionally substituted with one or more R$^7$ group. R$^7$ and R$^8$ are independently chosen from substituted or unsubstituted alkyl groups (e.g., C$_1$ to C$_5$ alkyl groups, including C$_1$, C$_2$, C$_3$, C$_4$, and C$_5$), hydroxyl groups, substituted or unsubstituted alkoxy groups (e.g., C$_1$ to C$_4$ alkoxy groups, including C$_1$, C$_2$, C$_3$, and C$_4$), arylalkyl groups (e.g., (CH$_2$)$_n$-Ph where n=1-3, including 1, 2, and 3), substituted or unsubstituted heteroaryl groups (e.g., pyridinyl, indolyl, benzofuranyl, benzothiophenyl, quinolinyl, isoquinolinyl, quinoxylinyl, imidazopyridinyl, pyrrolyl, pyrazolyl, oxazolyl, imidazolyl, thiazolyl, and substituted (e.g., substituted as described herein) derivatives thereof, and the like, where each heteroaryl group is attached by a C—C, an O—C or an N—C bond), substituted or unsubstituted heterocyclyl groups (e.g., a 3 to 7 member ring containing at least 1 heteroatom, such as, for example, oxygen and/or nitrogen, including a 3-membered ring containing at least 1 heteroatom, a 4-membered ring containing at least 1 heteroatom, a 5-membered ring containing at least 1 heteroatom, a 6-membered ring containing at least 1 heteroatom, and a 7-membered ring containing at least 1 heteroatom), and heterocycloalkyoxy groups. Furthermore, for CONR$^7$R$^8$, R$^7$ and R$^8$ may attached to form a 3, 4, 5, 6 or 7 member ring. When X is carbon, then n is 1, Z is O, NH, CH$_2$, or NCH$_3$, or Z is a two-atom bridging moiety (e.g., —OCH$_2$—, —CH$_2$CH$_2$—, and the like) such that a 6-membered ring is formed (e.g.,

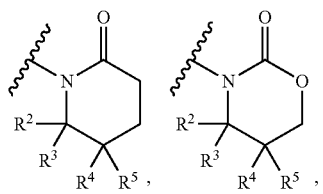

and the like), or when X is sulfur, then n is 2, and Z is CH$_2$, NH, NCH$_3$, or O.

In various examples, compounds of the present disclosure have the following structure:

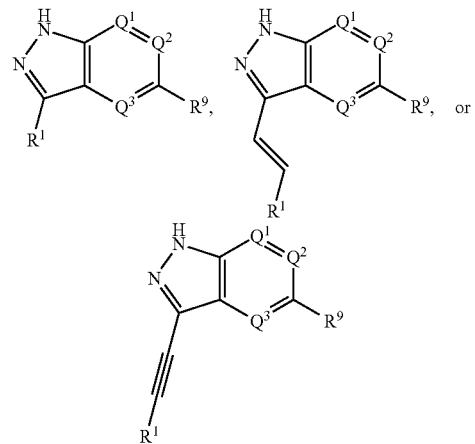

where R$^9$ is

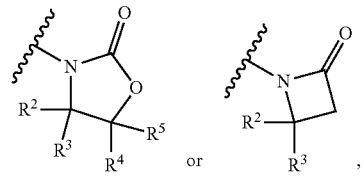

where R$^1$ is chosen from halogens (e.g., F, C$_1$, Br, and I), substituted or unsubstituted aliphatic groups aliphatic groups (e.g., —CH$_3$, —CF$_3$, —CH$_2$CH$_3$, —CH$_2$CF$_3$, —CH═CH$_2$, —CH═CHR$^6$, n-propyl, i-propyl, ethynyl, —CCR$^6$, and the like), substituted or unsubstituted benzyl groups, substituted or unsubstituted cycloalkyl groups (e.g., C$_3$ to C$_7$ cycloalkyl groups, including C$_1$, C$_2$, C$_3$, C$_4$, C$_5$, C$_6$, and C$_7$), heterocycloalkyl groups (e.g., a 3 to 7 member ring containing at least 1 heteroatom, such as, for example, oxygen, nitrogen, and the like, including a 3-membered ring containing at least 1 heteroatom, a 4-membered ring containing at least 1 heteroatom, a 5-membered ring containing at least 1 heteroatom, a 6-membered ring containing at least 1 heteroatom, and a 7-membered ring containing at least 1 heteroatom), a substituted or unsubstituted aryl group (e.g., phenyl, naphthyl, substituted derivatives thereof, and the like), substituted or unsubstituted heteroaryl groups (e.g., pyridinyl, indolyl, benzofuranyl, benzothiophenyl, quinolinyl, isoquinolinyl, quinoxylinyl, imidazopyridinyl, pyrrolyl, pyrazolyl, oxazolyl, imidazolyl, and substituted (e.g., substituted as described herein) derivatives thereof, and the like), —COR$^6$, CO$_2$R$^7$, —CONHR$^7$, CONR$^7$R$^8$, and —NHR$^6$. Q$^1$, Q$^2$, and Q$^3$ are independently chosen from C—H, C—F, or N. R$^2$, R$^3$, R$^4$, and R$^5$ are independently chosen from hydrogen, substituted or unsubstituted aliphatic groups, substituted or unsubstituted benzyl groups, —OR$^6$ groups, and the like, and combinations thereof. Examples of R$^2$, R$^3$, R$^4$, and R$^5$ groups include, but are not limited to, —CH$_3$, —CH$_2$CH$_3$, benzyl, i-isopropyl, —CH$_2$OH, —CH$_2$NH$_2$, —CH$_2$NHR$^6$, —CH$_2$NR$^6$R$^7$, —CH$_2$CONH$_2$, —CH$_2$CONHMe, —OR$^6$, —(CH$_2$)$_x$OR$^6$ (where x=1-5, including 1, 2, 3, 4, and 5), —CH$_2$CH$_2$CH$_3$, —CH$_2$CH$_2$OH, —CH$_2$CH$_2$NH$_2$, —CH$_2$CH$_2$NHR$^6$, —CH$_2$CH$_2$R$^6$R$^7$, —CH$_2$CH$_2$CONH$_2$, and —CH$_2$CH$_2$CONHMe, and the like, and combinations thereof. R$^6$ is chosen from hydrogen, OH, substituted or unsubstituted alkyl groups, substituted or unsubstituted cycloalkyl groups, substituted or aryl groups (e.g., phenyl), substituted or unsubstituted heteroaryl groups (e.g., 2-pyridyl, 3-pyridyl, 4-pyridyl, pyrimidin-2-yl, pyrimidin-4-yl, pyrimidin-5-yl, pyrazol-3-yl, and pyrazol-4-yl, and the like, and combinations thereof), where each (except hydrogen) is optionally substituted with one or more $R^7$ group. $R^7$ and $R^8$ are independently chosen from substituted or unsubstituted alkyl groups (e.g., $C_1$ to $C_5$ alkyl groups, including $C_1$, $C_2$, $C_3$, $C_4$, and $C_5$), hydroxyl groups, substituted or unsubstituted alkoxy groups (e.g., $C_1$ to $C_4$ alkoxy groups, including $C_1$, $C_2$, $C_3$, and $C_4$), arylalkyl groups (e.g., $(CH_2)_n$-Ph where n=1-3, including 1, 2, and 3), substituted or unsubstituted heteroaryl groups (e.g., pyridinyl, indolyl, benzofuranyl, benzothiophenyl, quinolinyl, isoquinolinyl, quinoxylinyl, imidazopyridinyl, pyrrolyl, pyrazolyl, oxazolyl, imidazolyl, thiazolyl, and substituted (e.g., substituted as described herein) derivatives thereof, and the like, where each heteroaryl group is attached by a C—C, an O—C or an N—C bond), substituted or unsubstituted heterocyclyl groups (e.g., a 3 to 7 member ring containing at least 1 heteroatom, such as, for example, oxygen and/or nitrogen, including a 3-membered ring containing at least 1 heteroatom, a 4-membered ring containing at least 1 heteroatom, a 5-membered ring containing at least 1 heteroatom, a 6-membered ring containing at least 1 heteroatom, and a 7-membered ring containing at least 1 heteroatom), and substituted or unsubstituted heterocycloalkyoxy groups. Furthermore, for $CONR^7R^8$, $R^7$ and $R^8$ may attached to form a 3, 4, 5, 6 or 7 member ring.

In an example, aryl and heteroaryl $R^1$ and $R^6$ substituents optionally have 1 or more substituents on a carbon atom of the substituent, such as, for example, halogens or solubilizing groups (e.g., an alkoxy group, a heterocycloalkoxy group, a pyrrolidino group, a morpholino group, a piperazino group, and the like). Non-limiting examples of these $R^1$ and $R^6$ substituents include:

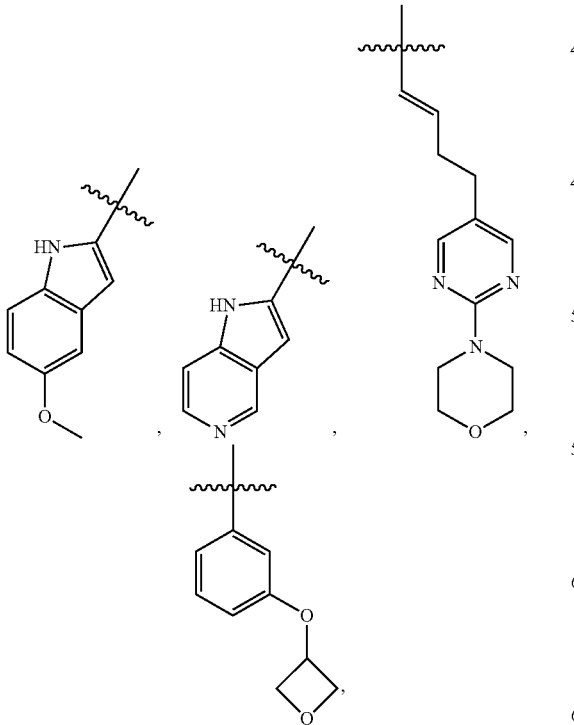

and the like. Additional non-limiting examples of substitutents are in tables 3, 4, and 5.

In various examples, an indazole core of a compound has the following structure:

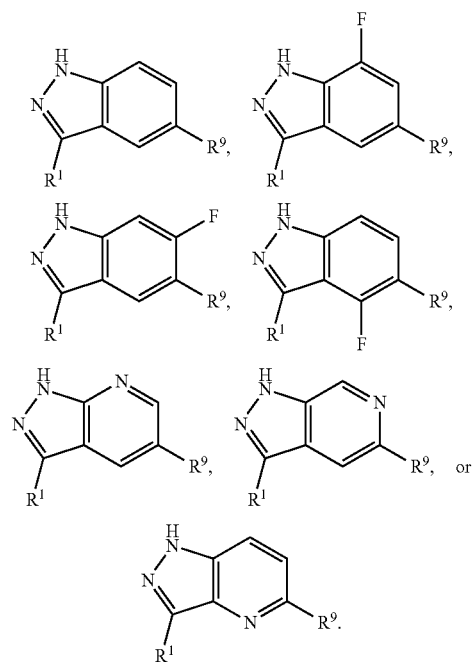

The structures may appear as follows:

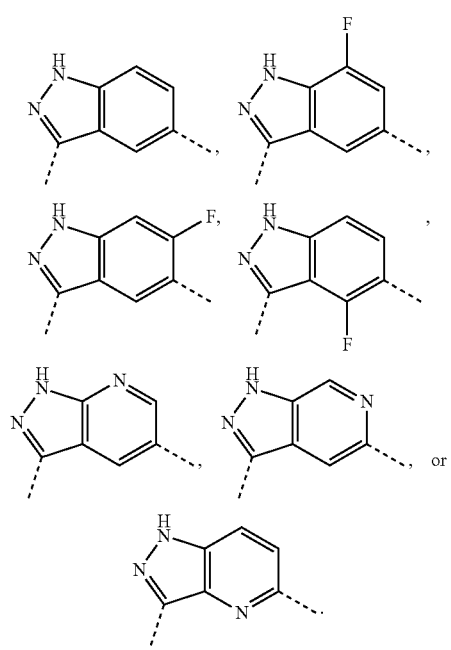

The dashed-dotted lines represent substitution at the 3-position and the 5-position.

In various examples, substituents at the 3-position, which may be $R^1$ groups, have the following structure:

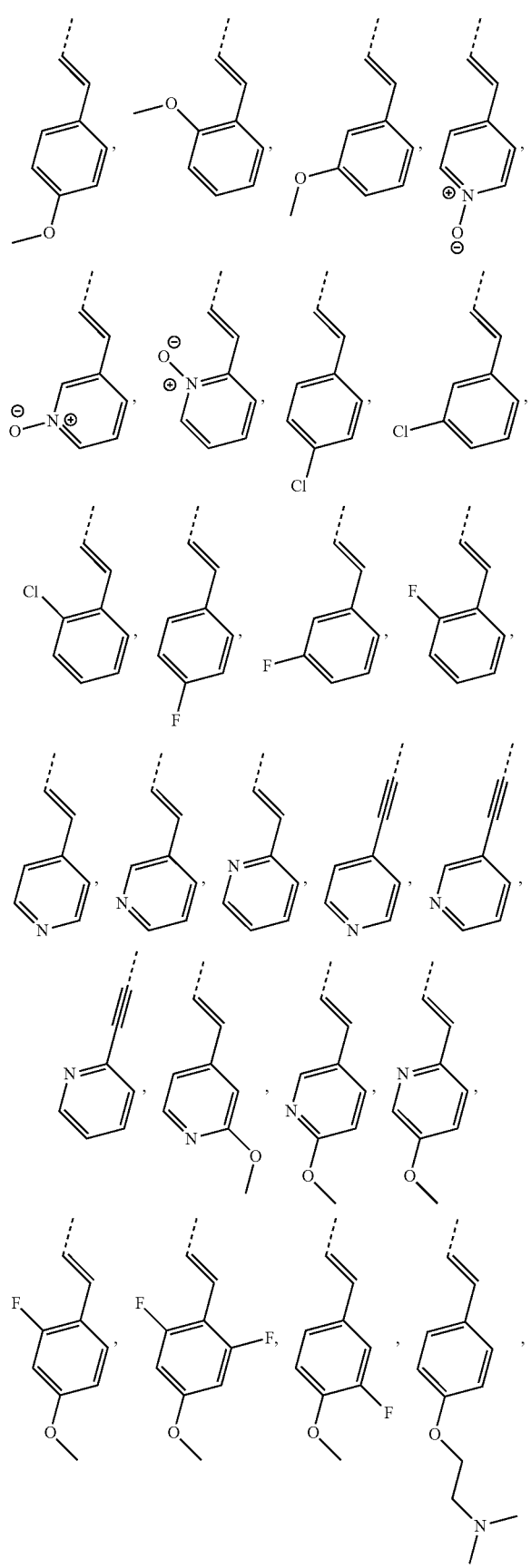
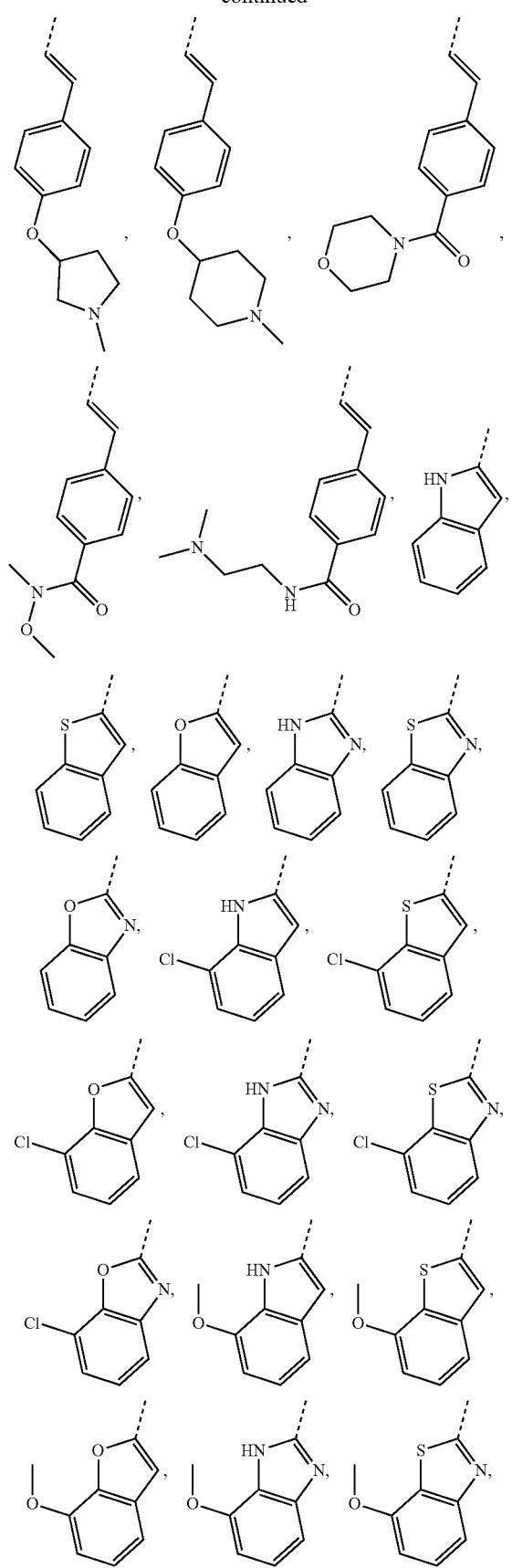

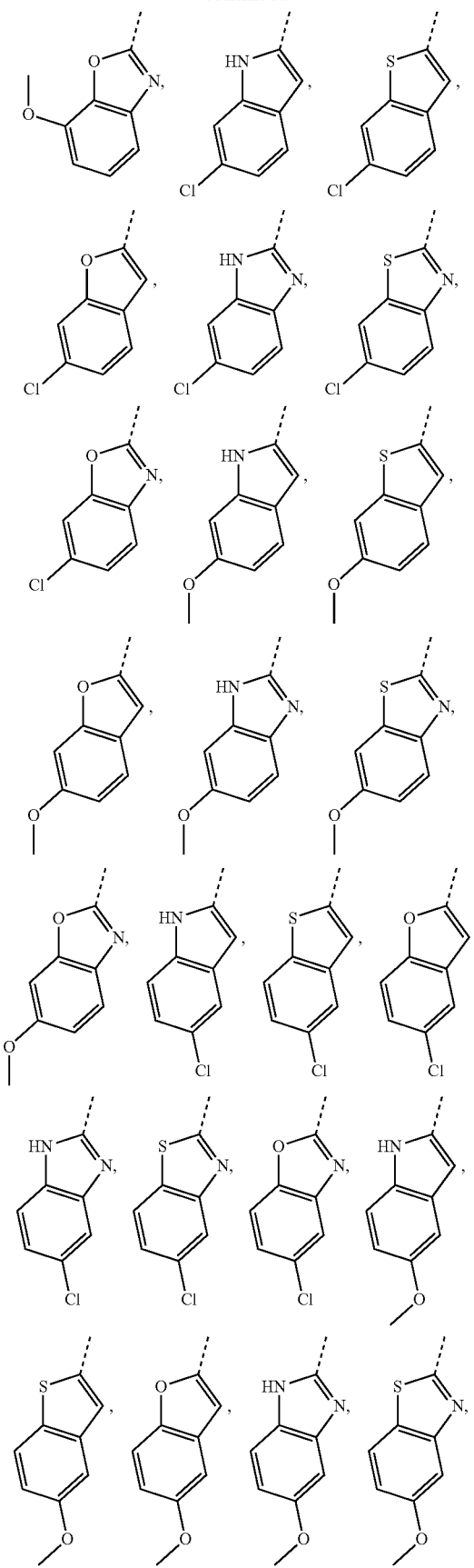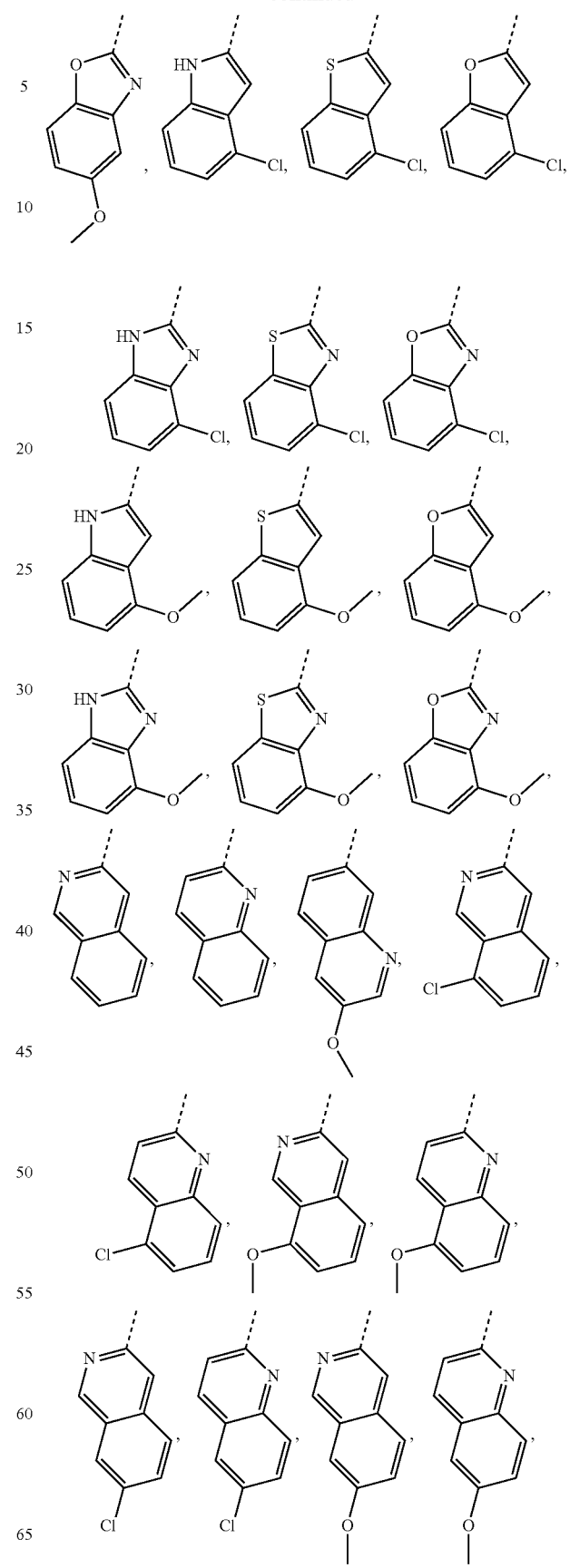

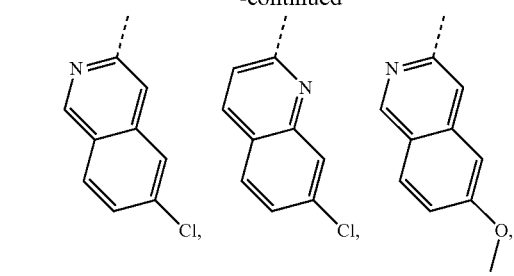
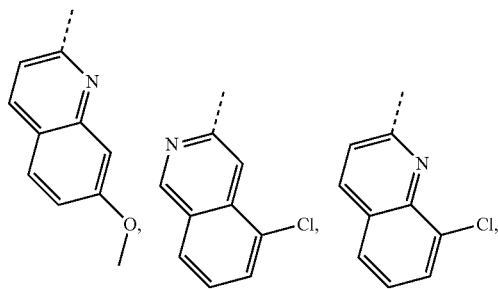
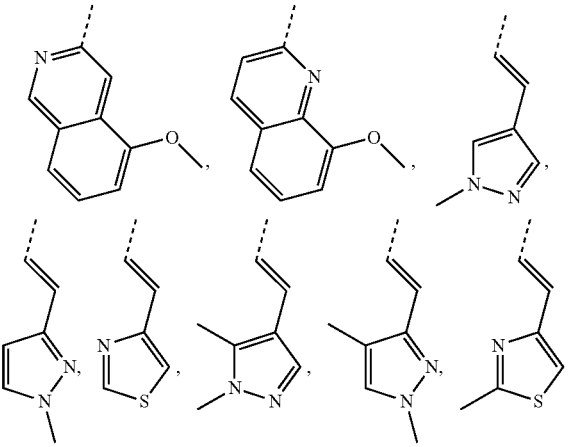
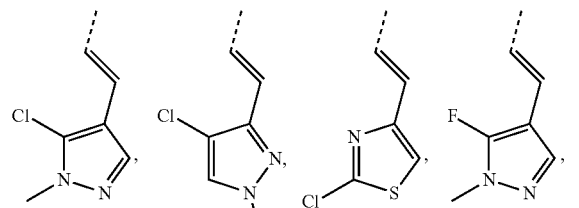
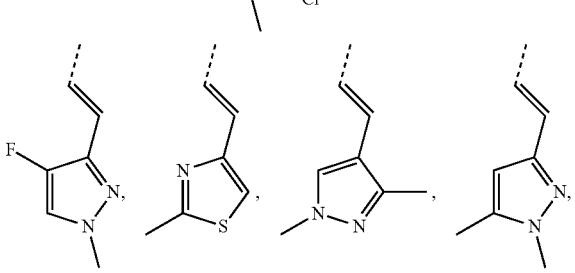
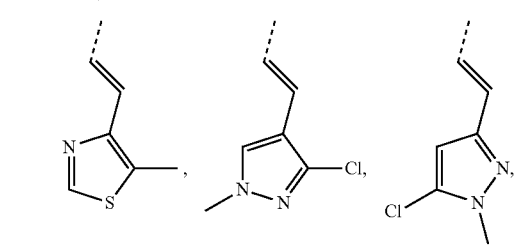
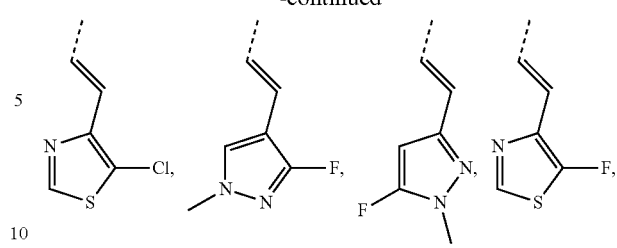
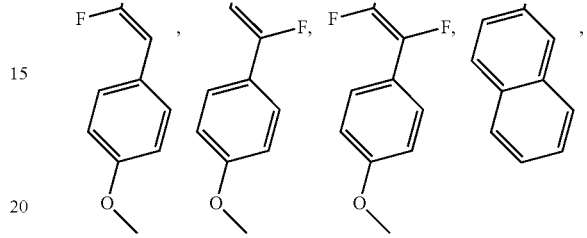
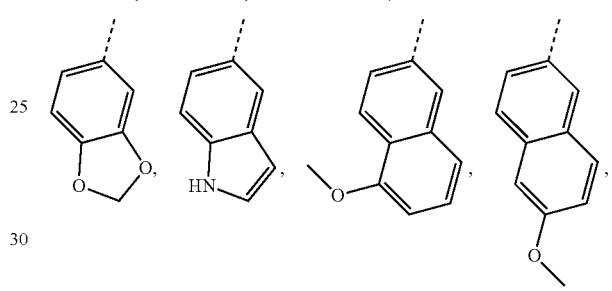
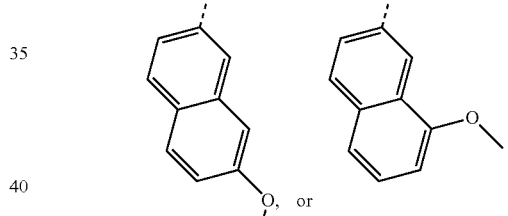
The dotted-dashed line is where the substituent connects to the 3-position of the indazole core.
In various examples, substituents at the 5-position, which may be $R^9$ groups, have the following structure:
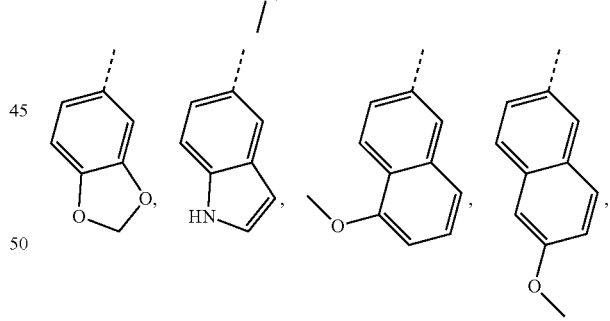
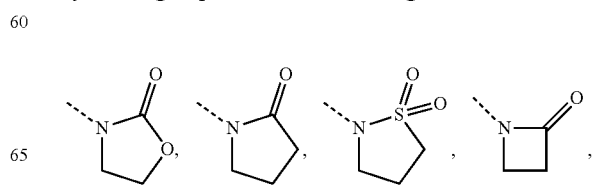

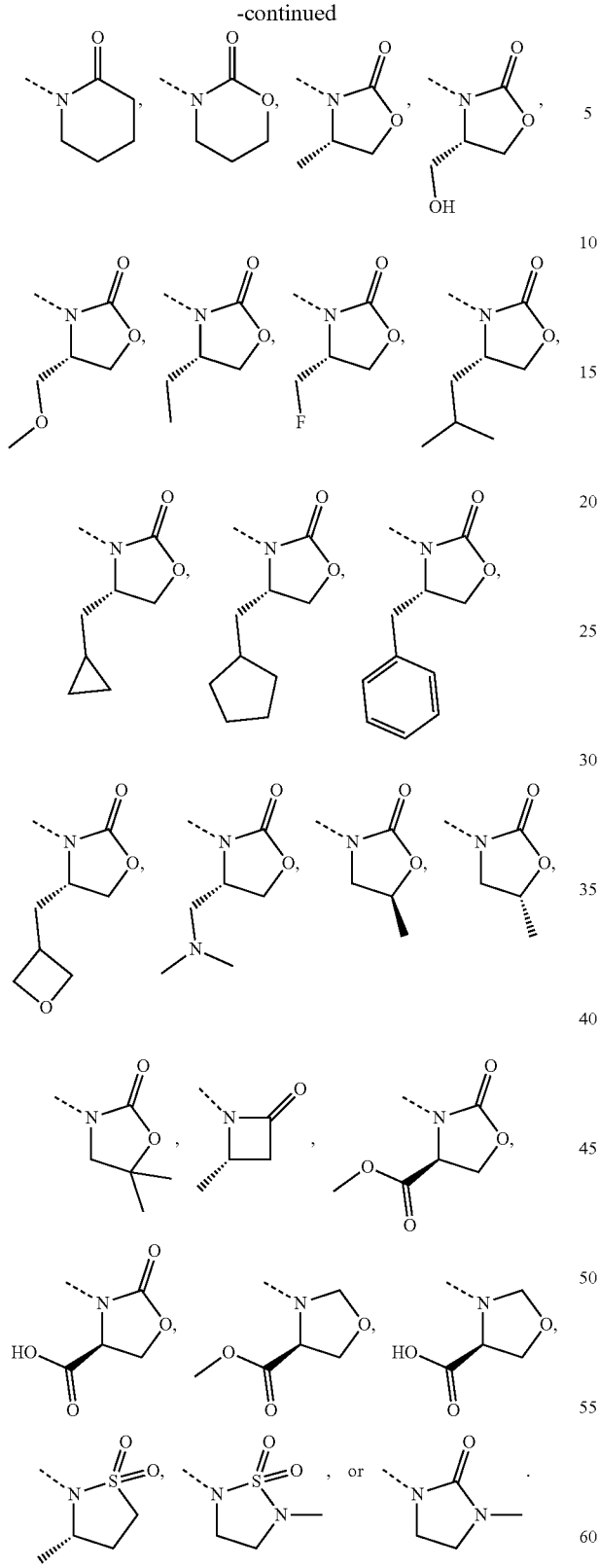
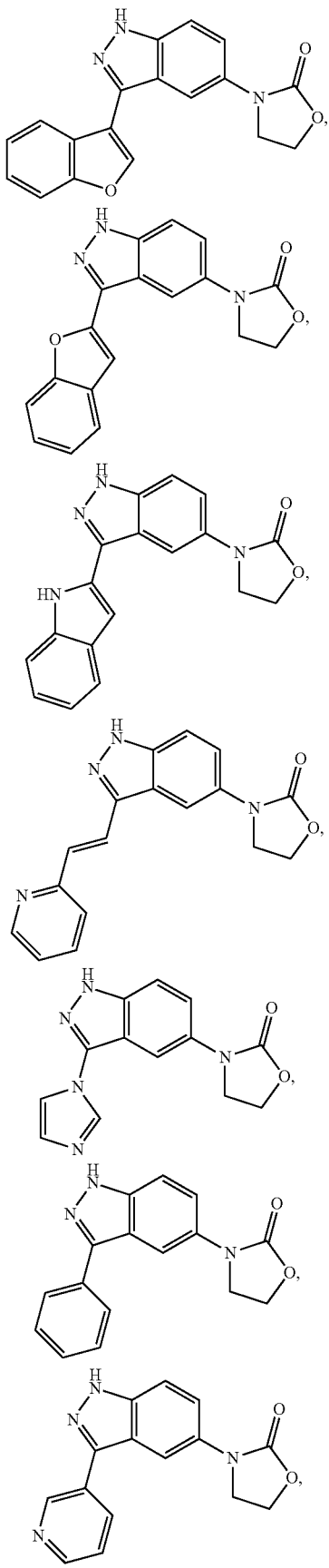
The dotted-dashed line is where the substituent connects to the 5-position of the indazole core.
A compound of the present disclosure may have the following structure:

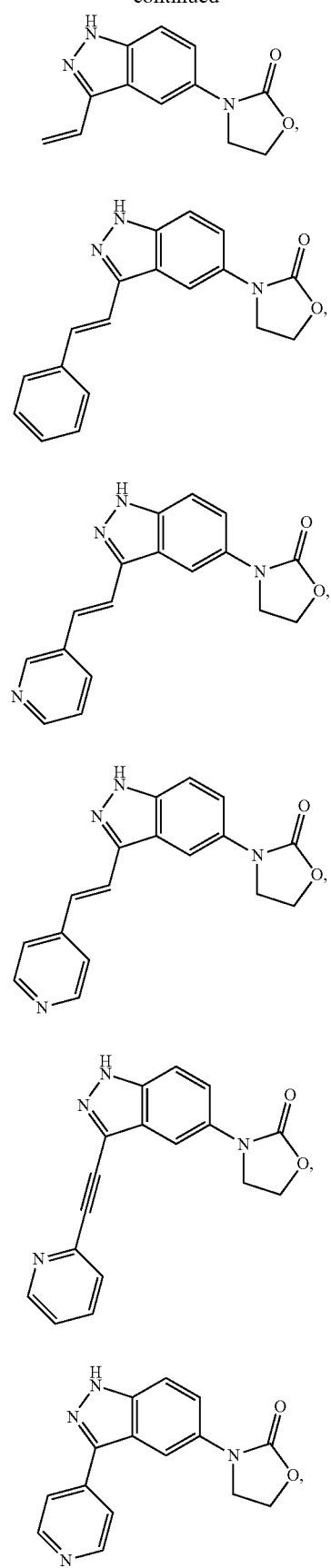
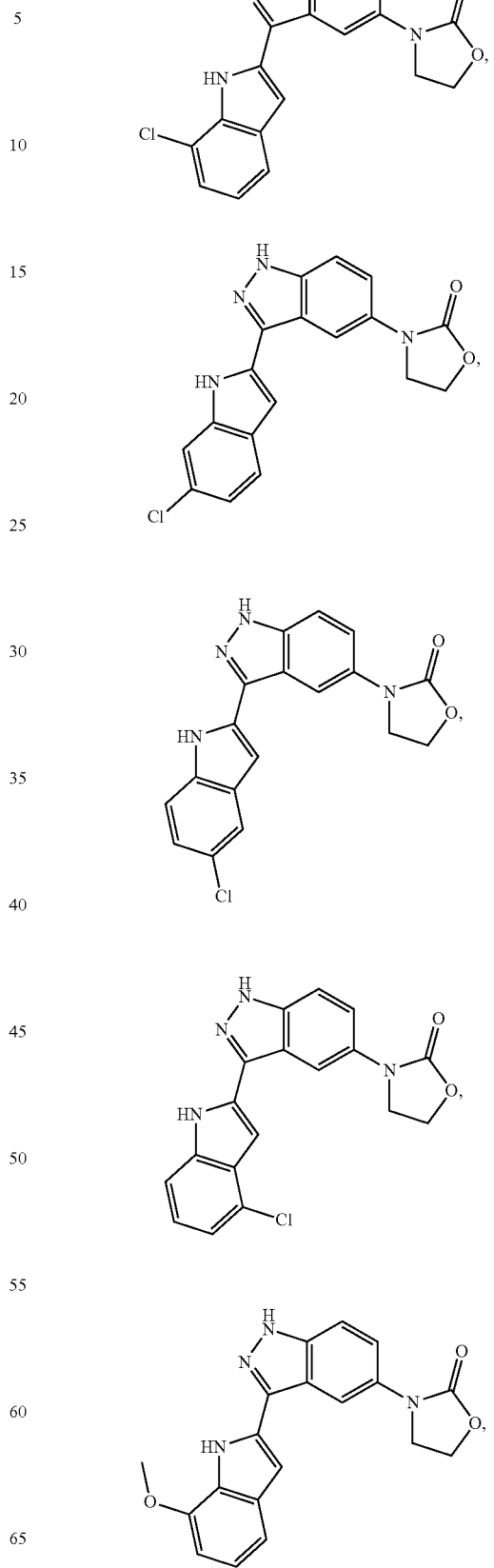

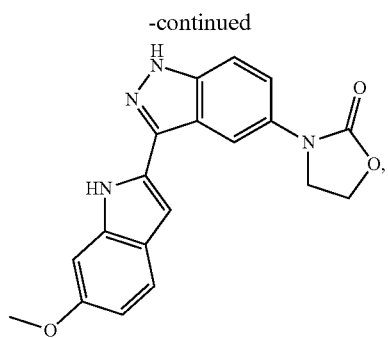
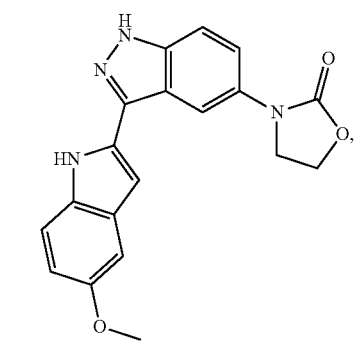
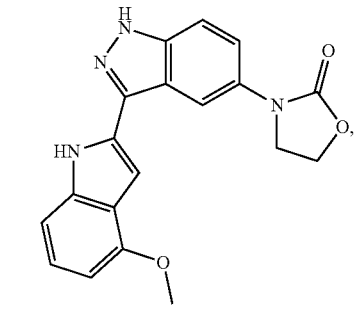
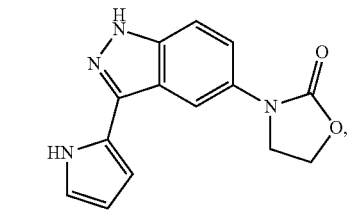
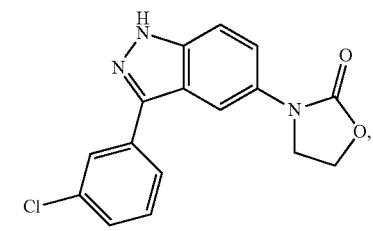
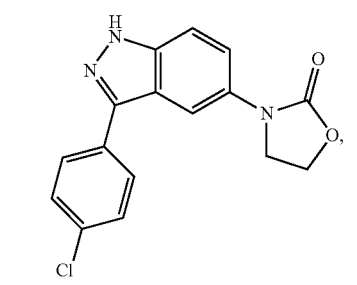
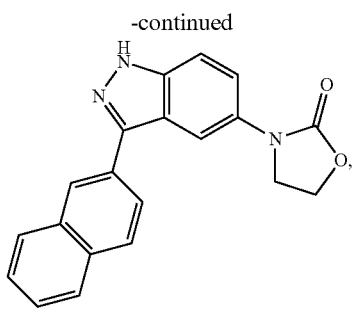
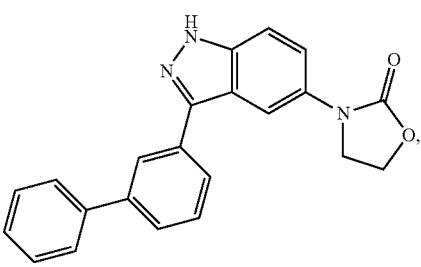
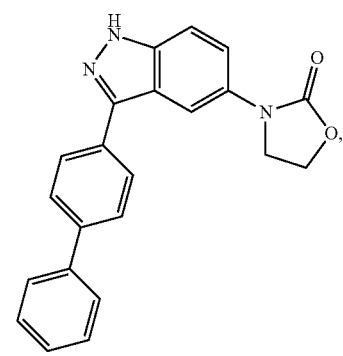
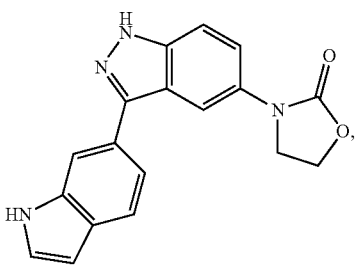
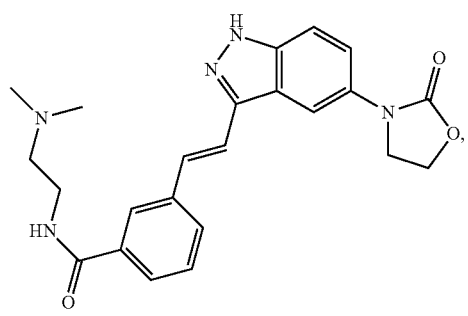

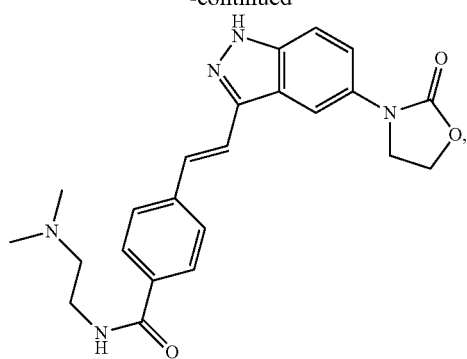
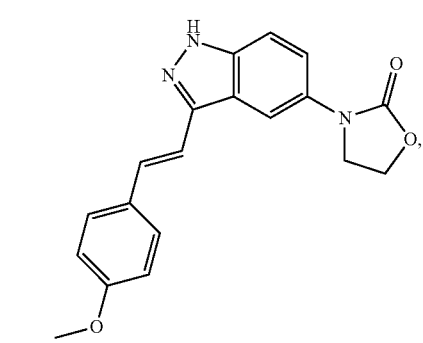
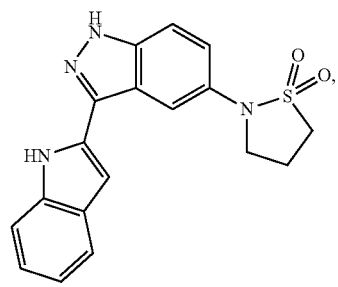
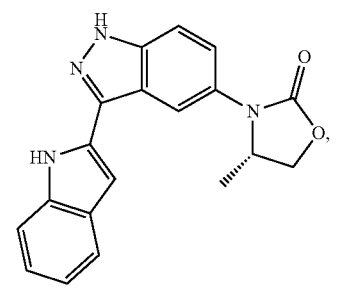
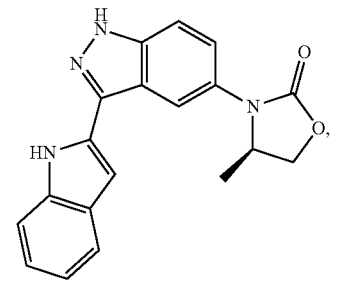
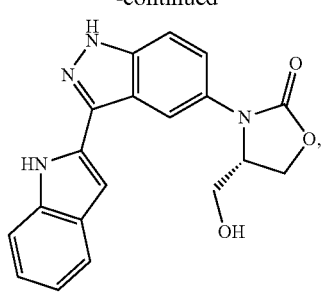
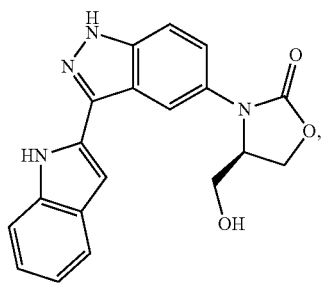
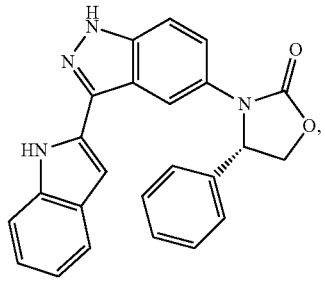
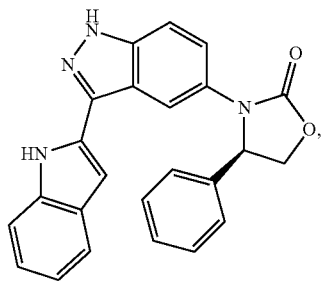
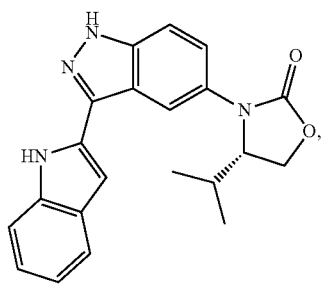
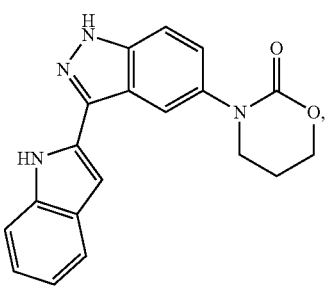

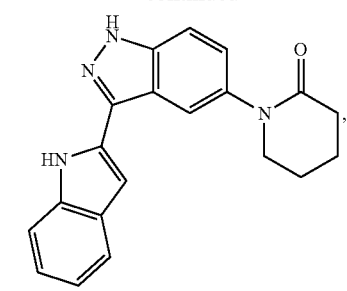
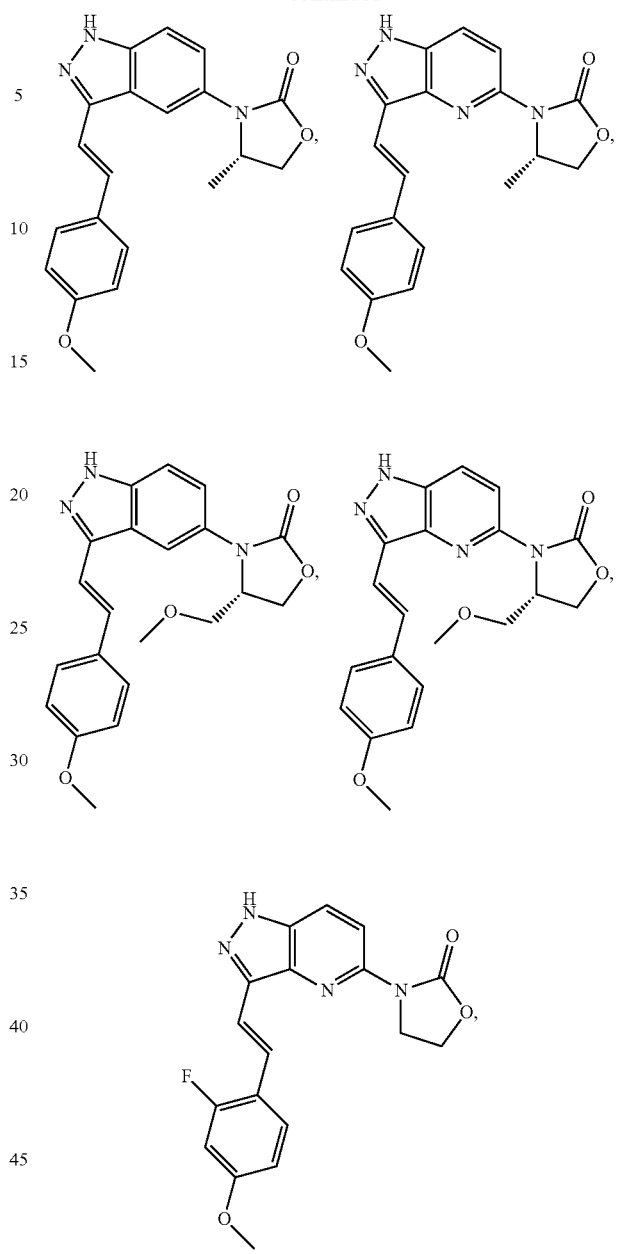
In various examples, a compound of the present disclosure has the following structure:
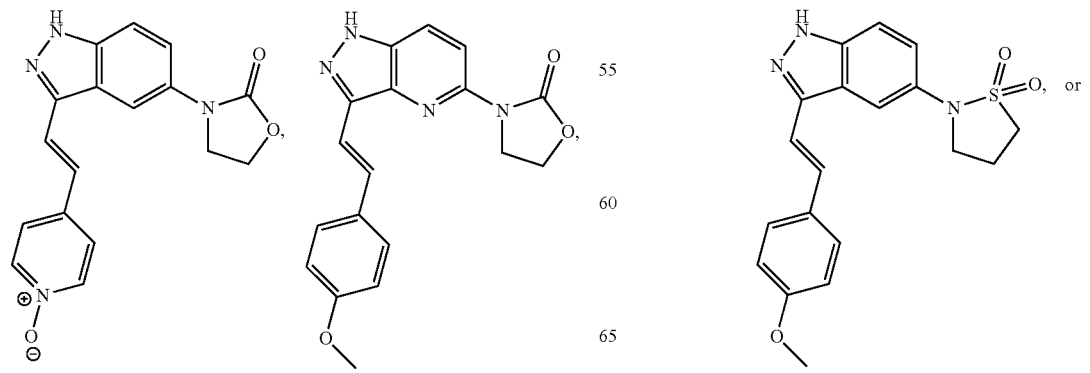

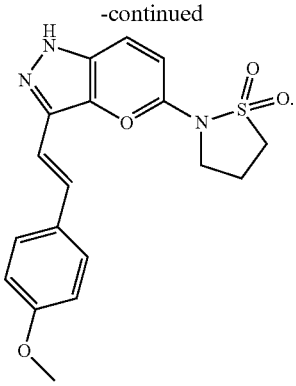

Compounds of the present disclosure may be synthesized by methods known in the art. For example, syntheses of compounds of the present disclosure are presented in Schemes 1 and 2.

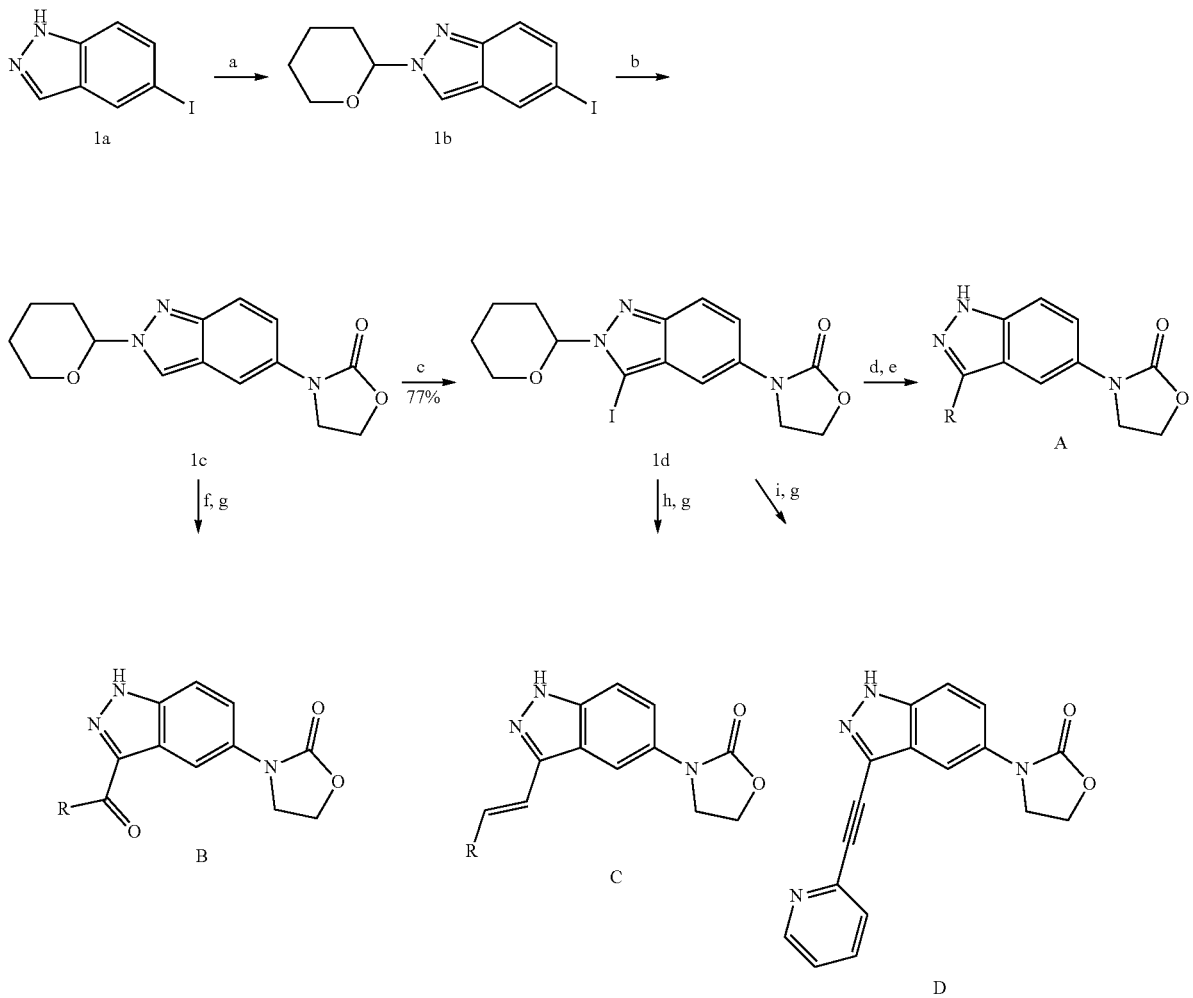

Reagents and Conditions: (a) DHP, PPTS, DCM, rt; (b) oxazolidin-2-one, CuI, trans-N,N'-dimethylcyclohexanediamine,, $K_3PO_4$, dioxane, 80° C.; (c) $I_2$, $K_2CO_3$, DMF, rt; (d) R—B(OR')$_2$, $K_3PO_4$, LiCl, dioxane, water, 80° C.; (e) 1:1 THF:0.1N TSA$_{(aq)}$; (f) TMP—MgCl—LiCl, $E^+$, THF, 0° C. (for R = Ph, $E^+$ = PhCOCl; for R = OEt, $E^+$ = ClCO$_2$Et; For R = OH treat R = CO$_2$Et with LiOH•H$_2$O in 1:1:1 THF:H$_2$O:MeOH; (g) 1:1 THF 1N HCl, rt; (h) For R = aryl/heteroaryl: (Het)Ar—CH=CH$_2$, Pd(OAc)$_2$, (o-tolyl)$_3$P, DMF, 100° C.; for R = H: vinyl boronic acid, Pd(Ph$_3$P)$_4$, $K_3PO_4$, dioxane, Δ; (i) 2-ethynylpyridine, Et$_3$N, CuI, PdCl$_2$(Ph$_3$P)$_2$, rt.

Scheme 2. Preparation of C5 substituted indazoles.

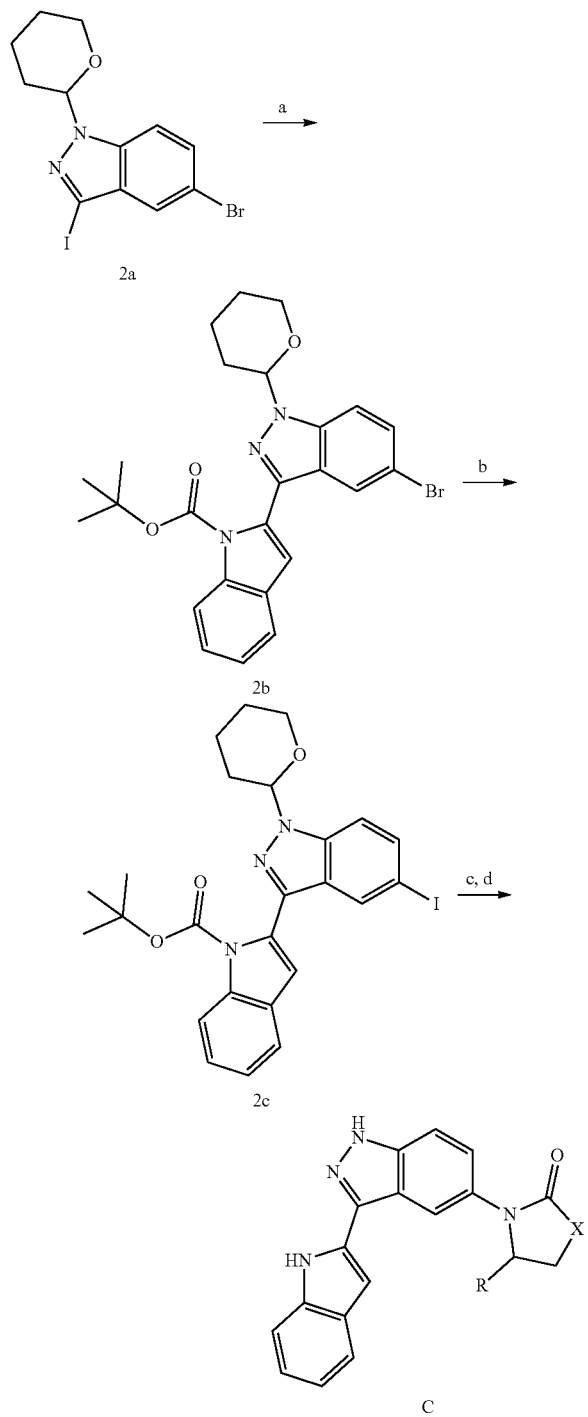

Reagents and Conditions: (a) N—BOC-indole-2-boronic acid, Pd(Ph₃P)₄, K₃PO₄, LiCl, dioxane, water, 80° C.; (b) NaI, CuI, trans-N,N'-dimethylcycohexanediamine, 80° C.; (c) lactam, carbamate or sulfonamide, CuI, trans-N,N'-dimethylcyclohexanediamine,, K₃PO₄, dioxane, 80-110° C.; (d) TIPS, TFA, DCM, rt.

In an aspect, the present disclosure provides compositions comprising one or more compound of the present disclosure. The compositions may comprise one or more pharmaceutically acceptable carrier.

Compositions comprising one or more compound of the disclosure and a pharmaceutical carrier may be prepared at a patient's bedside, or by a pharmaceutical manufacturer. The compositions may be provided in any suitable container, such as, for example, a sealed sterile vial or ampoule, and may be further packaged to include instruction documents for use by a pharmacist, physician or other health care provider. The compositions may be provided in combination with any suitable delivery form or vehicle, examples of which include, for example, liquids, caplets, capsules, tablets, inhalants, or aerosol, or the like. The delivery devices may comprise components that facilitate release of the pharmaceutical agents over certain time periods and/or intervals, and may include compositions that enhance delivery of the pharmaceuticals, such as, for example, nanoparticle, microsphere or liposome formulations, a variety of which are known in the art and are commercially available. Further, each composition described herein may comprise one or more pharmaceutical agents.

The compositions described herein may include one or more standard pharmaceutically acceptable carriers. Pharmaceutically acceptable carriers may be determined in part by the particular composition being administered, as well as by the particular method used to administer the composition. Accordingly, there are a wide variety of suitable formulations of pharmaceutical compositions of the present disclosure. Some examples of pharmaceutically acceptable carriers can be found in: *Remington: The Science and Practice of Pharmacy* (2011) 21st Edition, Philadelphia, Pa. Lippincott Williams & Wilkins. Effective formulations include, but are not limited to, oral and nasal formulations, formulations for parenteral administration, and compositions formulated for with extended release. For example, suitable carriers include excipients, or stabilizers that are nontoxic to recipients at the dosages and concentrations employed, and include buffers such as acetate, Tris, phosphate, citrate, and other organic acids; antioxidants including ascorbic acid and methionine; preservatives such as octadecyldimethylbenzyl ammonium chloride; hexamethonium chloride; benzalkonium chloride, benzethonium chloride; phenol, butyl or benzyl alcohol; alkyl parabens, such as, for example, methyl or propyl paraben; catechol; resorcinol; cyclohexanol; 3-pentanol; and m-cresol; amino acids such as, for example, glycine, glutamine, asparagine, histidine, arginine, or lysine; monosaccharides, disaccharides, and other carbohydrates including, for example, glucose, mannose, or dextrins; chelating agents such as EDTA; tonicifiers such as trehalose and sodium chloride; sugars such as, for example, sucrose, mannitol, trehalose or sorbitol; surfactant such as polysorbate; salt-forming counter-ions such as sodium; and/or non-ionic surfactants such as Tween or polyethylene glycol (PEG). The pharmaceutical compositions may comprise other therapeutic agents.

Examples of compositions, which may be suitable for oral administration, include, but are not limited to, (a) liquid solutions, such as, for example, an effective amount of a compound of the present disclosure suspended in diluents, such as, for example, water, saline or PEG 400; (b) capsules, sachets, depots or tablets, each containing a predetermined amount of the active ingredient, as liquids, solids, granules or gelatin; (c) suspensions in an appropriate liquid; (d) suitable emulsions; and (e) patches. The liquid solutions described above may be sterile solutions. The compositions may comprise, for example, one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers.

A composition may be in unit dosage form. In such form, the composition may be subdivided into unit doses containing appropriate quantities of the active component. The unit dosage form may be a packaged preparation, the package containing discrete quantities of preparation, such as, for example, packeted tablets, capsules, and powders in vials or ampoules. Also, the unit dosage form may be a capsule, tablet, cachet, or lozenge itself, or it may be the appropriate number of any of these in packaged form. The composition may, if desired, also contain other compatible therapeutic agents. The compositions may deliver the compounds of the disclosure in a sustained release formulation.

In an aspect, the present disclosure provides methods of using one or more compounds of the present disclosure. For example, the compounds can be used to treat an individual having cancer, a neurologic disease, a metabolic condition, an orthopedic condition, a mental health condition, a viral infection, or a combination thereof.

The steps of the method described in the various embodiments and examples disclosed herein are sufficient to carry out the methods of the present disclosure. Thus, in an embodiment, the method consists essentially of a combination of the steps of the methods disclosed herein. In another embodiment, the method consists of such steps.

For example, a method of treating comprises administering to an individual one or more compound of the present disclosure or a composition comprising one or more compounds of the present disclosure.

The method may be carried out in an individual who has been diagnosed with or is suspected of having cancer (e.g., prostate cancer, ovarian cancer, pymphoma, lung, colorectal, glioma, hepatocellular, and the like, and combinations thereof), neurologic diseases (e.g., neurodegenerative diseases such as, for example, Alzheimer's Disease and the like), metabolic conditions (e.g., obesity, type-2 diabetes, non-alcoholic fatty liver disease (NAFLD), and the like, and combinations thereof), orthopedic conditions (e.g., for treating one or more fractures, for treating muscle atrophy, and the like, and combinations thereof), mental health conditions (e.g., anxiety, depression, obsessive compulsive disorder, bipolar disorder, schizophrenia, and the like, and combinations thereof), a viral infection (i.e., therapeutic use) (e.g., HIV, TB, and the like, and combinations), or a combination thereof.

A method may be carried out in individuals who have a relapse or a high risk of relapse after being treated for cancer, neurodegenerative diseases, metabolic conditions, orthopedic conditions, mental health conditions, a viral infection, or a combination thereof.

A method of the present disclosure may be carried out in an individual in need of prophylaxis or treatment for viral infections/illnesses. For example, a method of treating a viral infection comprises administering to an individual in need of treatment a compound or composition of the present disclosure, such that the virus is eliminated or the individual is cured from the virus. In another example, a method of treating a viral infection comprises administering to an individual in need of treatment a compound or composition of the present disclosure, such that the viral load is reduced.

A method of the present disclosure comprises administering to an individual in need of treatment one or more compounds or a composition comprising one or more compounds of the present disclosure. Compositions comprising the compounds described herein may be administered to an individual using any known method and route, including oral, parenteral, subcutaneous, intraperitoneal, intrapulmonary, intranasal, and intracranial injections. Parenteral infusions include, but are not limited to, intramuscular, intravenous, intraarterial, intraperitoneal, subcutaneous administration, and the like. Administration may also include, but is not limited to, topical and/or transdermal administrations.

The dose of the composition comprising a compound of the present disclosure and a pharmaceutical agent may necessarily be dependent upon the needs of the individual to whom the composition of the disclosure is to be administered. These factors include, for example, the weight, age, sex, medical history, and nature and stage of the disease for which a therapeutic or prophylactic effect is desired. The compositions may be used in conjunction with any other conventional treatment modality designed to improve the disorder for which a desired therapeutic or prophylactic effect is intended, non-limiting examples of which include, but are not limited to, surgical interventions and radiation therapies. For example, the compositions are used in combination with (e.g., co-administered with) one or more known anti-cancer drug (e.g., DNA damaging anti-cancer drugs) and/or known anti-viral drug.

Methods of the present disclosure may be used on various individuals. In various examples, an individual is a human or non-human mammal. Examples of non-human mammals include, but are not limited to, farm animals, such as, for example, cows, hogs, sheep, and the like, as well as pet or sport animals such as, for example, horses, dogs, cats, and the like. Additional non-limiting examples of individuals include, but are not limited to, rabbits, rats, mice, and the like. The compounds or compositions of the present disclosure may be administered to individuals for example, in pharmaceutically acceptable carriers, which facilitate transporting the compounds from one organ or portion of the body to another organ or portion of the body.

The following examples are presented to illustrate the present disclosure. They are not intended to be limiting in any matter.

Example 1

This example provides a description of synthesis of 3-(3-(Benzofuran-3-yl)-1H-indazol-5-yl)oxazolidin-2-one (1), 3-(3-(benzofuran-3-yl)-1-((2-(trimethylsilyl)ethoxy)methyl)-1H-indazol-5-yl)oxazolidin-2-one, 3-(3-iodo-1-((2-(trimethylsilyl)ethoxy)methyl)-1H-indazol-5-yl)oxazolidin-2-one, 3-(3-iodo-1H-indazol-5-yl)oxazolidin-2-one, 3-(1H-indazol-5-yl)oxazolidin-2-one, 3-(1-((2-(trimethylsilyl)ethoxy)methyl)-1H-indazol-5-yl)oxazolidin-2-one, and 5-iodo-1-((2-(trimethylsilyl)ethoxy)methyl)-1H-indazole.

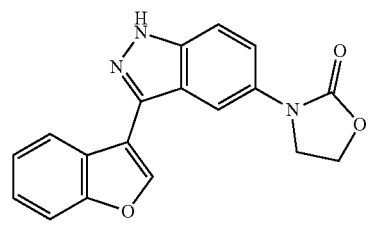 [SMILES: O=C1OCCN1c1ccc2[nH]nc(-c3coc4ccccc34)c2c1]

3-(3-(Benzofuran-3-yl)-1H-indazol-5-yl)oxazolidin-2-one (1). A solution of Intermediate 1A (0.16 mmol) 1 mL of 1.0M TBAF in THF in a small pressure tube was treated with ethylene diamine (48 μL, 0.64 mmol), sealed, warmed to 65° C. and allowed to stir for 4 hour (h or hr). An additional 320 μL of TBAF was added and stirring continued for another hour. The crude reaction mixture was partitioned between ethyl acetate and water. The combined organic layers were washed with brine, dried over Na$_2$SO$_4$, filtered and concentrated, purified by flash column chromatography (50% Ethyl acetate/hexane→5% Methanol/dichloromethane) to afford the title product as 15 mg of a yellow solid (29% over 2 steps). $^1$HNMR (600 MHz, DMSO-d6) δ 13.35 (s, 1H), 8.84 (s, 1H), 8.36 (d, J=7.7 Hz, 1H), 7.93 (s, 1H), 7.90 (dd, J=9.0, 1.9 Hz, 1H), 7.70 (d, J=8.0 Hz, 1H), 7.66 (d, J=9.0 Hz, 1H), 7.45-7.41 (m, 1H), 7.39 (t, J=7.3 Hz, 1H), 4.54-4.45 (m, 2H), 4.28-4.19 (m, 2H). $^{13}$CNMR (151 MHz, DMSO) δ 155.33, 137.43, 132.81, 126.71, 120.37, 111.00, 109.12, 93.19, 61.50, 45.54. MS (ES−): m/z=327.9 (M−H).

Intermediate 1A

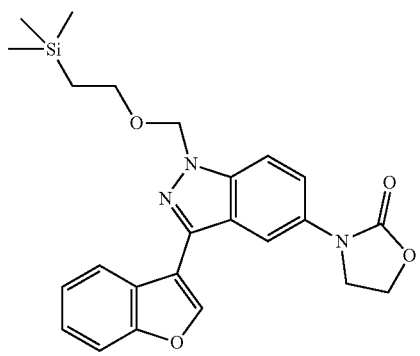 [SMILES: C[Si](C)(C)CCOCn1nc(-c2coc3ccccc23)c2cc(N3CCOC3=O)ccc21]

3-(3-(benzofuran-3-yl)-1-((2-(trimethylsilyl)ethoxy) methyl)-1H-indazol-5-yl)oxazolidin-2-one. Intermediate 1B (75 mg, 0.16 mmol), benzofuran-3-boronic acid (53 mg, 0.33 mmol) and PdCl2 (dppf) (13 mg, 0.016 mmol) were combined in a flea-bar equipped 2 dram vial and taken up in dioxane (2 mL). A solution of potassium carbonate (66 mg, 0.48 mmol) in 0.5 mL water was added to the vial and this mixture was sparged with N$_2$ for 2 minutes. The vial was capped, heated to 80° C. and allowed to stir overnight. The crude reaction mixture was partitioned between ethyl acetate and water. The combined organic layers were washed with brine, dried over Na2SO4, filtered and concentrated, purified by flash column chromatography (50% Ethyl acetate/dichloromethane) to afford 83 mg of a brown oil. The HNMR indicated that this was approximately a 3:1 mixture of isomers. This material was not purified further and was taken directly to the next step. $^1$H NMR (Major isomer, 400 MHz, Chloroform-d) δ 8.28 (d, J=7.5 Hz, 1H), 8.21 (s, 1H), 7.93 (s, 1H), 7.80 (d, J=9.1 Hz, 1H), 7.66 (d, J=9.3 Hz, 1H), 7.59 (d, J=7.8 Hz, 1H), 7.42-7.36 (m, 2H), 5.84 (s, 2H), 4.55 (d, J=15.6 Hz, 2H), 4.18 (t, J=7.9 Hz, 2H), 3.68 (t, J=8.0 Hz, 2H), 0.95 (t, J=7.9 Hz, 2H), −0.04 (s, 9H).

Intermediate 1B

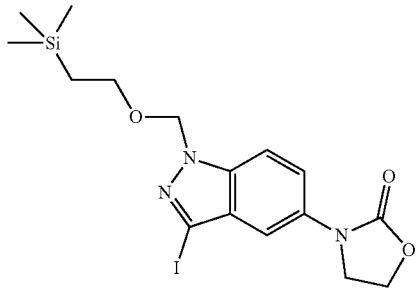 [SMILES: C[Si](C)(C)CCOCn1nc(I)c2cc(N3CCOC3=O)ccc21]

3-(3-iodo-1-((2-(trimethylsilyl)ethoxy)methyl)-1H-indazol-5-yl)oxazolidin-2-one. Sodium hydride (60%, 64 mg, 1.59 mmol) was cautiously added to an ice cooled solution of Intermediate 1C (400 mg, 1.22 mmol) in anhydrous DMF. After stirring for 20 minutes, the reaction mixture was treated with SEM-chloride (258 mL, 1.46 mmol) dropwise. After addition was complete, the reaction mixture was allowed to stir for 40 minutes, after which, the mixture was poured into water and extracted twice with ethyl acetate. The combined organic layers were washed three times with water, once with brine, dried over Na$_2$SO$_4$, filtered and concentrated to a crude oil. The desired product was isolated as 588 mg of a yellow oil which crystalized upon standing after column chromatography (5% methanol/dichloromethane). $^1$H NMR shows this material to be 3:1 mixture of N1:N2 SEM protected regioisomers. $^1$H NMR (Major isomer, 400 MHz, Chloroform-d) δ 8.02 (d, J=9.1 Hz, 1H), 7.58 (d, J=9.2 Hz, 1H), 7.32 (s, 1H), 5.72 (s, 2H), 4.55 (t, J=7.8 Hz, 2H), 4.19 (t, J=7.6 Hz, 2H), 3.56 (t, J=8.2 Hz, 2H), 0.91-0.86 (m, 2H), −0.05 (s, 9H).

Intermediate 1C

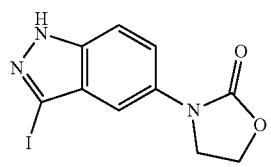 [SMILES: O=C1OCCN1c1ccc2[nH]nc(I)c2c1]

3-(3-iodo-1H-indazol-5-yl)oxazolidin-2-one. An ice cooled solution of Intermediate 1D (633 mg, 3.1 mmol) in DMF (10 mL) was treated with potassium carbonate (861 mg, 4.1 mmol) and iodine (1.03 g, 4.1 mmol). After 1 hour the reaction mixture was poured into a vigorously stirring ice water mixture. The resulting brown slurry was treated with an aqueous solution of sodium thiosulfate (3.3 g) and potassium carbonate (0.2 g) in 30 mL water. This mixture was allowed to stir until it became a white suspension. The title product was collected by filtration (844 mg, 82%). MS (ES-): m/z=327.9 (M−H). $^1$H NMR (600 MHz, DMSO-d6) δ 13.52 (s, 1H), 7.75 (dd, J=9.0, 2.1 Hz, 1H), 7.59 (d, J=9.0 Hz, 1H), 7.47 (d, J=1.6 Hz, 1H), 4.60-4.36 (m, 2H), 4.27-4.09 (m, 2H). $^{13}$C NMR (151 MHz, DMSO) δ 155.33, 137.43, 132.81, 126.71, 120.37, 111.00, 109.12, 93.19, 61.50, 45.54.

Intermediate 1D

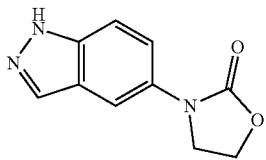 [SMILES: O=C1OCCN1c1ccc2[nH]ncc2c1]

3-(1H-indazol-5-yl)oxazolidin-2-one. A solution of Intermediate 1E (5.07 g, 15.2 mmol) in 20 mL dicholoromethane was treated with 10 mL trifluoroacetic acid and stirred at room temperature for 2 hours. Another 10 mL of trifluoroacetic acid was added. After an additional 1 hour of stirring the reaction appeared to be complete and was concentrated in vacuo. The crude material was partitioned between ethyl acetate and saturated, aqueous $K_2CO_3$. The combined organics were washed with brine, dried over $Na_2SO_4$ and quickly filtered as a ppt was beginning to form. The ethyl acetate was removed in vacuo and the residue was triturated with ethyl acetate. $^1H$ NMR of the triturated solid indicated it was the N-hydroxymethylindazole formed by incomplete deprotection. This material was stirred overnight in 4 M HCl in dioxane (10 mL). An additional 20 mL of 4 M HCl in dioxane was poured into an ice/water mixture and carefully neutralized with saturated, aqueous solution of $K_2CO_3$. This mixture was extracted with ethyl acetate twice. The combined organics were washed with brine, dried over $Na_2SO_4$, filtered, concentrated and urified by flash column chromatography (50% Ethyl acetate/Dichloromethane) to afford the desired product as 646 mg of a white solid (21%). $^1H$ NMR (400 MHz, DMSO-d6) δ 13.07 (s, 1H), 8.08-8.04 (m, 1H), 7.76 (d, J=2.0 Hz, 1H), 7.72 (dd, J=9.0, 2.1 Hz, 1H), 7.56 (d, J=9.0 Hz, 1H), 4.45 (dd, J=9.0, 7.0 Hz, 2H), 4.11 (dd, J=8.9, 7.1 Hz, 2H).

Intermediate 1E

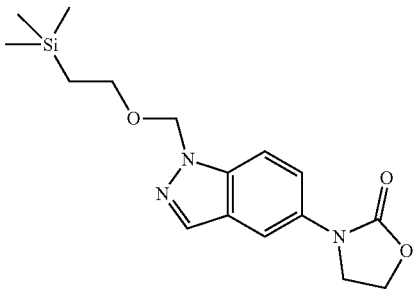 [SMILES: C[Si](C)(C)CCOCn1ncc2cc(N3CCOC3=O)ccc21]

3-(1-((2-(trimethylsilyl)ethoxy)methyl)-1H-indazol-5-yl) oxazolidin-2-one. Intermediate 1F a 1:1 mixture of regioisomers. $^1H$ NMR (400 MHz, Chloroform-d) δ 8.00 (d, J=0.9 Hz, 2H), 7.79 (d, J=2.1 Hz, 1H), 7.77 (d, J=2.1 Hz, 1H), 7.74 (dd, J=2.1, 0.7 Hz, 2H), 7.61 (d, J=1.6 Hz, 1H), 7.59 (t, J=0.8 Hz, 1H), 5.74 (s, 4H), 4.53 (dd, J=9.2, 6.7 Hz, 5H), 4.14 (dd, J=9.2, 6.8 Hz, 5H), 3.56-3.51 (m, 4H), 0.91-0.85 (m, 4H), −0.06 (s, 18H).

Intermediate 1F

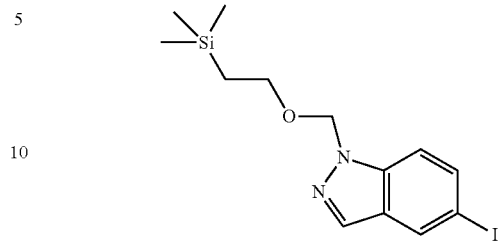

5-iodo-1-((2-(trimethylsilyl)ethoxy)methyl)-1H-indazole. 5-iodo-1H-indazole $^1H$ NMR (400 MHz, Chloroform-d) δ 8.11 (dd, J=1.5, 0.6 Hz, 1H), 7.94 (d, J=0.9 Hz, 1H), 7.66 (dd, J=8.8, 1.6 Hz, 1H), 7.38 (d, J=8.8 Hz, 1H), 5.72 (s, 2H), 3.58-3.47 (m, 2H), 0.93-0.82 (m, 2H), −0.06 (s, 9H).

Example 2

This example provides a description of synthesis of 3-(3-(Benzofuran-2-yl)-1H-indazol-5-yl)oxazolidin-2-one.

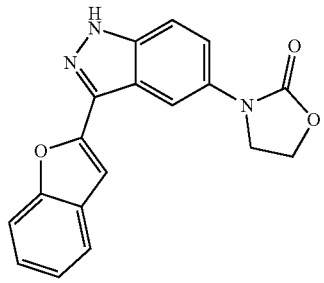 [SMILES: O=C1OCCN1c1ccc2[nH]nc(-c3cc4ccccc4o3)c2c1]

3-(3-(Benzofuran-2-yl)-1H-indazol-5-yl)oxazolidin-2-one (2). Intermediate 1C (100 mg, 0.30 mmol), benzofuran-2-boronic acid (59 mg, 0.37 mmol), lithium chloride (38 mg, 0.91 mmol) and Pd(Ph$_3$P)$_4$ (11 mg, 0.009 mmol) were combined in a flea-bar equipped 2-dram vial and taken up in 3 mL dioxane. This mixture was treated with a solution of Na$_2$CO$_3$ (161 mg, 1.52 mmol) in 1.5 mL water, sparged with N$_2$ for 3 minutes, sealed, heated to 100° C. and stirred overnight. The reaction was poured in to 50 mL water and extracted twice with EtOAc (20 mL). The combined organic layers were washed with brine, dried (Na2SO4), filtered, concentrated onto SiO$_2$ and purified by flash column chromatography (1:1 EtOAc:DCM). The resulting material required a second purification by flash column chromatography (5% MeOH/DCM) to afford the title compound as 24 mg of a white solid (25%). $^1$HNMR (600 MHz, DMSO-d6) δ 13.59 (s, 1H), 8.14 (d, J=1.7 Hz, 1H), 7.86 (dd, J=9.1, 2.0 Hz, 1H), 7.73 (d, J=7.5 Hz, 1H), 7.71-7.66 (m, 2H), 7.48 (s, 1H), 7.39-7.34 (m, 1H), 7.34-7.28 (m, 1H), 4.53-4.47 (m, 2H), 4.28-4.21 (m, 2H). $^{13}$CNMR (151 MHz, DMSO) δ 155.46, 153.91, 150.57, 138.17, 135.22, 133.19, 128.44, 124.53, 123.31, 121.13, 120.25, 119.86, 111.15, 109.71, 102.72, 61.53, 45.77. MS (ES$^+$): m/z=320.4, 661.3 (M+H, 2M+Na).

Example 3

This example provides a description of synthesis of 3-(3-(1H-indol-2-yl)-1H-indazol-5-yl)oxazolidin-2-one.

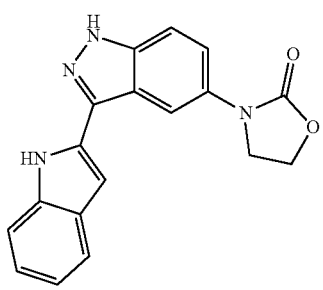 [SMILES: O=C1OCCN1c1ccc2[nH]nc(-c3cc4ccccc4[nH]3)c2c1]

3-(3-(1H-indol-2-yl)-1H-indazol-5-yl)oxazolidin-2-one (3) was prepared using the same procedure as Example 2 but benzofuran-2-boronic acid was replaced with indole-2-boronic acid, pinacol ester (44 mg, 0.18 mmol, 1.2 eq). After aqueous/EtOAc extraction, the title compound was isolated by flash-column chromatography (1:1 EtOAc:DCM) as 36.4 mg of a tan solid (75%). $^1$HNMR (600 MHz, DMSO-d6) δ 13.36 (s, 1H), 11.59 (s, 1H), 8.10 (s, 1H), 7.82 (dd, J=9.0, 1.9 Hz, 1H), 7.64 (d, J=9.0 Hz, 1H), 7.60 (d, J=7.8 Hz, 1H), 7.45 (d, J=8.0 Hz, 1H), 7.11 (t, J=7.5 Hz, 1H), 7.09 (s, 1H), 7.02 (t, J=7.4 Hz, 1H), 4.53-4.46 (m, 2H), 4.28-4.22 (m, 2H). $^{13}$CNMR (151 MHz, DMSO) δ 155.51, 138.48, 137.45, 136.43, 132.69, 131.36, 128.48, 121.62, 120.03, 119.96, 119.78, 119.19, 111.46, 110.91, 109.84, 99.56, 61.53, 45.84. MS (ES$^-$): m/z=317.1 (M−H).

Example 4

This example provides a description of synthesis of (E)-3-(3-(2-(pyridin-2-yl)vinyl)-1H-indazol-5-yl)oxazolidin-2-one and (E)-3-(3-(2-(pyridin-2-yl)vinyl)-1-((2-(trimethylsilyl)ethoxy)methyl)-1H-indazol-5-yl)oxazolidin-2-one.

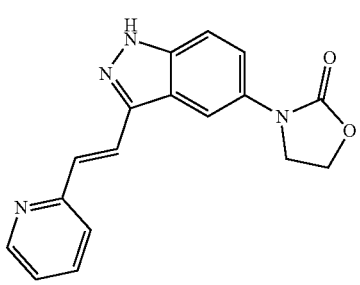 [SMILES: O=C1OCCN1c1ccc2[nH]nc(/C=C/c3ccccn3)c2c1]

(E)-3-(3-(2-(pyridin-2-yl)vinyl)-1H-indazol-5-yl)oxazolidin-2-one (4). The title compound was prepared using the same procedure as Example 1 replacing Intermediate 1A with Intermediate 4A (45 mg, 0.10 mmol, 1 eq). The final product was isolated after column chromatography (5% MeOH/DCM) as 15 mg of a tan solid (38%). $^1$HNMR (600 MHz, DMSO-d6) δ 13.33 (s, 1H), 8.60 (ddd, J=4.7, 1.6, 0.7 Hz, 1H), 8.07 (d, J=1.7 Hz, 1H), 7.96 (d, J=16.3 Hz, 1H), 7.81 (ddt, J=7.6, 4.1, 1.9 Hz, 2H), 7.66 (d, J=7.8 Hz, 1H), 7.61 (d, J=9.0 Hz, 1H), 7.51 (d, J=16.3 Hz, 1H), 7.27 (ddd, J=7.5, 4.8, 1.0 Hz, 1H), 4.61-4.39 (m, 2H), 4.32-4.17 (m, 2H). $^{13}$CNMR (151 MHz, DMSO) δ 155.47, 154.98, 149.52, 141.57, 138.40, 136.81, 132.74, 128.49, 123.60, 122.37, 122.33, 120.85, 119.88, 110.90, 109.73, 61.51, 45.82. MS (ES$^+$): m/z=307.3 (M+H).

Intermediate 4A

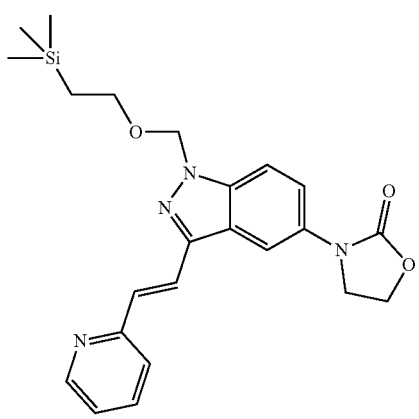 [SMILES: C[Si](C)(C)CCOCn1nc(/C=C/c2ccccn2)c2cc(N3CCOC3=O)ccc21]

(E)-3-(3-(2-(pyridin-2-yl)vinyl)-1-((2-(trimethylsilyl)ethoxy)methyl)-1H-indazol-5-yl)oxazolidin-2-one. Intermediate 1B (100 mg, 0.22 mmol), 2-vinylpyridine (30 μL, 0.28 mmol) and DIPEA (80 μL, 0.46 mmol) were combined in a flea-bar equipped 2-dram vial, taken up in 1 mL of anhydrous DMF and sparged with $N_2$ for 2 minutes. Palladium (II) acetate (5 mg, 0.022 mmol) and tri-(o-tolyl)phosphine (21 mg, 0.068 mmol) were quickly added. This mixture was sparged an addition minute with $N_2$, sealed and allowed to stir overnight at 100° C. The reaction mixture was poured into water (20 mL) and extracted twice with EtOAc (20 mL). The combined organic layers were washed three times with water (10 mL), once with brine, dried ($Na_2SO_4$), filtered, concentrated on to SiO2 and purified by flash column chromatography (1:1 EtOAc:DCM) to afford the title compound as 45 mg of a yellow solid. This material was shown by HNMR to be a mixture of regioisomers. The material was taken on as is. $^1$H NMR (400 MHz, Chloroform-d) δ 8.65 (d, J=4.1 Hz, 1H), 7.95 (d, J=6.7 Hz, 1H), 7.89 (d, J=8.5 Hz, 2H), 7.71 (t, J=7.7 Hz, 1H), 7.65-7.54 (m, 2H), 7.49 (d, J=7.8 Hz, 1H), 7.24-7.17 (m, 1H), 5.76 (s, 2H), 4.56 (t, J=7.8 Hz, 2H), 4.20 (t, J=7.9 Hz, 2H), 3.59 (t, J=8.1 Hz, 2H), 0.94-0.87 (m, 2H), −0.05 (s, 9H).

Example 5

This example provides a description of synthesis of 3-(3-(1H-imidazol-1-yl)-1H-indazol-5-yl)oxazolidin-2-one.

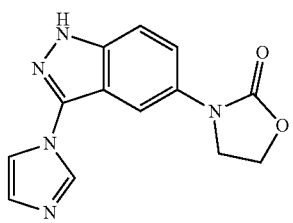 [SMILES: O=C1OCCN1c1ccc2[nH]nc(-n3ccnc3)c2c1]

3-(3-(1H-imidazol-1-yl)-1H-indazol-5-yl)oxazolidin-2-one (5). The title compound was prepared using the same procedure as Example 1 replacing Intermediate 1A with Intermediate 5A (47.4 mg, 0.12 mmol, 1 eq). Purification was performed using flash-column chromatography (5% MeOH/DCM) to afford the final product as 10.9 mg of an off-white solid (34%). $^1$HNMR (600 MHz, DMSO-d6) δ

13.28 (s, 1H), 8.33 (s, 1H), 7.91 (dt, J=9.2, 1.8 Hz, 1H), 7.81 (s, 1H), 7.76 (d, J=1.9 Hz, 1H), 7.65 (d, J=9.1 Hz, 1H), 7.21 (s, 1H), 4.55-4.37 (m, 2H), 4.27-4.13 (m, 2H). $^{13}$CNMR (151 MHz, DMSO) δ 155.37, 138.46, 136.09, 133.04, 129.46, 120.96, 120.94, 118.65, 113.66, 111.36, 107.80, 61.54, 45.61. MS (ES$^+$): m/z=270.3 (M+H).

Intermediate 5A

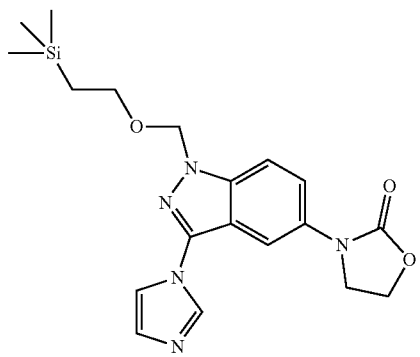 [SMILES: C[Si](C)(C)CCOCn1nc(-n2ccnc2)c2cc(N3CCOC3=O)ccc21]

3-(3-(1H-imidazol-1-yl)-1-((2-(trimethylsilyl)ethoxy)methyl)-1H-indazol-5-yl)oxazolidin-2-one. Intermediate 1B (100 mg, 0.22 mmol), imidazole (15 mg, 0.22 mmol), 1,10-phenanthroline (8 mg, 0.044 mmol) and Cs$_2$CO$_3$ (108 mg, 0.33 mmol) were combined in a flea-bar equipped 2-dram vial and taken up in 1 mL DMF. The mixture was sparged with N$_2$, sealed and allowed to stir overnight at 100° C. The reaction mixture was poured into water (~20 mL) and extracted twice with EtOAc (~20 mL). The combined organic layers were washed three times with water (~10 mL), once with brine, dried (Na$_2$SO$_4$), filtered, concentrated on to SiO2 and purified by flash column chromatography (1:1 EtOAc:DCM→5% MeOH/DCM) to afford the title compound as 47.4 mg of a yellow solid. The material was taken on directly to the next step.

Example 6

This example provides a description of synthesis of 3-(3-phenyl-1H-indazol-5-yl)oxazolidin-2-one, 3-(3-iodo-2-(tetrahydro-2H-pyran-2-yl)-2H-indazol-5-yl)oxazolidin-2-one, 3-(2-(tetrahydro-2H-pyran-2-yl)-2H-indazol-5-yl)oxazolidin-2-one, and 5-iodo-2-(tetrahydro-2H-pyran-2-yl)-2H-indazole.

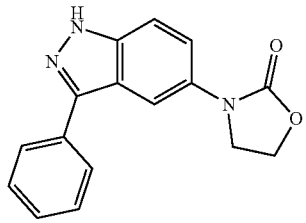 [SMILES: O=C1OCCN1c1ccc2[nH]nc(-c3ccccc3)c2c1]

3-(3-phenyl-1H-indazol-5-yl)oxazolidin-2-one (6). Intermediate 6A (35 mg, 0.085 mmol) was combined with phenylboronic acid (16 mg, 0.13 mmol), K$_3$PO$_4$ (55 mg, 0.26 mmol) and PdCl$_2$(dppf) (21 mg, 0.026 mmol) in a flea-bar equipped 1 dram vial. This mixture was taken up 2 mL dioxane, treated with 0.5 mL water. After sparging the mixture for 2 minutes with N$_2$, the vial was sealed, heated to 80° C. and allowed to stir overnight. In the morning, the mixture was poured into water (~10 mL) and extracted twice with EtOAc (~10 mL). The combined organic layers were washed with brine, dried (Na$_2$SO$_4$), filtered, concentrated on to SiO$_2$ and purified on a Teledyne-ISCO Combiflash unit through a 4 g column (0-70% EtOAc/Heptane) to afford the 17 mg of a solid which was taken up in 1:1 THF:HCl (1.0 M) and allowed to stir 2 hours. The desired product precipitated and was collected by filtration and dried to afford the title product as 11.1 mg of a white solid (47%). $^1$H NMR (400 MHz, Chloroform-d) δ 7.94 (d, =6.6 Hz, 3H), 7.85 (d, J=9.5 Hz, 1H), 7.54 (t, J=8.0 Hz, 3H), 7.48-7.38 (m, 1H), 4.54 (t, =7.9 Hz, 2H), 4.21-4.12 (m, 2H).

Intermediate 6A

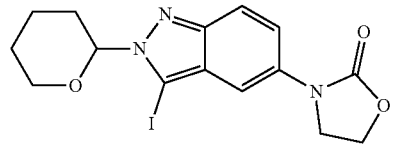

3-(3-iodo-2-(tetrahydro-2H-pyran-2-yl)-2H-indazol-5-yl)oxazolidin-2-one. Intermediate 6A was prepared according to the procedure of Lam, et. al (*Chem. Eur. J.*, 2016, 22, 4440-4446). TMP-MgCl.LiCl (1.0M, 27.9 mL) was added dropwise to a −10° C. solution of Intermediate 6B (5.3 g, 18.6 mmol) in anhydrous THF (62 mL) under an N$_2$ atmosphere. After 60 minutes, a solution of iodine (7.6 g, 29.8 mmol) in 65 mL anhydrous THF was added cautiously to the reaction mixture. After addition was complete, the mixture was allowed to stir for 1 hour while eventually returning to room temperature. The reaction mixture was quenched with a saturated, aqueous NH$_4$C$_1$ followed by sufficient amount of saturated aqueous K$_2$CO$_3$ solution to keep the pH >7. A solution of saturated Na$_2$S$_2$O$_3$ was added to reduce unconsumed I$_2$. A two-phase mixture was formed. The aqueous layer was extracted twice with EtOAc (50 mL). The combined organic layers were washed with washed with brine, dried (Na$_2$SO$_4$), filtered and concentrated. The crude material was purified on a Teledyne-ISCO Combiflash unit through an 80 g column (0-5% MeOH/DCM) to afford the title product as 5.92 grams of an off-white solid (77%). $^1$H NMR (400 MHz, DMSO-d6) δ 7.75 (dd, J=9.4, 1.9 Hz, 1H), 7.71 (d, J=9.3 Hz, 1H), 7.37 (d, J=1.4 Hz, 1H), 5.78 (dd, J=9.6, 2.4 Hz, 1H), 4.53-4.36 (m, 2H), 4.24-4.07 (m, 2H), 3.96 (d, J=11.7 Hz, 1H), 3.78-3.63 (m, 1H), 2.48-2.40 (m, 1H), 2.16-1.94 (m, 2H), 1.77 (dt, J=21.1, 10.7 Hz, 1H), 1.59 (t, J=6.1 Hz, 2H). $^{13}$C NMR (101 MHz, DMSO) δ 155.18, 145.50, 133.72, 126.35, 121.40, 118.96, 107.92, 87.26, 80.21, 67.01, 61.49, 45.40, 40.14, 39.93, 39.72, 39.51, 39.30, 39.09, 38.88, 29.00, 24.57, 21.78.

Intermediate 6B

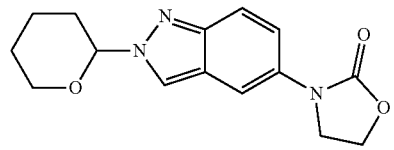 [SMILES: O=C1OCCN1c1ccc2nn(C3CCCCO3)cc2c1]

3-(2-(tetrahydro-2H-pyran-2-yl)-2H-indazol-5-yl)oxazolidin-2-one. Intermediate 6C (10.5 g, 31.9 mmol) was combined with oxazolidin-2-one (3.34 g, 38.4 mmol), Copper (I) iodide (1.22 g, 6.38 mmol) and $K_3PO_4$ (14.7 g, 64 mmol) in a 350 mL glass pressure vessel equipped with a large stirbar. The mixture was taken up in 200 mL anhydrous dioxane, treated with trans-N,N'-dimethylaminocyclohexane-1,2-diamine (1.97 mL, 12.8 mmol). After 5 minutes of $N_2$ sparging the mixture was sealed, heated to 100 C and allowed to stir for 4 hours, forming a thick, blue slurry. This mixture was cooled, poured into ~200 mL water and extracted with EtOAc (3×150 mL). The combined organics were washed with brine, dried ($Na_2SO_4$), filtered and concentrated onto SiO2. The SiO2 plug was loaded into a sample cartridge and purified on an Teledyne-ISCO Combiflash unit through a 120 g column (0-5% MeOH/DCM) to isolate 6.46 g of product as an orange oil which crystalized upon standing (71%). $^1$H NMR (400 MHz, DMSO-d6) δ 8.46 (s, 1H), 7.71 (dd, J=9.4, 2.0 Hz, 1H), 7.66 (d, J=9.4 Hz, 1H), 7.63 (d, J=1.5 Hz, 1H), 5.73 (dd, J=9.6, 2.6 Hz, 1H), 4.50-4.38 (m, 2H), 4.10 (dd, J=9.0, 7.1 Hz, 2H), 3.99 (d, J=12.5 Hz, 1H), 3.76-3.65 (m, 1H), 2.25-2.13 (m, 1H), 2.09-2.01 (m, 1H), 1.96 (dd, J=14.4, 5.2 Hz, 1H), 1.79-1.64 (m, 1H), 1.64-1.52 (m, 2H). $^{13}$C NMR (101 MHz, DMSO) δ 155.24, 145.00, 132.54, 122.39, 120.64, 120.33, 118.02, 108.60, 87.97, 66.97, 61.42, 45.53, 40.14, 39.93, 39.72, 39.51, 39.30, 39.09, 38.88, 30.37, 24.57, 21.66.

Intermediate 6C

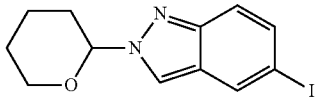 [SMILES: Ic1ccc2nn(C3CCCCO3)cc2c1]

5-iodo-2-(tetrahydro-2H-pyran-2-yl)-2H-indazole. 5-Iodoindazole (10 g, 41 mmol) was suspended in DCM, treated with PPTS (1.03 g, 4.1 mmol) and DHP (7.5 mL, 82 mmol) and allowed to stir overnight. TLC analysis indicates that a mixture of N1/N1 protected indazole has formed. The resulting homogenous solution was partitioned between half-saturated $NaHCO_3$ solution (~150 mL) and DCM. The combined organic layers were washed with brine, dried ($Na_2SO_4$), filtered and concentrated. The title product was the second eluting UV active spot isolated from the crude reaction mixture by column chromatography (Combiflash, 120 g column, 0-25% EtOAc/Heptane) and was 10.46 g of a yellow oil which crystalized upon standing (78%). $^1$H NMR (400 MHz, Chloroform-d) δ 8.09 (s, 1H), 8.07 (s, 1H), 7.49 (s, 2H), 5.66 (dd, J=8.9, 3.2 Hz, 1H), 4.22-4.06 (m, 1H), 3.78 (td, J=11.5, 10.9, 3.0 Hz, 1H), 2.28-2.11 (m, 2H), 2.11-1.98 (m, 1H), 1.85-1.62 (m, 4H).

Example 7

This example provides a description of synthesis of 3-(3-(pyridin-3-yl)-1H-indazol-5-yl)oxazolidin-2-one (7).

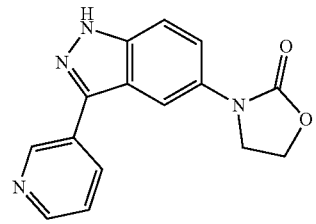 [SMILES: O=C1OCCN1c1ccc2[nH]nc(-c3cccnc3)c2c1]

3-(3-(pyridin-3-yl)-1H-indazol-5-yl)oxazolidin-2-one was prepared using the same procedure as Example 2 but substituting pyridine-3-boronic acid for benzofuran-2-boronic acid. (8.7 mg, 21%). $^1$H NMR (400 MHz, DMSO-d6) δ 13.48 (s, 1H), 9.18 (d, J=1.6 Hz, 1H), 8.62 (dd, J=4.7, 1.5 Hz, 1H), 8.34 (dt, J=7.9, 1.9 Hz, 1H), 8.06-8.00 (m, 1H), 7.81 (dd, J=9.1, 1.9 Hz, 1H), 7.66 (d, J=9.0 Hz, 1H), 7.56 (dd, J=7.9, 4.8 Hz, 1H), 4.50-4.44 (m, 2H), 4.25-4.16 (m, 2H).

Example 8

This example provides a description of synthesis of 3-(3-vinyl-1H-indazol-5-yl)oxazolidin-2-one (8).

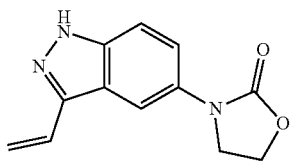 [SMILES: C=Cc1n[nH]c2ccc(N3CCOC3=O)cc12]

3-(3-vinyl-1H-indazol-5-yl)oxazolidin-2-one (8) was prepared using the same procedure as Example 6 Intermediate 6A substituting vinylboronic acid pinacol ester for phenylboronic acid (5.3 mg, 27%). $^1$H NMR (400 MHz, DMSO-d6) δ 13.13 (s, 1H), 7.95 (d, J=1.6 Hz, 1H), 7.74 (dd, J=9.1, 2.0 Hz, 1H), 7.56 (d, J=9.1 Hz, 1H), 7.03 (dd, J=18.0, 11.5 Hz, 1H), 6.03 (dd, J=18.0, 1.3 Hz, 1H), 5.47 (dd, J=11.5, 1.3 Hz, 1H), 4.56-4.35 (m, 2H), 4.27-4.02 (m, 2H).

Example 9

This example provides a description of synthesis of (E)-3-(3-styryl-1H-indazol-5-yl)oxazolidin-2-one (9).

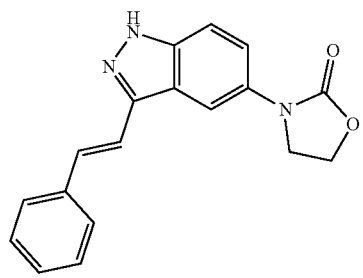 [SMILES: O=C1OCCN1c1ccc2[nH]nc(/C=C/c3ccccc3)c2c1]

A solution of Intermediate 6A (41 mg, 0.1 mmol), styrene (14 mg, 0.13 mmol) diisopropyethylamine (37 μL, 0.21 mmol) in 1 mL of anhydrous DMF in a pre-dried, flea bar equipped 1 dram vial was sparged for 2 min with $N_2$, treated with palladium (II) acetate (2.2 mg, 0.01 mmol) and tri-o-tolylphosphine (9 mg, 0.03 mmol) and sparged with $N_2$ for an additional minute. The vial was then sealed and heated to 100° C. The mixture was allowed to stir at this temperature overnight. The reaction was concentrated on to $SiO_2$ and purified on a Teledyne-ISCO Combiflash unit (4 g column, stepped gradient 0-50%-70% EtOAc/Heptane) to isolate 19.2 mg of a yellow solid. This was taken up in 1 mL THF and 1 mL 1.0 N HCl and allowed to stir for 2 hours. The mixture became a suspension which was filtered to isolate the desired product as 11 mg of an off-white solid (28%). $^1$H NMR 1H NMR (400 MHz, Chloroform-d) δ 10.12 (s, 1H), 7.99 (d, J=1.5 Hz, 1H), 7.76 (dd, J=9.0, 2.0 Hz, 1H), 7.61 (d, J=7.3 Hz, 2H), 7.52 (d, J=4.3 Hz, 1H), 7.49 (d, J=3.4 Hz, 1H), 7.45-7.37 (m, 3H), 7.31 (t, J=7.3 Hz, 1H), 4.60-4.51 (m, 2H), 4.23-4.15 (m, 2H).

Example 10

This example provides a description of synthesis of (E)-3-(3-(2-(pyridin-3-yl)vinyl)-1H-indazol-5-yl)oxazolidin-2-one (10).

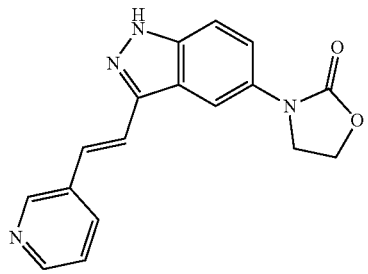 [SMILES: O=C1OCCN1c1ccc2[nH]nc(/C=C/c3cccnc3)c2c1]

(E)-3-(3-(2-(pyridin-3-yl)vinyl)-1H-indazol-5-yl)oxazolidin-2-one (10) was prepared using the same procedure as Example 9 but substituting 3-vinyl pyridine for styrene. After the acidic deprotection, the crude mixture was poured into 1 N NaOH to form a precipitate (ppt). This was collected by filtration to afford the title compound as 20.7 mg of a yellow solid (53%). $^1$H NMR (400 MHz, Chloroform-d) δ 10.19 (s, 1H), 8.81 (d, J=1.7 Hz, 1H), 8.54 (dd, J=4.7, 1.5 Hz, 1H), 8.03 (d, J=1.5 Hz, 1H), 7.93 (dt, J=7.9, 1.7 Hz, 1H), 7.76 (dd, J=9.0, 2.0 Hz, 1H), 7.53 (d, J=8.8 Hz, 1H), 7.48 (d, J=1.2 Hz, 2H), 7.34 (dd, J=7.7, 5.0 Hz, 1H), 4.66-4.52 (m, 2H), 4.32-4.14 (m, 2H).

Example 11

This example provides a description of synthesis of (E)-3-(3-(2-(pyridin-4-yl)vinyl)-1H-indazol-5-yl)oxazolidin-2-one (11).

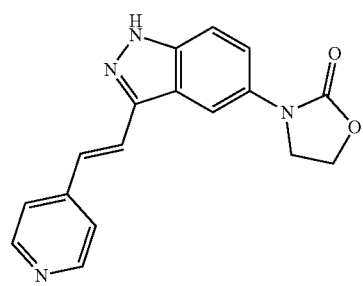 [SMILES: O=C1OCCN1c1ccc2[nH]nc(/C=C/c3ccncc3)c2c1]

(E)-3-(3-(2-(pyridin-4-yl)vinyl)-1H-indazol-5-yl)oxazolidin-2-one (11) was prepared using the same procedure as Example 9 but substituting 4-vinyl pyridine for styrene. After the acidic deprotection, the crude mixture was poured into 1 N NaOH to form a ppt. This was collected by filtration to afford the title compound as 15.4 mg of a yellow solid (39%). $^1$H NMR (600 MHz, DMSO-d6) δ 13.39 (s, 1H), 8.57 (d, J=6.0 Hz, 2H), 8.06 (d, J=1.7 Hz, 1H), 7.90-7.82 (m, 2H), 7.68 (d, J=6.1 Hz, 2H), 7.61 (d, J=9.1 Hz, 1H), 7.43 (d, J=16.6 Hz, 1H), 4.61-4.42 (m, 2H), 4.27-4.13 (m, 2H). $^{13}$C NMR (151 MHz, DMSO) δ 155.47, 149.99, 144.35, 141.39, 138.38, 132.82, 126.27, 124.66, 120.90, 120.80, 120.06, 110.92, 109.90, 61.51, 45.88.

Example 12

This example provides a description of synthesis of 3-(3-(pyridin-2-ylethynyl)-1H-indazol-5-yl)oxazolidin-2-one (12).

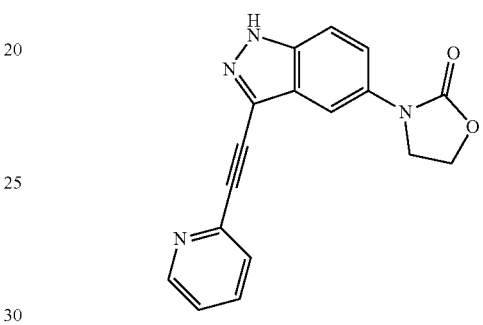

A mixture of Intermediate 6A (82 mg, 0.2 mmol) and 2-ethynylpyridine (24 µL, 0.24 mmol) in 1 mL trimethylamine and 1 mL of anhydrous DMF in a pre-dried, flea bar equipped 2 dram vial was sparged with $N_2$ for 3 minutes. After quickly adding CuI (1 mg, 0.004 mmol) and $PdCl_2(Ph_3P)_2$, the mixture was sparged again with $N_2$ for 1 minute. After quickly sealing the vial, the mixture was allowed to stir overnight at room temperature. The reaction mixture was concentrated directly on to $SiO_2$ and purified on a Teledyne-ISCO Combiflash unit (4 g column, 0-100% EtOAc/Heptane) to isolate a reddish-brown oil. The crude product was taken up in 1 mL THF and treated with 1 mL of 1N HCl and allowed to stir at RT for 3 hours forming a slurry. The mixture was filtered. The solid washed with a small amount of water to collect 25.3 mg of the title compound as the HCl salt (44%). $^1$H NMR (400 MHz, DMSO-d6) δ 8.68 (d, J=3.1 Hz, 1H), 8.01-7.91 (m, 1H), 7.90-7.75 (m, 3H), 7.69 (d, J=8.6 Hz, 1H), 7.56-7.44 (m, 1H), 4.51-4.45 (m, 2H), 4.25-4.11 (m, 2H).

Example 13

This example provides a description of synthesis of 3-(3-(pyridin-4-yl)-1H-indazol-5-yl)oxazolidin-2-one (13).

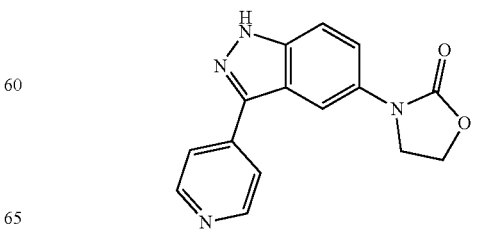

3-(3-(pyridin-4-yl)-1H-indazol-5-yl)oxazolidin-2-one (13) was prepared using the same procedure as Example 6 but substituting pyridine-4-boronic acid for phenyl boronic acid. After the deprotection (1:1 THF:1 N HCl) the crude reaction mixture was poured into 1 N NaOH and extracted twice with EtOAc. The combined organic layers were washed with brine, dried (Na$_2$SO$_4$), filtered, concentrated on to SiO2 and purified on a Teledyne-ISCO combiflash unit (4 g column, 0-10% MeOH/DCM) to afford the title compound as 9.1 mg of a white solid (38%). $^1$H NMR (400 MHz, DMSO-d6) δ 13.62 (s, 1H), 8.69 (d, J=6.1 Hz, 2H), 8.09 (d, J=1.8 Hz, 1H), 7.97 (d, J=6.1 Hz, 2H), 7.83 (dd, J=9.1, 2.0 Hz, 1H), 7.68 (d, J=9.1 Hz, 1H), 4.48 (dd, J=9.0, 6.9 Hz, 2H), 4.22 (dd, J=9.1, 6.9 Hz, 2H).

Example 14

This example provides a description of synthesis of 3-(3-(7-chloro-1H-indol-2-yl)-1H-indazol-5-yl)oxazolidin-2-one and 7-chloro-2-(4,4,5,5-tetramethyl-1,3,2-dioxaborolan-2-yl)-1H-indole.

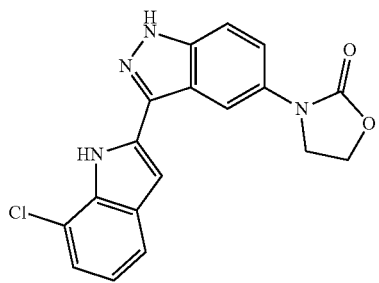 [SMILES: O=C1OCCN1c1ccc2[nH]nc(-c3cc4cccc(Cl)c4[nH]3)c2c1]

3-(3-(7-chloro-1H-indol-2-yl)-1H-indazol-5-yl)oxazolidin-2-one (14). Intermediate 6A (100 mg, 0.24 mmol), Intermediate 14A (101 mg 0.36 mmol), Pd(Ph$_3$P)$_4$ (12 mg, 0.011 mmol) were combined in a flea bar equipped 2 dram vial, taken up in 4 mL dioxane and treated with 1 mL of a suspension of LiCl/K$_3$PO$_4$ (1 M each in H$_2$O). The mixture was sparged with N$_2$ for 2 minutes, sealed, heated to 80° C. and allowed to stir overnight. The reaction mixture was cooled, poured into an 11 dram vial containing 15 mL EtOAc, shaken and dried by removing the water by pipet and adding Na$_2$SO$_4$. The crude organic layer was filtered and concentrated in vacuo. The crude residue was taken up in 2 mL THF and treated with 2 mL 0.1 N TSA$_{(aq)}$ and allowed to stir at rt for 1 hour. The reaction was then quenched with 3 mL of saturated, aqueous NaHCO$_3$ solution and partitioned between water and EtOAc. The combined organic layers were washed with brine, dried (Na$_2$SO$_4$), filtered, concentrated on to SiO$_2$ and purified through a 4 g column on a Teledyne-ISCO combiflash unit (0-1% MeOH/DCM). The resulting solid was stirred with DCM and filtered to afford the title compound as 18 mg of a white powder (21%). $^1$H NMR (600 MHz, DMSO-d6) δ 13.46 (s, 1H), 11.64 (s, 1H), 8.06 (s, 1H), 7.84 (d, J=8.8 Hz, 1H), 7.67 (d, J=8.9 Hz, 1H), 7.60 (d, J=7.6 Hz, 1H), 7.20 (d, J=7.4 Hz, 1H), 7.17 (s, 1H), 7.06 (t, J=7.5 Hz, 1H), 4.50 (t, J=7.7 Hz, 2H), 4.24 (t, J=7.7 Hz, 2H). $^{13}$CNMR (151 MHz, DMSO) δ 155.50, 138.40, 136.91, 133.45, 132.93, 132.82, 130.54, 121.43, 120.44, 120.16, 120.07, 119.01, 115.89, 110.95, 109.71, 101.34, 61.54, 45.81.

Intermediate 14A

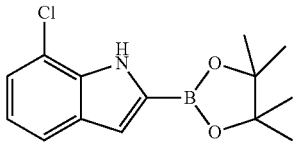 [SMILES: CC1(C)OB(c2cc3cccc(Cl)c3[nH]2)OC1(C)C]

7-chloro-2-(4,4,5,5-tetramethyl-1,3,2-dioxaborolan-2-yl)-1H-indole. Prepared according to a modified version of Ishiyama, et. al. (Angew. Chem. Int. Ed. 2002, 41, No. 16). In a pre-dried, flea bar equipped 2 dram vial, a solution of 7-Chloroindole (152 mg, 1.0 mmol) and bis(pinacolato)diboron (180 mg, 0.7 mmol) in 2 mL anhydrous dioxane was sparged with N$_2$ for 2 minutes. This mixture was quickly treated with (1,5-Cyclooctadiene)(methoxy)iridium(I) dimer (10 mg, 0.015 mmol) and 4,4'-di-tert-butyl-2,2'-bipyridine (8 mg, 0.03 mmol), sparged with N$_2$ for an additional 2 minutes, sealed and stirred at rt overnight. The crude reaction mixture was concentrated on to a small amount basic alumina and added to the top of an improvised basic alumina column (5 g ISCO sample cartridge approximately 2/3 full of basic alumina). This was eluted with 0-50% EtOAc/heptane on a Teledyne-ISCO combiflash unit to afford the title product as 115 mg of an oil (47%). $^1$H NMR (600 MHz, Chloroform-d) δ 8.73 (s, 1H), 7.57 (d, J=8.0 Hz, 1H), 7.24 (d, J=7.5 Hz, 1H), 7.14 (d, J=2.1 Hz, 1H), 7.04 (t, J=7.7 Hz, 1H), 1.39 (s, 12H).

Example 15

This example provides a description of synthesis of 3-(3-(6-chloro-1H-indol-2-yl)-1H-indazol-5-yl)oxazolidin-2-one and 6-chloro-2-(4,4,5,5-tetramethyl-1,3,2-dioxaborolan-2-yl)-1H-indole.

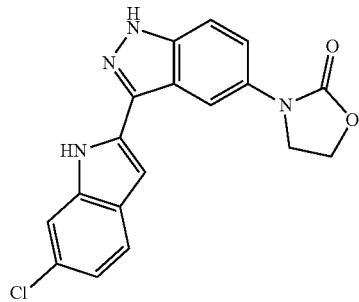 [SMILES: O=C1OCCN1c1ccc2[nH]nc(-c3cc4ccc(Cl)cc4[nH]3)c2c1]

3-(3-(6-chloro-1H-indol-2-yl)-1H-indazol-5-yl)oxazolidin-2-one (15). Prepared using the same procedure as Example 14 with Intermediate 6A and 2 equivalents of Intermediate 15A to afford Example 15 after chromatography (0-70% EtOAc/Heptane) as 38 mg of a white solid (45%). $^1$H NMR (600 MHz, DMSO-d6) δ 13.44 (s, 1H), 11.78 (s, 1H), 8.09 (s, 1H), 7.84 (d, J=8.6 Hz, 1H), 7.66 (d, J=9.1 Hz, 1H), 7.62 (d, J=8.4 Hz, 1H), 7.46 (s, 1H), 7.14 (s, 1H), 7.04 (d, J=7.9 Hz, 1H), 4.50 (t, J=8.0 Hz, 2H), 4.25 (t, J=7.9 Hz, 2H). $^{13}$C NMR (151 MHz, DMSO) δ 155.50, 138.49, 137.00, 136.87, 132.85, 132.48, 127.35, 126.14, 121.32, 120.12, 119.72, 119.54, 111.01, 110.94, 109.68, 99.59, 61.53, 45.83.

Intermediate 15A

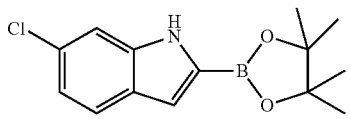 [SMILES: CC1(C)OB(c2cc3ccc(Cl)cc3[nH]2)OC1(C)C]

6-chloro-2-(4,4,5,5-tetramethyl-1,3,2-dioxaborolan-2-yl)-1H-indole. Prepared using the same procedure as Intermediate 14A with 6-chloroindole to afford the title product as 140 mg of a brown oil which crystalized upon standing (50%). $^1$H NMR (400 MHz, Chloroform-d) δ 8.52 (s, 1H), 7.57 (d, J=8.5 Hz, 1H), 7.39-7.36 (m, 1H), 7.10-7.03 (m, 2H), 1.37 (s, 12H).

Example 16

This example provides a description of synthesis of 3-(3-(6-chloro-1H-indol-2-yl)-1H-indazol-5-yl)oxazolidin-2-one and 5-chloro-2-(4,4,5,5-tetramethyl-1,3,2-dioxaborolan-2-yl)-1H-indole.

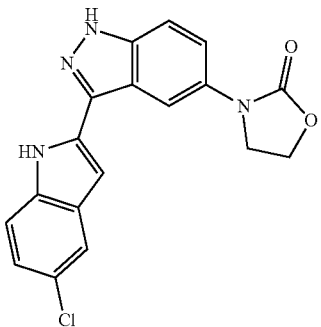 [SMILES: O=C1OCCN1c1ccc2[nH]nc(-c3cc4cc(Cl)ccc4[nH]3)c2c1]

3-(3-(6-chloro-1H-indol-2-yl)-1H-indazol-5-yl)oxazolidin-2-one (16). Prepared using the same procedure as Example 14 with Intermediate 6A and 2 eq of Intermediate 16A to afford Example 15 after chromatography (0-70% EtOAc/Heptane) as 49 mg of a white solid (58%). $^1$H NMR (600 MHz, DMSO-d6) δ 13.44 (s, 1H), 11.82 (s, 1H), 8.08 (d, J=2.0 Hz, 1H), 7.82 (dd, J=9.1, 2.0 Hz, 1H), 7.65 (d, J=9.0 Hz, 1H), 7.63 (d, J=2.1 Hz, 1H), 7.44 (d, J=8.5 Hz, 1H), 7.12 (dd, J=8.6, 2.1 Hz, 1H), 7.08 (d, J=2.1 Hz, 1H), 4.50 (t, J=7.9 Hz, 2H), 4.24 (dd, J=8.9, 6.9 Hz, 2H). $^{13}$C NMR (151 MHz, DMSO) δ 155.51, 138.48, 136.96, 134.94, 133.04, 132.86, 129.68, 123.71, 121.56, 120.13, 119.77, 119.01, 112.89, 111.03, 109.70, 99.16, 61.54.

Intermediate 16A

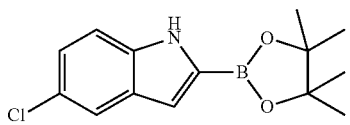 [SMILES: CC1(C)OB(c2cc3cc(Cl)ccc3[nH]2)OC1(C)C]

5-chloro-2-(4,4,5,5-tetramethyl-1,3,2-dioxaborolan-2-yl)-1H-indole. Prepared using the same procedure as Intermediate 14A with 5-chloroindole to afford the title product as 130 mg of a brown oil (47%). $^1$H NMR (400 MHz, Chloroform-d) δ 7.63 (dd, J=8.7, 2.0 Hz, 1H), 7.31 (dd, J=8.6, 5.3 Hz, 1H), 7.18 (dd, J=8.7, 1.9 Hz, 1H), 7.04 (d, J=2.1 Hz, 1H), 1.37 (s, 12H).

Example 17

This example provides a description of synthesis of 3-(3-(4-chloro-1H-indol-2-yl)-1H-indazol-5-yl)oxazolidin-2-one and 4-chloro-2-(4,4,5,5-tetramethyl-1,3,2-dioxaborolan-2-yl)-1H-indole.

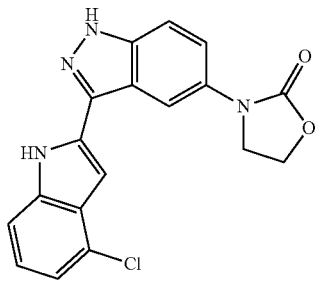 [SMILES: O=C1OCCN1c1ccc2[nH]nc(-c3cc4c(Cl)cccc4[nH]3)c2c1]

3-(3-(4-chloro-1H-indol-2-yl)-1H-indazol-5-yl)oxazolidin-2-one (17). Prepared using the same procedure as Example 14 with Intermediate 6A and 2 eq of Intermediate 17A. Purification of crude Example 17 was accomplished by chromatography (Teledyne ISCO, 4 g column, 0-100% EtOAc/Heptane) followed by triturating the resulting solid with DCM to provide pure product as 38 mg of a white solid (45%). $^1$H NMR (600 MHz, DMSO-d6) δ 13.49 (s, 1H), 12.00 (s, 1H), 8.16 (d, J=1.6 Hz, 1H), 7.80 (dd, J=9.0, 2.0 Hz, 1H), 7.67 (d, J=9.0 Hz, 1H), 7.44 (d, J=7.6 Hz, 1H), 7.15-7.09 (m, 2H), 7.06 (d, J=1.5 Hz, 1H), 4.59-4.44 (m, 2H), 4.32-4.16 (m, 2H). $^{13}$C NMR (151 MHz, DMSO) δ 155.57, 138.53, 137.27, 136.80, 132.90, 132.45, 127.02, 124.07, 122.48, 120.25, 119.77, 118.83, 111.06, 110.58, 109.85, 97.23, 61.57, 45.86.

Intermediate 17A

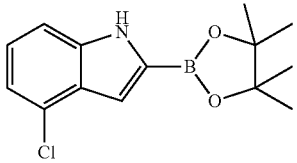 [SMILES: CC1(C)OB(c2cc3c(Cl)cccc3[nH]2)OC1(C)C]

4-chloro-2-(4,4,5,5-tetramethyl-1,3,2-dioxaborolan-2-yl)-1H-indole. Prepared using the same procedure as Intermediate 14A with 4-chloroindole to afford the title product as 177 mg of a colorless oil which crystalized upon standing (63%). $^1$H NMR (400 MHz, Chloroform-d) δ 8.68 (s, 1H), 7.29 (d, J=7.9 Hz, 1H), 7.24 (d, J=2.0 Hz, 1H), 7.15 (t, J=7.7 Hz, 1H), 7.10 (dd, J=7.5, 1.0 Hz, 1H), 1.38 (s, 12H).

Example 18

This example provides a description of synthesis of 3-(3-(7-methoxy-1H-indol-2-yl)-1H-indazol-5-yl)oxazolidin-2-one and 7-methoxy-2-(4,4,5,5-tetramethyl-1,3,2-dioxaborolan-2-yl)-1H-indole.

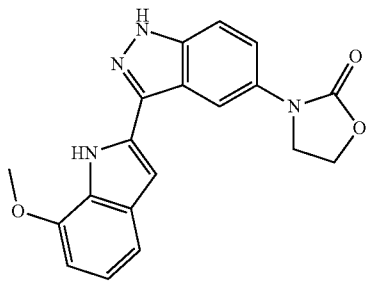 [SMILES: COc1cccc2cc(-c3n[nH]c4ccc(N5CCOC5=O)cc34)[nH]c12]

3-(3-(7-methoxy-1H-indol-2-yl)-1H-indazol-5-yl)oxazolidin-2-one (18). Prepared using the same procedure as Example 14 with Intermediate 6A and Intermediate 18A. The title product was obtained as 45 mg of a white solid (54%) after column chromatography (Teledyne ISCO combiflash, 4 g column, 0-75% EtOAc) and triturating the resulting solid in EtOAc/Heptane. $^1$H NMR (600 MHz, DMSO-d6) δ 13.32 (s, 1H), 11.26 (s, 1H), 8.05 (s, 1H), 7.80 (d, J=8.9 Hz, 1H), 7.62 (d, J=9.0 Hz, 1H), 7.21 (d, J=7.8 Hz, 1H), 7.02 (s, 1H), 6.97 (t, J=7.7 Hz, 1H), 6.70 (d, J=7.6 Hz, 1H), 4.48 (t, J=7.9 Hz, 2H), 4.23 (t, J=7.9 Hz, 2H), 3.93 (s, 3H). $^{13}$C NMR (151 MHz, DMSO) δ 155.51, 146.20, 138.36, 137.49, 132.55, 131.33, 130.00, 126.62, 120.06, 119.97, 119.94, 112.83, 110.79, 109.93, 102.50, 100.73, 61.53, 55.28, 45.84.

Intermediate 18A

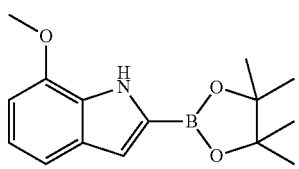 [SMILES: COc1cccc2cc(B3OC(C)(C)C(C)(C)O3)[nH]c12]

7-methoxy-2-(4,4,5,5-tetramethyl-1,3,2-dioxaborolan-2-yl)-1H-indole. Prepared using the same procedure as Intermediate 14A with 7-methoxyindole to afford the title product as 160 mg of an orange oil which crystalized upon standing (60%). $^1$H NMR (600 MHz, Chloroform-d) δ 8.80 (s, 1H), 7.29-7.26 (m, 1H), 7.09 (d, J=2.2 Hz, 1H), 7.03-6.99 (m, 1H), 6.66 (d, J=7.4 Hz, 1H), 3.96 (s, 3H), 1.37 (s, 12H).

Example 19

This example provides a description of synthesis of 3-(3-(6-methoxy-1H-indol-2-yl)-1H-indazol-5-yl)oxazolidin-2-one and 6-methoxy-2-(4,4,5,5-tetramethyl-1,3,2-dioxaborolan-2-yl)-1H-indole.

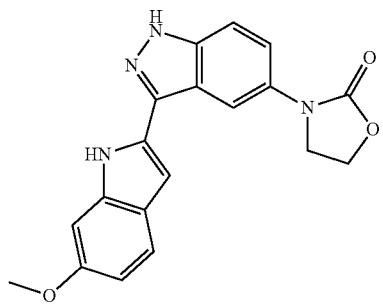 [SMILES: COc1ccc2cc(-c3n[nH]c4ccc(N5CCOC5=O)cc34)[nH]c2c1]

3-(3-(6-methoxy-1H-indol-2-yl)-1H-indazol-5-yl)oxazolidin-2-one (19). Prepared using the same procedure as Example 14 with Intermediate 6A and Intermediate 19A. The title product was obtained as 36 mg of a tan powder (43%) after column chromatography (Teledyne ISCO combiflash, 4 g column, 0-75% EtOAc) and triturating the resulting solid in EtOAc/Heptane. $^1$H NMR (600 MHz, DMSO-d6) δ 13.26 (s, 1H), 11.41 (s, 1H), 8.10-8.05 (m, 1H), 7.80 (dd, J=9.0, 2.0 Hz, 1H), 7.62 (d, J=9.0 Hz, 1H), 7.47 (d, J=8.6 Hz, 1H), 7.03-6.98 (m, 1H), 6.96 (d, J=2.0 Hz, 1H), 6.68 (dd, J=8.6, 2.3 Hz, 1H), 4.61-4.40 (m, 2H), 4.30-4.16 (m, 2H), 3.79 (s, 3H). $^{13}$C NMR (151 MHz, DMSO) δ 155.92, 155.52, 138.48, 137.67, 137.31, 132.53, 130.25, 122.75, 120.60, 119.99, 119.58, 110.83, 109.93, 109.47, 99.59, 94.43, 61.52, 55.12, 45.85.

Intermediate 19A

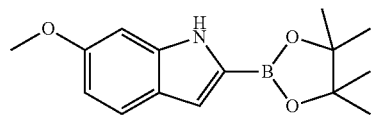

6-methoxy-2-(4,4,5,5-tetramethyl-1,3,2-dioxaborolan-2-yl)-1H-indole. Prepared using the same procedure as Intermediate 14A with 6-methoxyindole to afford the title product as 154 mg of white solid (56%). $^1$H NMR (600 MHz, Chloroform-d) δ 8.42 (s, 1H), 7.53 (d, J=8.7 Hz, 1H), 7.06 (dd, J=2.0, 0.9 Hz, 1H), 6.83 (d, J=2.1 Hz, 1H), 6.78 (dd, J=8.7, 2.2 Hz, 1H), 3.86 (s, 3H), 1.37 (s, 12H).

Example 20

This example provides a description of synthesis of 3-(3-(5-methoxy-1H-indol-2-yl)-1H-indazol-5-yl)oxazolidin-2-one and 5-methoxy-2-(4,4,5,5-tetramethyl-1,3,2-dioxaborolan-2-yl)-1H-indole.

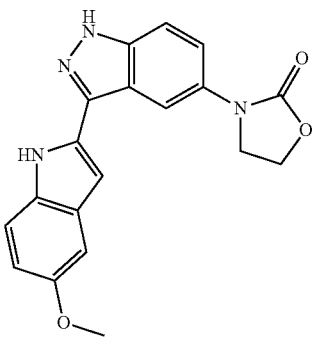 [SMILES: COc1ccc2[nH]c(-c3n[nH]c4ccc(N5CCOC5=O)cc34)cc2c1]

3-(3-(5-methoxy-1H-indol-2-yl)-1H-indazol-5-yl)oxazolidin-2-one (20). Prepared using the same procedure as Example 14 with Intermediate 6A and Intermediate 20A. The title product was obtained as 24 mg of a white solid (29%) after column chromatography (Teledyne ISCO combiflash, 4 g column, 0-75% EtOAc) and triturating the resulting solid in EtOAc/Heptane. $^1$H NMR (600 MHz, DMSO-d6) δ 13.33 (s, 1H), 11.43 (s, 1H), 8.10 (s, 1H), 7.81 (dd, J=9.0, 1.9 Hz, 1H), 7.64 (d, J=9.0 Hz, 1H), 7.34 (d, J=8.7 Hz, 1H), 7.13-7.09 (m, 1H), 7.01 (d, J=1.5 Hz, 1H), 6.77 (dd, J=8.7, 2.4 Hz, 1H), 4.58-4.39 (m, 2H), 4.32-4.18

(m, 2H), 3.78 (s, 3H). $^{13}$C NMR (151 MHz, DMSO) δ 155.50, 153.51, 138.44, 137.56, 132.65, 131.85, 131.59, 128.85, 119.92, 119.76, 112.10, 111.81, 110.90, 109.75, 101.61, 99.48, 61.52, 55.26, 45.80.

Intermediate 20A

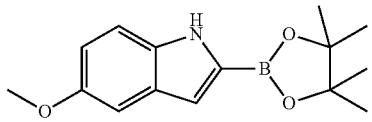

5-methoxy-2-(4,4,5,5-tetramethyl-1,3,2-dioxaborolan-2-yl)-1H-indole. Prepared using the same procedure as Intermediate 14A with 5-methoxyindole to afford the title product as 133 mg of light-brown oil (49%). $^1$H NMR (600 MHz, Chloroform-d) δ 8.45 (s, 1H), 7.29 (s, 1H), 7.09 (d, J=2.5 Hz, 1H), 7.05-7.02 (m, 1H), 6.92 (dd, J=8.8, 2.4 Hz, 1H), 3.86 (s, 3H), 1.37 (s, 12H).

Example 21

This example provides a description of synthesis of 3-(3-(4-methoxy-1H-indol-2-yl)-1H-indazol-5-yl)oxazolidin-2-one and 4-methoxy-2-(4,4,5,5-tetramethyl-1,3,2-dioxaborolan-2-yl)-1H-indole.

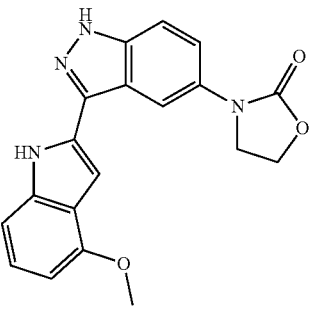 [SMILES: COc1cccc2[nH]c(-c3n[nH]c4ccc(N5CCOC5=O)cc34)cc12]

3-(3-(4-methoxy-1H-indol-2-yl)-1H-indazol-5-yl)oxazolidin-2-one (21). Prepared using the same procedure as Example 14 with Intermediate 6A and Intermediate 21A. The title product was obtained as 32 mg of a white solid (38%) after column chromatography (Teledyne ISCO combiflash, 4 g column, 0-75% EtOAc) and triturating the resulting solid in EtOAc/Heptane. $^1$H NMR (600 MHz, DMSO-d6) δ 13.33 (s, 1H), 11.61 (s, 1H), 8.14 (s, 1H), 7.76 (dd, J=9.0, 1.8 Hz, 1H), 7.64 (d, J=9.0 Hz, 1H), 7.10-7.00 (m, 3H), 6.54 (d, J=7.2 Hz, 1H), 4.58-4.41 (m, 2H), 4.34-4.15 (m, 2H), 3.92 (s, 3H). $^{13}$C NMR (151 MHz, DMSO) δ 155.56, 152.70, 138.49, 137.73, 137.48, 132.62, 129.88, 122.59, 120.03, 119.69, 118.99, 110.87, 109.97, 104.92, 99.21, 96.74, 61.56, 54.85, 45.87.

Intermediate 21A

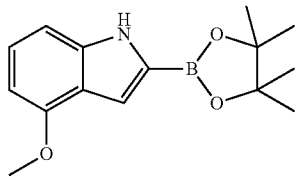 [SMILES: COc1cccc2[nH]c(B3OC(C)(C)C(C)(C)O3)cc12]

4-methoxy-2-(4,4,5,5-tetramethyl-1,3,2-dioxaborolan-2-yl)-1H-indole. Prepared using the same procedure as Intermediate 14A with 4-methoxyindole to afford the title product as 129 mg of white solid (47%). $^1$H NMR (600 MHz, Chloroform-d) δ 8.52 (s, 1H), 7.25-7.21 (m, 1H), 7.15 (t, J=7.9 Hz, 1H), 7.00 (d, J=8.2 Hz, 1H), 6.48 (d, J=7.7 Hz, 1H), 3.96 (s, 3H), 1.36 (s, 12H).

Example 22

This example provides a description of synthesis of 3-(3-(1H-pyrrol-2-yl)-1H-indazol-5-yl)oxazolidin-2-one (22).

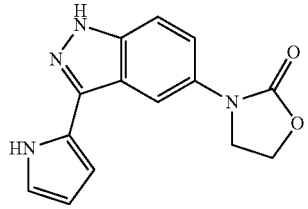

Intermediate 6A (124 mg, 0.3 mmol), N—BOC-pyrrole-2-boronic acid (190 mg, 0.9 mmol), Pd(Ph$_3$P)$_4$ (10.4 mg, 0.01 mmol) were combined in a flea bar equipped 2 dram vial and taken up in 4 mL dioxane. This mixture was treated with 1 mL of a suspension of LiCl/K$_3$PO$_4$ (1.0M each in water) and sparged with N$_2$ for 2 minutes. The vial was then sealed, heated to 80° C. and the mixture was stirred for 5 hours. The reaction was cooled, diluted with EtOAc, treated with Na$_2$SO$_4$, filtered, concentrated on to SiO$_2$ and purified on an Teledyne-ISCO Combiflash unit (4 g column, 0-50% EtOAc/Heptane) to isolate 119 mg of a white solid. This material was a mixture of indazole-2-THP/N-BOC pyrrole atropisomers by HNMR. A sample of 50 mg of this material was taken up in 0.5 mL DCM, treated with triisopropylsilane (275 μL, 10 eq) and trifluoroacetic acid (0.5 mL) and allowed to stir 30 minutes. The reaction mixture was quenched with saturated aqueous NaHCO$_3$ solution, and diluted with EtOAc. The water was removed by pipet and the organic layer was dried (Na$_2$SO$_4$), filtered, concentrated on to basic alumina and purified on a Teledyne-ISCO Combiflash unit (4 g column, 0-70% EtOAc/Heptane) to afford the title product as 19 mg of a white powder (64%). $^1$HNMR (600 MHz, DMSO-d6) δ 12.98 (s, 1H), 11.35 (s, 1H), 7.96 (s, 1H), 7.74 (dd, J=9.0, 1.9 Hz, 1H), 7.56 (d, J=9.0 Hz, 1H), 6.86 (s, 1H), 6.68 (s, 1H), 6.20 (q, J=2.5 Hz, 1H), 4.56-4.39 (m, 2H), 4.27-4.13 (m, 2H). $^{13}$C NMR (151 MHz, DMSO) δ 155.49, 138.33, 138.27, 132.00, 124.78, 119.76, 119.14, 118.85, 110.51, 110.06, 108.55, 106.62, 61.47, 45.80.

Example 23

This example provides a description of synthesis of 3-(3-(3-chlorophenyl)-1H-indazol-5-yl)oxazolidin-2-one (23).

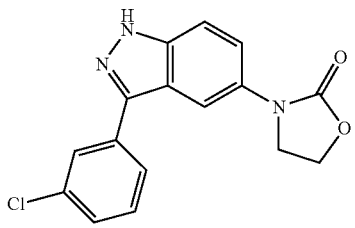 [SMILES: O=C1OCCN1c1ccc2[nH]nc(-c3cccc(Cl)c3)c2c1]

Intermediate 6A (124 mg, 0.3 mmol), 3-chlorophenylboronic acid (56 mg, 0.36 mmol), Pd(Ph$_3$P)$_4$ (7 mg, 0.006 mmol) were combined in a flea bar equipped 2 dram vial and taken up 4 mL dioxane. After adding a 1 mL of an aqueous suspension of LiCl/K$_3$PO$_4$ (1M each), the mixture was sparged with N$_2$ for 2 minutes. The vial was sealed, heated to 80° C. and allowed to stir overnight. The reaction mixture was cooled, diluted with EtOAc, treated with Na$_2$SO$_4$, filtered and concentrated. The crude residue was taken up in 1 mL THF and 1 mL 0.1N toluenesulfonic acid and allowed to stir at rt for 2 hours. The mixture was subsequently diluted with EtOAc, quenched with 0.5 mL saturated, aqueous Na$_2$CO$_3$ solution and dried by first removing the aqueous layer by pipet then adding Na$_2$SO$_4$. The mixture was filtered, concentrated on to SiO$_2$ and purified on a Teledyne-ISCO Combiflash unit (4 g column, 0-50% EtOAC/Heptane) to afford Example 23 as 52 mg of a white solid (55%). $^1$H NMR (600 MHz, DMSO-d6) δ 13.40 (s, 1H), 8.05 (s, 1H), 7.98-7.92 (m, 2H), 7.76 (dd, J=9.0, 1.9 Hz, 1H), 7.65 (d, J=8.9 Hz, 1H), 7.57 (t, J=7.8 Hz, 1H), 7.50-7.46 (m, 1H), 4.54-4.39 (m, 2H), 4.27-4.14 (m, 2H). $^{13}$C NMR (151 MHz, DMSO) δ 155.42, 141.62, 138.72, 135.63, 133.57, 132.84, 130.76, 127.39, 125.93, 125.12, 119.89, 119.67, 111.00, 109.70, 61.42, 45.73.

Example 24

This example provides a description of synthesis of 3-(3-(4-chlorophenyl)-1H-indazol-5-yl)oxazolidin-2-one (24).

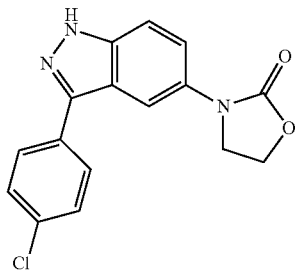 [SMILES: O=C1OCCN1c1ccc2[nH]nc(-c3ccc(Cl)cc3)c2c1]

Prepared using the same procedure as Example 23 with Intermediate 6A and 4-chlorophenylboronic acid to afford Example 24 as 61 mg of a white solid (65%). $^1$H NMR (600 MHz, DMSO-d6) δ 13.34 (s, 1H), 8.02 (s, 1H), 8.01-7.97 (m, 2H), 7.77 (dd, J=9.0, 2.0 Hz, 1H), 7.64 (d, J=9.4 Hz, 1H), 7.61-7.56 (m, 2H), 4.48 (dd, J=8.8, 7.2 Hz, 2H), 4.19 (dd, J=8.9, 7.1 Hz, 2H). $^{13}$C NMR (151 MHz, DMSO) δ 155.98, 142.52, 139.29, 133.29, 132.99, 132.72, 129.40, 128.77, 120.43, 120.23, 111.51, 110.40, 61.98, 46.33.

Example 25

This example provides a description of synthesis of 3-(3-(naphthalen-2-yl)-1H-indazol-5-yl)oxazolidin-2-one (25).

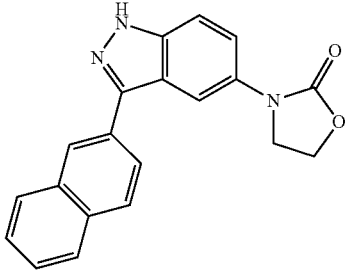 [SMILES: O=C1OCCN1c1ccc2[nH]nc(-c3ccc4ccccc4c3)c2c1]

Prepared using the same procedure as Example 23 with Intermediate 6A and naphthyl-2-boronic acid to afford Example 25 as 67 mg of a white solid (68%). $^1$HNMR (600 MHz, DMSO-d6) δ 13.35 (s, 1H), 8.50 (s, 1H), 8.22-8.19 (m, 1H), 8.17 (dd, J=8.5, 1.6 Hz, 1H), 8.09 (d, J=7.9 Hz, 1H), 8.06 (d, J=8.6 Hz, 1H), 7.97 (d, J=7.8 Hz, 1H), 7.80 (dd, J=9.0, 2.0 Hz, 1H), 7.67 (d, J=9.0 Hz, 1H), 7.60-7.53 (m, 2H), 4.49 (dd, J=8.9, 7.1 Hz, 2H), 4.24 (dd, J=8.9, 7.1 Hz, 2H). $^{13}$C NMR (151 MHz, DMSO) δ 155.48, 143.02, 138.86, 133.18, 132.66, 132.33, 131.13, 128.29, 128.10, 127.51, 126.32, 126.05, 125.03, 124.93, 119.99, 119.94, 110.90, 110.32, 61.44, 45.81, 39.93, 39.79, 39.65, 39.51, 39.37, 39.23, 39.09.

Example 26

This example provides a description of synthesis of 3-(3-([1,1'-biphenyl]-3-yl)-1H-indazol-5-yl)oxazolidin-2-one (26).

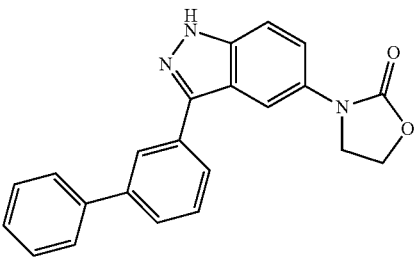 [SMILES: O=C1OCCN1c1ccc2[nH]nc(-c3cccc(-c4ccccc4)c3)c2c1]

Prepared using the same procedure as Example 23 with Intermediate 6A and 3-biphenyl-boronic acid to afford Example 26 as 55 mg of a tan solid (52%). $^1$HNMR (600 MHz, DMSO-d6) δ 13.30 (s, 1H), 8.19 (t, J=1.4 Hz, 1H), 8.15 (d, J=1.6 Hz, 1H), 7.96 (d, J=7.6 Hz, 1H), 7.77 (d, J=7.2 Hz, 2H), 7.74-7.69 (m, 2H), 7.67-7.62 (m, 2H), 7.52 (t, J=7.7 Hz, 2H), 7.42 (t, J=7.4 Hz, 1H), 4.61-4.39 (m, 2H), 4.29-4.14 (m, 2H). $^{13}$C NMR (151 MHz, DMSO) δ 155.98, 143.65, 141.36, 140.58, 139.25, 134.77, 133.17, 130.08, 129.50, 128.11, 127.28, 126.62, 126.32, 125.41, 120.48, 120.15, 111.46, 110.35, 61.97, 46.23, 40.50, 40.36, 40.22, 40.08, 39.94, 39.80, 39.66.

Example 27

This example provides a description of synthesis of 3-(3-([1,1'-biphenyl]-4-yl)-1H-indazol-5-yl)oxazolidin-2-one (27).

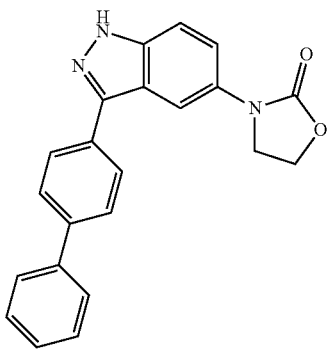 [SMILES: O=C1OCCN1c1ccc2[nH]nc(-c3ccc(-c4ccccc4)cc3)c2c1]

Prepared using the same procedure as Example 23 with Intermediate 6A and 4-biphenyl-boronic acid to afford Example 27 as 41 mg of a tan solid (38%). $^1$H NMR (600 MHz, DMSO-d6) δ 13.29 (s, 1H), 8.13-8.10 (m, 1H), 8.08 (d, J=8.3 Hz, 2H), 7.84 (d, J=8.4 Hz, 2H), 7.76 (dd, J=9.0, 1.8 Hz, 3H), 7.65 (d, J=9.0 Hz, 1H), 7.51 (t, J=7.7 Hz, 2H), 7.40 (t, J=7.4 Hz, 1H), 4.57-4.35 (m, 2H), 4.27-4.11 (m, 2H). $^{13}$C NMR (151 MHz, DMSO) δ 156.00, 143.29, 140.18, 139.78, 139.31, 133.27, 133.16, 129.47, 128.00, 127.63, 127.60, 127.03, 120.44, 120.30, 111.45, 110.61, 61.98, 46.34.

Example 28

This example provides a description of synthesis of 3-(3-(1H-indol-6-yl)-1H-indazol-5-yl)oxazolidin-2-one (28).

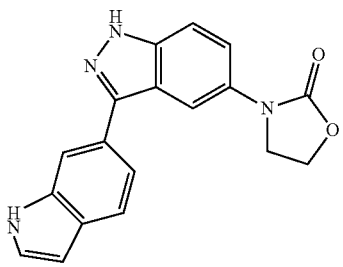 [SMILES: O=C1OCCN1c1ccc2[nH]nc(-c3ccc4cc[nH]c4c3)c2c1]

Prepared using the same procedure as Example 23 with Intermediate 6A and indole-6-boronic acid to afford Example 28 as 7 mg of a brown solid (7%). $^1$H NMR (600 MHz, DMSO-d6) δ 13.02 (s, 1H), 11.16 (s, 1H), 8.12-8.06 (m, 2H), 7.73-7.67 (m, 2H), 7.60 (d, J=8.9 Hz, 1H), 7.54 (d, J=8.4 Hz, 1H), 7.42-7.38 (m, 1H), 6.56-6.52 (m, 1H), 4.47 (dd, J=8.9, 7.1 Hz, 2H), 4.19 (dd, J=8.9, 7.1 Hz, 2H).

Example 29

This example provides a description of synthesis of (E)-N-(2-(dimethylamino)ethyl)-3-(2-(5-(2-oxooxazolidin-3-yl)-1H-indazol-3-yl)vinyl)benzamide and (E)-3-(2-(5-(2-Oxooxazolidin-3-yl)-1H-indazol-3-yl)vinyl)benzoic acid.

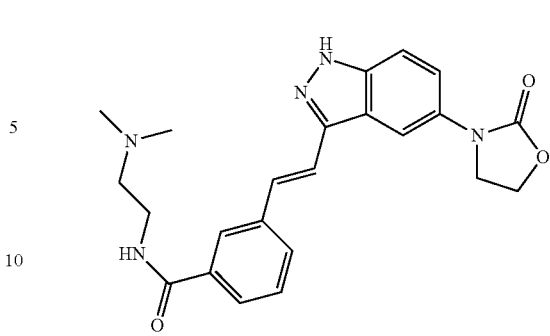

(E)-N-(2-(dimethylamino)ethyl)-3-(2-(5-(2-oxooxazolidin-3-yl)-1H-indazol-3-yl)vinyl)benzamide (29). Intermediate 29A (26 mg, 0.07 mmol), N,N-dimethylaminoethylene diamine (15 μL, 0.14 mmol), HOBt (15 mg, 0.11 mmol) and DIPEA (61 μL, 0.35 mmol) were combined in a 1 dram vial and dissolved in 1 mL anhydrous DMF. The mixture was treated with EDC.HCl (27 mg, 0.14 mmol) and allowed to stir overnight. The reaction was concentrated in vacuo and purified by prep TLC (10% 7N NH$_3$ in MeOH/DCM). The resulting material was purified a second time by prep TLC (10% MeOH/DCM, 3 elutions) to isolate 12.5 mg of the title compound as a white solid (8%). $^1$H NMR (600 MHz, DMSO-d6) δ 13.32 (s, 1H), 12.92 (s, 1H), 8.07 (s, 1H), 7.96 (d, J=8.3 Hz, 2H), 7.87-7.82 (m, 3H), 7.73 (d, J=16.6 Hz, 1H), 7.61 (d, J=9.0 Hz, 1H), 7.53 (d, J=16.6 Hz, 1H), 4.59-4.41 (m, 2H), 4.29-4.12 (m, 2H).

Intermediate 29A

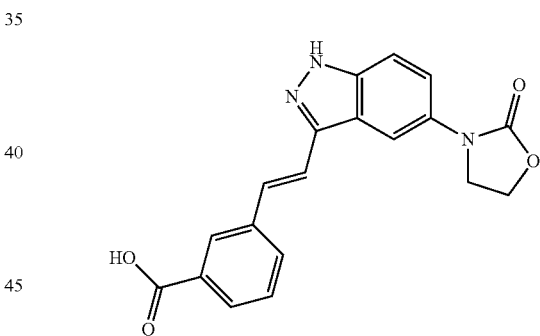

(E)-3-(2-(5-(2-Oxooxazolidin-3-yl)-1H-indazol-3-yl)vinyl)benzoic acid. A solution of Intermediate 6A (150 mg, 0.36 mmol), 3-vinylbenzoic acid (75 mg, 0.51 mmol), 1 mL trimethylamine in 1 mL anhydrous DMF in a pre-dried, flea bar equipped 2 dram vial was sparged with N$_2$ for 2 minutes and quickly treated with palladium (II) acetate (8 mg, 0.036 mmol) and tri-o-tolylphosphine (12 mg, 0.11 mmol). After sparging this mixture for an additional 2 minutes, the vial was sealed and heated to 100° C. The mixture was allowed to stir at this temperature overnight. The cooled crude mixture was poured in to ~3 mL 1 N NaOH and extracted with EtOAc. The organic layer was washed with an additional 2 mL of 1 N NaOH and discarded. The combined aqueous layers were acidified with 6N HCl and extracted with 10 mL EtOAc. The organic layer was dried (Na$_2$SO$_4$), filtered and concentrated on to SiO$_2$ and purified on a Teledyne-ISCO combiflash unit (4 g column, 0-5% MeOH/DCM) to isolate about 50 mg of a yellow solid which by $^1$H NMR was a mixture of the THP protected and de-protected material. The mixture was taken up in 1 mL THF and treated with 1 mL 0.1 N aqueous p-toluenesulfonic acid (p-TSA$_{aq}$) and stirred for 1 hour at RT. The resulting tan slurry was collected by filtration and used without further characterization or purification.

Example 30

This example provides a description of synthesis of (E)-N-(2-(dimethylamino)ethyl)-4-(2-(5-(2-oxooxazolidin-3-yl)-1H-indazol-3-yl)vinyl)benzamide and E)-4-(2-(5-(2-Oxooxazolidin-3-yl)-1H-indazol-3-yl)vinyl)benzoic acid.

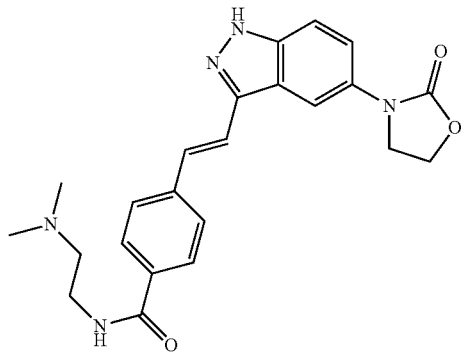 [SMILES: CN(C)CCNC(=O)c1ccc(/C=C/c2n[nH]c3ccc(N4CCOC4=O)cc23)cc1]

(E)-N-(2-(dimethylamino)ethyl)-4-(2-(5-(2-oxooxazolidin-3-yl)-1H-indazol-3-yl)vinyl)benzamide (30). 30 was prepared using the same procedure as Example 29; however, an aqueous/EtOAc work-up was performed after the amide coupling step. Purification was by prep TLC, requiring two elutions in 10% MeOH/DCM to separate the desired product as 5 mg of a white solid (3%). $^1$HNMR (600 MHz, DMSO-d6) δ 13.28 (s, 1H), 8.41 (t, J=5.7 Hz, 1H), 8.07 (s, 1H), 7.88 (d, J=8.4 Hz, 2H), 7.84 (dd, J=9.0, 2.0 Hz, 1H), 7.80 (d, J=8.4 Hz, 2H), 7.69 (d, J=16.6 Hz, 1H), 7.60 (d, J=9.0 Hz, 1H), 7.51 (d, J=16.6 Hz, 1H), 4.54-4.47 (m, 2H), 4.25-4.20 (m, 2H), 3.40-3.35 (m, 2H), 2.42 (t, J=6.9 Hz, 2H), 2.19 (s, 6H).

Intermediate 30A

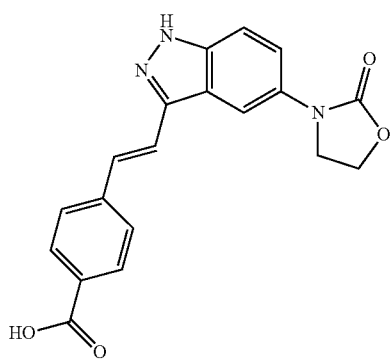 [SMILES: O=C(O)c1ccc(/C=C/c2n[nH]c3ccc(N4CCOC4=O)cc23)cc1]

(E)-4-(2-(5-(2-Oxooxazolidin-3-yl)-1H-indazol-3-yl)vinyl)benzoic acid. Intermediate 30A was prepared using the same procedure as Intermediate 29A but substituting 4-vinylbenzoic acid for 3-vinylbenzoic acid. $^1$H NMR (600 MHz, DMSO-d6) δ 13.32 (s, 1H), 12.92 (s, 1H), 8.07 (s, 1H), 7.96 (d, J=8.3 Hz, 2H), 7.87-7.82 (m, 3H), 7.73 (d, J=16.6 Hz, 1H), 7.61 (d, J=9.0 Hz, 1H), 7.53 (d, J=16.6 Hz, 1H), 4.59-4.41 (m, 2H), 4.29-4.12 (m, 2H).

Example 31

This example provides a description of synthesis of (E)-3-(3-(4-methoxystyryl)-1H-indazol-5-yl)oxazolidin-2-one (31).

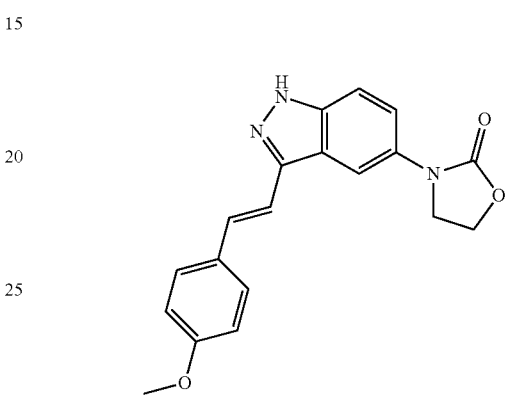

A solution of Intermediate 6A (150 mg, 0.36 mmol), 4-methoxystyrene (68 mg, 0.51 mmol), 1 mL trimethylamine in 1 mL anhydrous DMF in a pre-dried, flea bar equipped 2 dram vial was sparged with N$_2$ for 2 minutes and quickly treated with palladium (II) acetate (8 mg, 0.036 mmol) and tri-o-tolylphosphine (12 mg, 0.11 mmol). After sparging this mixture for an additional 2 minutes, the vial was sealed and heated to 100 C. The mixture was allowed to stir at this temperature overnight. The cooled reaction was poured into 20 mL water and extracted twice with 10 mL EtOAc. The combined organic layers were washed with water (3×10 mL), brine (1×10 mL), dried (Na$_2$SO$_4$), filtered and concentrated on to SiO$_2$ and purified by chromatography (Teledyne-ISCO Combiflash, 4 g column, 0-50%-70% EtOAc/Heptane) to obtain approximately 100 mg of a solid. This was dissolved in 1 mL THF and 1 mL p-TSA$_{(aq)}$ and allowed to stir for 1 hour. The reaction mixture was diluted with 20 mL EtOAc, poured into 1N NaOH and shaken. The organic layer was washed with brine, dried (Na$_2$SO$_4$), filtered, concentrated on to SiO$_2$ and purified using a Teledyne-ISCO Combiflash unit (4 g Column, 0-50%-70% EtOAc/Heptane) to isolate the title compound as 13 mg of a white solid (11%). $^1$H NMR (600 MHz, DMSO-d6) δ 13.12 (s, 1H), 8.04 (s, 1H), 7.80 (d, J=9.0 Hz, 1H), 7.65 (d, J=8.7 Hz, 2H), 7.57 (d, J=9.0 Hz, 1H), 7.41 (s, 2H), 6.98 (d, J=8.8 Hz, 2H), 4.53-4.46 (m, 2H), 4.24-4.17 (m, 2H), 3.80 (s, 3H). $^{13}$C NMR (151 MHz, DMSO) δ 159.00, 142.36, 138.40, 132.26, 129.76, 128.80, 127.75, 120.54, 119.89, 117.90, 114.17, 110.65, 110.18, 61.49, 55.17, 45.91, 39.51.

Example 32

This example provides a description of synthesis of 2-(3-(1H-indol-2-yl)-1H-indazol-5-yl)isothiazolidine 1,1-dioxide (32).

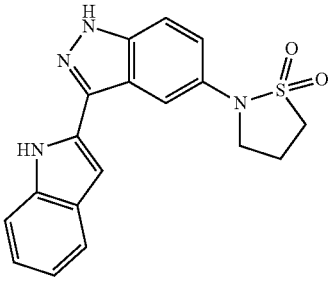 [SMILES: O=S1(=O)CCCN1c1ccc2[nH]nc(-c3cc4ccccc4[nH]3)c2c1]

Intermediate 32A (70 mg, 0.13 mmol), 1,3-propanesultam (23 mg, 0.19 mmol), copper (I) iodide (5 mg, 0.026 mmol) and $K_3PO_4$ (55 mg, 0.26 mmol) were combined in a pre-dried, flea bar equipped 2 dram vial and taken up in 1 mL anhydrous dioxane. This mixture was sparged with $N_2$ for 2 minutes and treated with trans-N,N'-dimethylaminocyclohexane-1,2-diamine (8 μL, 0.052 mmol). After an additional 2 minutes of $N_2$-sparging, the vial was sealed, heated to 110° C. overnight. The reaction mixture was cooled, diluted with EtOAc, washed three times with 5 mL water, dried ($Na_2SO_4$), filtered and concentrated to a white foam. Remaining traces of dioxane were removed after drying overnight under high vacuum. After dissolving in 2 mL DCM, the crude solid was treated with triisopropylsilane (266 μL, 1.30 mmol) followed by 2 mL trifluoroacetic acid and allowed to stir for 2 hours at rt. This mixture was quenched with saturated, aqueous NaHCO3 and partitioned between EtOAc and water. The combined organic layers were washed with brine, dried ($Na_2SO_4$), filtered and concentrated on to $SiO_2$. The desired product was isolated after chromatography (Teledyne-ISCO Combiflash, 4 g column, 0-60% EtOAc/heptane) as 26 mg of a tan solid (57%). $^1$H NMR (600 MHz, DMSO-d6) δ 13.39 (s, 1H), 11.60 (s, 1H), 7.88-7.84 (m, 1H), 7.64 (d, J=8.9 Hz, 1H), 7.61 (d, J=7.8 Hz, 1H), 7.49-7.43 (m, 2H), 7.12 (t, J=7.5 Hz, 1H), 7.09-7.07 (m, 1H), 7.02 (t, J=7.4 Hz, 1H), 3.91 (t, J=6.5 Hz, 2H), 3.54 (t, J=7.5 Hz, 2H), 2.46 (p, J=6.7 Hz, 2H). $^{13}$C NMR (151 MHz, DMSO) δ 139.03, 137.43, 136.46, 131.89, 131.28, 128.50, 121.76, 121.67, 120.07, 120.02, 119.22, 111.65, 111.48, 111.34, 99.63, 47.86, 47.72, 18.55.

Intermediate 32A

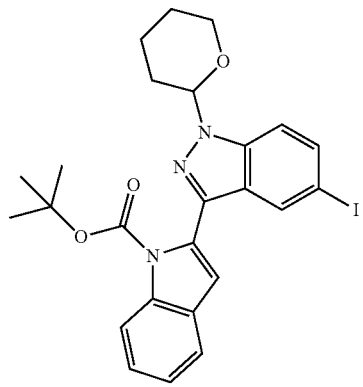 [SMILES: CC(C)(C)OC(=O)n1c(-c2nn(C3CCCCO3)c3ccc(I)cc23)cc2ccccc21]

tert-Butyl 2-(5-iodo-1-(tetrahydro-2H-pyran-2-yl)-1H-indazol-3-yl)-1H-indole-1-carboxylate. Intermediate 32A was prepared according to the procedure of Klapars and Buchwald (*J. Am. Chem. Soc.*, 2002, 124 (50), pp 14844-14845) where intermediate 32B (2.29 g, 4.61 mmol) was transferred as a solution in 5 mL anhydrous dioxane to a stir-bar equipped glass pressure tube containing trans-N,N'-dimethylcyclohexane-1,2-diamine (71 μL, 0.46 mmol), and NaI (1.38 g, 9.22 mmol). This mixture was sparged for 3 minutes with $N_2$ and treated with CuI (44 mg, 0.23 mmol). After an additional 2 minutes of $N_2$ sparging, the tube was sealed, heated to 110° C. and allowed to stir overnight. The resulting grey suspension was cooled, diluted with EtOAc and poured into 50 mL water and shaken. The aqueous layer was extracted twice with EtOAc and the combined organics were washed with brine, dried ($Na_2SO_4$), filtered, concentrated onto $SiO_2$ and purified on a Teledyne-ISCO Combiflash unit (40 g column, 0-10% EtOAc/heptane) to afford the desired product as 2.03 g of a pink, glassy solid (82%).

Intermediate 32B

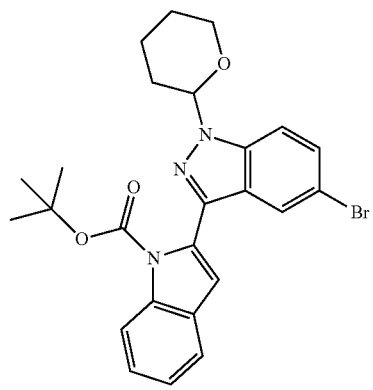 [SMILES: CC(C)(C)OC(=O)n1c(-c2nn(C3CCCCO3)c3ccc(Br)cc23)cc2ccccc21]

tert-Butyl 2-(5-bromo-1-(tetrahydro-2H-pyran-2-yl)-1H-indazol-3-yl)-1H-indole-1-carboxylate. Intermediate 32C (3.35 g, 8.23 mmol), N-(tert-butoxycarbonyl)indole-2-boronic acid (2.79 g, 10.7 mmol), Pd(Ph$_3$P)$_4$ (190.2 mg, 0.16 mmol), LiCl (1.05 g, 24.6 mmol) and $K_3PO_4$ (5.22 g, 24.6 mmol) were combined in a stir bar equipped 250 mL round bottom flask. This mixture was taken up in 40 mL dioxane and 12 mL $H_2O$ and sparged with $N_2$ for 3 minutes. The flask was sealed, heated to 80° C. and allowed to stir for 4 hours. After cooling, the reaction was diluted with EtOAc. The aqueous layer was removed, the organic layer was washed with 20 mL water, 10 mL brine, dried ($Na_2SO_4$), filtered and concentrated on to $SiO_2$. The desired product was isolated after chromatography (Teledyne-ISCO Combiflash, 80 g column, 0-10% EtOAc/heptane) as 2.29 g of a pink oil (56%).

Intermediate 32C

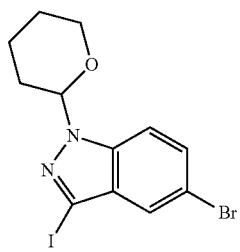 [SMILES: Brc1ccc2c(c1)c(I)nn2C1CCCCO1]

5-Bromo-3-iodo-1-(tetrahydro-2H-pyran-2-yl)-1H-indazole. 3,4-Dihydro-2H-pyran (4.5 mL, 49.6 mmol) was added to a suspension of Intermediate 32D (8.0 g, 24.8 mmol) and p-toluenesulfonic acid (943 mg, 4.96 mmol) in 100 mL DCM. The mixture was allowed to stir at rt overnight. The reaction mixture was concentrated in vacuo and partitioned between EtOAc and aqueous saturated sodium bicarbonate. The combined organic layers were washed with brine, dried ($Na_2SO_4$), filtered and concentrated to a brown oil that was filtered through a pad of silica (washing with 50%-100% DCM/Heptane). Removing the solvents in vacuo afforded the desired product as 9.12 g of a fluffy white solid (88%).

Intermediate 32D

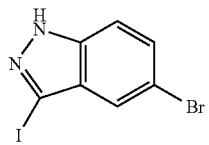 [SMILES: Brc1ccc2[nH]nc(I)c2c1]

5-bromo-3-iodo-1H-indazole. Iodine (8.37 g, 33 mmol) was added in portions to a mixture of 5-iodo-1H-indazole (5.0 g, 25.4 mmol) and $K_2CO_3$ (4.21 g, 30.5 mmol) in 100 mL of anhydrous DMF. After stirring overnight, the reaction mixture was poured into vigorously stirring ice water to form a thick black slurry. This was treated with an aqueous solution of $Na_2S_2O_3$ (10 M) until the slurry turned white. After stirring for 20 minutes, the mixture was filtered to collect the precipitated product. After drying, the desired product was isolated as 8.0 g of a white solid.

Example 33

This example provides a description of synthesis of (S)-3-(3-(1H-indol-2-yl)-1H-indazol-5-yl)-4-methyloxazolidin-2-one (33).

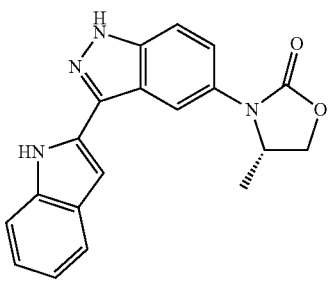 [SMILES: C[C@H]1COC(=O)N1c1ccc2[nH]nc(-c3cc4ccccc4[nH]3)c2c1]

Prepared using the same procedure as Example 32 using Intermediate 32A and (S)-4-methyloxazolidin-2-one instead of 1,3-propanesultam. The title compound was isolated as 21 mg of a tan solid after chromatography as described in Example 32 but using 0-5% MeOH/DCM as the mobile phase (49%). $^1$H NMR (600 MHz, DMSO-d6) δ 13.40 (s, 1H), 11.60 (s, 1H), 8.16 (d, J=1.5 Hz, 1H), 7.65 (d, J=8.9 Hz, 1H), 7.60 (d, J=7.8 Hz, 1H), 7.50 (dd, J=8.9, 1.9 Hz, 1H), 7.45 (d, J=8.0 Hz, 1H), 7.14-7.09 (m, 2H), 7.02 (t, J=7.8 Hz, 1H), 4.75 (dt, J=8.1, 6.3 Hz, 1H), 4.63 (t, J=8.3 Hz, 1H), 4.06 (dd, J=8.3, 6.4 Hz, 1H), 1.22 (d, J=6.2 Hz, 3H). $^{13}$C NMR (151 MHz, DMSO) δ 155.96, 139.37, 137.61, 136.48, 131.22, 130.39, 128.49, 123.92, 121.68, 120.00, 119.98, 119.22, 115.47, 111.49, 111.07, 99.77, 68.53, 52.90, 18.01.

Example 34

This example provides a description of synthesis of (R)-3-(3-(1H-indol-2-yl)-1H-indazol-5-yl)-4-methyloxazolidin-2-one (34).

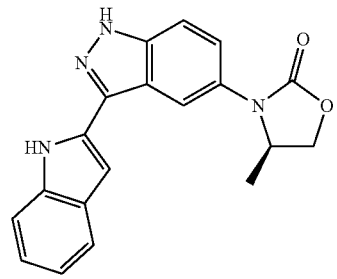 [SMILES: C[C@@H]1COC(=O)N1c1ccc2[nH]nc(-c3cc4ccccc4[nH]3)c2c1]

Prepared using the same procedure as Example 32 using Intermediate 32A and (R)-4-methyloxazolidin-2-one instead of 1,3-propanesultam. The title compound was isolated as 24 mg of a tan solid after chromatography as described in Example 32 but using 0-5% MeOH/DCM as the mobile phase (56%). $^1$H NMR (600 MHz, DMSO-d6) δ 13.41 (s, 1H), 11.60 (s, 1H), 8.19-8.14 (m, 1H), 7.67-7.63 (m, 1H), 7.60 (d, J=7.8 Hz, 1H), 7.50 (dd, J=8.9, 1.8 Hz, 1H), 7.45 (d, J=8.1 Hz, 1H), 7.12 (d, J=15.7 Hz, 2H), 7.02 (t, J=7.4 Hz, 1H), 4.75 (h, J=6.2 Hz, 1H), 4.63 (t, J=8.3 Hz, 1H), 4.06 (dd, J=8.3, 6.4 Hz, 1H), 1.22 (d, J=6.1 Hz, 3H). $^{13}$C NMR (151 MHz, DMSO) δ 155.96, 139.38, 137.62, 136.48, 131.23, 130.39, 128.50, 123.92, 121.69, 120.01, 119.98, 119.22, 115.47, 111.49, 111.07, 99.77, 68.53, 52.90, 18.01.

Example 35

This example provides a description of synthesis of (S)-3-(3-(1H-indol-2-yl)-1H-indazol-5-yl)-4-(hydroxymethyl)oxazolidin-2-one (35).

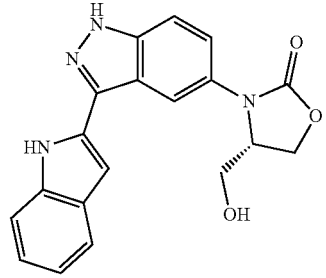 [SMILES: O=C1OC[C@H](CO)N1c1ccc2[nH]nc(-c3cc4ccccc4[nH]3)c2c1]

35 was prepared using the same procedure as Example 32 using Intermediate 32A and (S)-4-hydroxymethyloxazolidin-2-one instead of 1,3-propanesultam. The title compound was isolated as 29 mg of a tan solid after chromatography as described in Example 32 but using 0-100% EtOAc/heptane as the mobile phase (64%). $^1$H NMR (600 MHz, DMSO-d6) δ 13.39 (s, 1H), 11.60 (s, 1H), 8.22 (s, 1H), 7.64 (d, J=8.9 Hz, 1H), 7.60 (d, J=7.8 Hz, 1H), 7.55 (dd, J=8.9, 1.8 Hz, 1H), 7.45 (d, J=8.1 Hz, 1H), 7.11 (dd, J=13.7, 5.1 Hz, 2H), 7.02 (t, J=7.4 Hz, 1H), 5.08 (s, 1H), 4.67 (d, J=11.2 Hz, 1H), 4.55 (t, J=8.6 Hz, 1H), 4.36 (dd, J=8.3, 4.8 Hz, 1H), 3.51

(dd, J=11.9, 3.9 Hz, 1H), 3.45 (dd, J=11.8, 2.3 Hz, 1H). $^{13}$C NMR (151 MHz, DMSO) δ 156.37, 139.36, 137.61, 136.47, 131.26, 130.52, 128.48, 124.03, 121.69, 119.99, 119.94, 119.23, 115.73, 111.50, 110.93, 99.73, 64.32, 59.04, 58.27.

Example 36

This example provides a description of synthesis of (R)-3-(3-(1H-indol-2-yl)-1H-indazol-5-yl)-4-(hydroxymethyl)oxazolidin-2-one. (36)

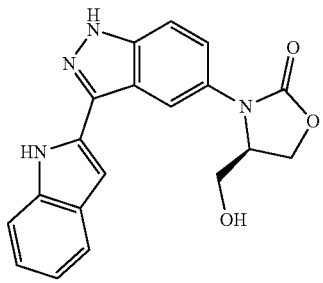 [SMILES: O=C1OC[C@@H](CO)N1c1ccc2[nH]nc(-c3cc4ccccc4[nH]3)c2c1]

36 was prepared using the same procedure as Example 32 using Intermediate 32A and (R)-4-hydroxymethyloxazolidin-2-one instead of 1,3-propanesultam. The title compound was isolated as 39 mg of a tan solid after chromatography as described in Example 32 but using 0-100% EtOAc/heptane as the mobile phase (86%). $^1$H NMR (600 MHz, DMSO-d6) δ 13.40 (s, 1H), 11.60 (s, 1H), 8.26-8.18 (m, 1H), 7.64 (d, J=8.9 Hz, 1H), 7.60 (d, J=7.9 Hz, 1H), 7.55 (dd, J=8.9, 1.8 Hz, 1H), 7.45 (d, J=7.8 Hz, 1H), 7.14-7.08 (m, 2H), 7.05-6.99 (m, 1H), 5.09 (s, 1H), 4.69-4.63 (m, 1H), 4.55 (t, J=8.6 Hz, 1H), 4.36 (dd, J=8.3, 4.8 Hz, 1H), 3.51 (dd, J=11.8, 3.8 Hz, 1H), 3.45 (d, J=10.0 Hz, 1H). $^{13}$C NMR (151 MHz, DMSO) δ 156.37, 139.37, 137.61, 136.47, 131.27, 130.52, 128.48, 124.02, 121.69, 119.99, 119.94, 119.23, 115.72, 111.50, 110.93, 99.72, 64.32, 59.04, 58.27.

Example 37

This example provides a description of synthesis of (S)-3-(3-(1H-indol-2-yl)-1H-indazol-5-yl)-4-phenyloxazolidin-2-one (37).

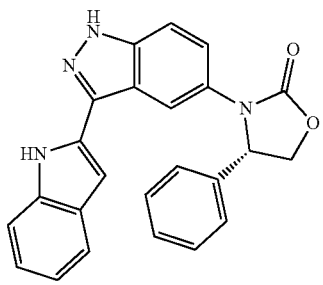 [SMILES: O=C1OC[C@H](c2ccccc2)N1c1ccc2[nH]nc(-c3cc4ccccc4[nH]3)c2c1]

37 was prepared using the same procedure as Example 32 using Intermediate 32A and (S)-4-phenyloxazolidin-2-one instead of 1,3-propanesultam. The title compound was isolated as 29 mg of a tan solid after chromatography as described in Example 32 but using 0-50% EtOAc/heptane as the mobile phase (61%). $^1$H NMR (500 MHz, DMSO-d6) δ 13.31 (s, 1H), 11.55 (s, 1H), 8.06-8.03 (m, 1H), 7.62 (d, J=7.9 Hz, 1H), 7.55-7.52 (m, 2H), 7.51-7.47 (m, 2H), 7.45-7.42 (m, 1H), 7.35 (t, J=7.6 Hz, 2H), 7.29-7.24 (m, 1H), 7.14-7.09 (m, 1H), 7.03 (ddd, J=7.9, 7.3, 1.0 Hz, 1H), 6.92 (d, J=1.4 Hz, 1H), 5.87 (dd, J=8.7, 6.6 Hz, 1H), 4.90 (t, J=8.7 Hz, 1H), 4.23 (dd, J=8.6, 6.6 Hz, 1H). $^{13}$C NMR (151 MHz, DMSO) δ 156.07, 138.92, 138.88, 136.41, 131.13, 130.85, 128.97, 128.44, 128.42, 127.14, 122.87, 121.70, 119.99, 119.66, 119.23, 114.11, 111.48, 110.80, 99.57, 69.57, 60.51.

Example 38

This example provides a description of synthesis of (R)-3-(3-(1H-indol-2-yl)-1H-indazol-5-yl)-4-phenyloxazolidin-2-one (38).

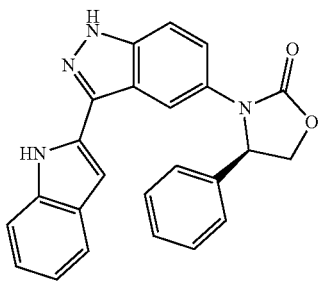 [SMILES: O=C1OC[C@@H](c2ccccc2)N1c1ccc2[nH]nc(-c3cc4ccccc4[nH]3)c2c1]

38 was prepared using the same procedure as Example 32 using Intermediate 32A and (R)-4-phenyloxazolidin-2-one instead of 1,3-propanesultam. The title compound was isolated as 17 mg of a tan solid after 2 chromatographic purifications as described in Example 32 but using 0-50% EtOAc/heptane as the mobile phase (36%). $^1$HNMR (600 MHz, Chloroform-d) δ 10.41 (s, 1H), 9.14 (s, 1H), 7.79-7.73 (m, 1H), 7.67 (d, J=7.8 Hz, 1H), 7.44 (dd, J=9.0, 2.0 Hz, 1H), 7.38 (d, J=4.4 Hz, 4H), 7.35-7.30 (m, 2H), 7.25 (s, 1H), 7.21 (ddd, J=8.1, 7.1, 1.1 Hz, 1H), 7.17-7.12 (m, 1H), 6.77-6.72 (m, 1H), 5.41-5.34 (m, 1H), 4.85 (t, J=8.8 Hz, 1H), 4.34 (dd, J=8.7, 6.6 Hz, 1H). $^{13}$C NMR (151 MHz, CDCl3) δ 157.18, 138.31, 136.19, 131.13, 130.73, 129.67, 129.36, 129.04, 127.06, 123.32, 123.00, 120.88, 120.57, 120.25, 114.91, 111.25, 110.88, 101.30, 70.21, 62.43.

Example 39

This example provides a description of synthesis of (S)-3-(3-(1H-indol-2-yl)-1H-indazol-5-yl)-4-isopropyloxazolidin-2-one (39).

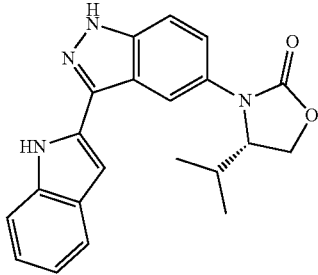 [SMILES: CC(C)[C@H]1COC(=O)N1c1ccc2[nH]nc(-c3cc4ccccc4[nH]3)c2c1]

39 was prepared using the same procedure as Example 32 using Intermediate 32A and (S)-4-isopropyloxazolidin-2-one instead of 1,3-propanesultam. The title compound was isolated as 7.5 mg of a tan solid after chromatography (0-60% EtOAc/heptane) followed by a trituration in DCM (36%). ¹H NMR (600 MHz, DMSO-d6) δ 13.41 (s, 1H), 11.60 (s, 1H), 8.22 (s, 1H), 7.68-7.63 (m, 1H), 7.61 (d, J=7.8 Hz, 1H), 7.54 (dd, J=8.9, 1.5 Hz, 1H), 7.47-7.42 (m, 1H), 7.14-7.08 (m, 2H), 7.02 (t, J=7.4 Hz, 1H), 4.75 (dt, J=8.6, 4.4 Hz, 1H), 4.49 (t, J=8.9 Hz, 1H), 4.31 (dd, J=8.8, 4.9 Hz, 1H), 1.91 (ddd, J=13.5, 8.6, 5.2 Hz, 1H), 0.86 (d, J=7.0 Hz, 3H), 0.81 (d, J=6.8 Hz, 3H). ¹³C NMR (151 MHz, DMSO) δ 156.14, 139.27, 137.61, 136.49, 131.22, 130.74, 128.49, 123.65, 121.71, 120.04, 119.94, 119.24, 115.22, 111.50, 111.09, 99.77, 62.70, 60.64, 27.81, 17.24, 14.49.

Example 40

This example provides a description of synthesis of 3-(3-(1H-indol-2-yl)-1H-indazol-5-yl)-1,3-oxazinan-2-one (40).

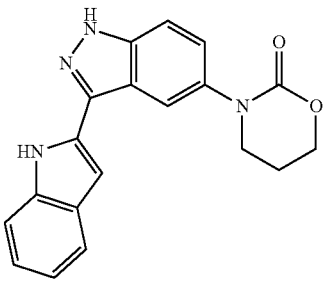 [SMILES: O=C1OCCCN1c1ccc2[nH]nc(-c3cc4ccccc4[nH]3)c2c1]

40 was prepared using the same procedure as Example 32 using Intermediate 32A and 1,3-oxazin-2-one instead of 1,3-propanesultam. The title compound was isolated as 14 mg of a tan solid after chromatography as described in Example 32 but using 0-50%-70%-100% EtOAc/heptane as the mobile phase (32%). ¹H NMR (600 MHz, Chloroform-d) δ 11.40 (s, 1H), 9.17 (s, 1H), 7.86 (d, J=1.3 Hz, 1H), 7.61 (d, J=7.8 Hz, 1H), 7.18-7.05 (m, 5H), 6.95 (d, J=1.5 Hz, 1H), 4.58-4.45 (m, 2H), 3.74 (t, J=6.0 Hz, 2H), 2.26 (p, J=6.0 Hz, 2H). ¹³C NMR (151 MHz, CDCl3) δ 154.53, 140.30, 138.74, 136.42, 136.39, 131.02, 128.86, 125.85, 122.70, 120.60, 120.54, 120.05, 118.78, 112.13, 111.45, 100.88, 67.47, 50.04, 22.74, 21.28, 14.42.

Example 41

This example provides a description of synthesis of 1-(3-(1H-indol-2-yl)-1H-indazol-5-yl)piperidin-2-one (41).

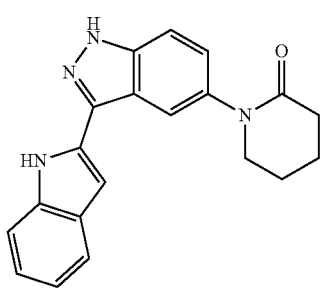 [SMILES: O=C1CCCCN1c1ccc2[nH]nc(-c3cc4ccccc4[nH]3)c2c1]

41 was prepared using the same procedure as Example 32 using Intermediate 32A and 2-piperidinone instead of 1,3-propanesultam. The title compound was isolated as 18 mg of a tan solid after chromatography as described in Example 32 but using a stepped gradient of 0-50%-70%-100% EtOAc/heptane as the mobile phase (41%). ¹H NMR (600 MHz, Chloroform-d) δ 11.18 (s, 1H), 8.87 (s, 1H), 7.82-7.78 (m, 1H), 7.65-7.59 (m, 1H), 7.15 (d, J=8.7 Hz, 1H), 7.12-7.06 (m, 3H), 6.96-6.92 (m, 2H), 3.73 (m, 2H), 2.69 (m, 2H), 2.05 (m, 4H). ¹³C NMR (151 MHz, CDCl3) δ 171.73, 140.40, 138.71, 136.89, 136.21, 131.13, 128.82, 125.73, 122.71, 120.80, 120.49, 119.99, 118.75, 112.36, 111.29, 100.73, 52.99, 33.08, 23.79, 21.68. MS (ES⁺): m/z=(M).

Example 42

This example provides a description of synthesis of 1-(3-(1H-indol-2-yl)-1H-indazol-5-yl)pyrrolidin-2-one (42).

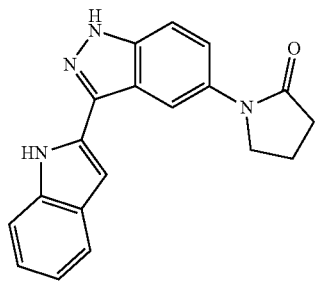 [SMILES: O=C1CCCN1c1ccc2[nH]nc(-c3cc4ccccc4[nH]3)c2c1]

42 was prepared using the same procedure as Example 32 using Intermediate 32A and pyrrolidin-2-one instead of 1,3-propanesultam. The title compound was isolated as 31 mg of a tan solid after chromatography as described in Example 32 but using 0-50% EtOAc/heptane as the mobile phase (75%). ¹H NMR (600 MHz, DMSO-d6) δ 13.32 (s, 1H), 11.58 (s, 1H), 8.19 (s, 1H), 7.86-7.78 (m, 1H), 7.60 (d, J=8.7 Hz, 2H), 7.45 (d, J=8.0 Hz, 1H), 7.11 (t, J=7.5 Hz, 1H), 7.07 (s, 1H), 7.02 (t, J=7.4 Hz, 1H), 4.07-3.95 (m, 2H), 2.54 (t, J=8.0 Hz, 2H), 2.13 (p, J=7.6 Hz, 2H). ¹³C NMR (151 MHz, DMSO) δ 173.63, 138.59, 137.52, 136.44, 133.69, 131.42, 128.50, 121.61, 121.19, 119.98, 119.71, 119.18, 111.45, 111.19, 110.52, 99.55, 49.11, 39.93, 39.79, 39.65, 39.51, 39.37, 39.23, 39.09, 32.17, 17.60. MS (ES⁺): m/z=(M).

Example 43

This example provides a description of synthesis of methyl (S)-1-(3-(1H-indol-2-yl)-1H-indazol-5-yl)-5-oxopyrrolidine-2-carboxylate (43).

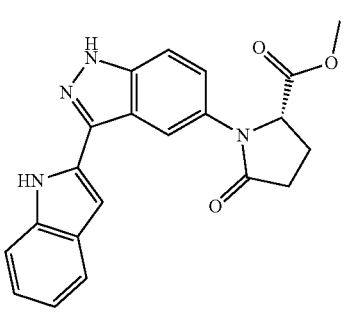 [SMILES: COC(=O)[C@@H]1CCC(=O)N1c1ccc2[nH]nc(-c3cc4ccccc4[nH]3)c2c1]

43 was prepared using the same procedure as Example 32 using Intermediate 32A and methyl (L) pyroglutamate instead of 1,3-propanesultam. The title compound was isolated as 49 mg of a tan solid after chromatography as described in Example 32 but using a stepped gradient of 0-50%-70%-100% EtOAc/heptane as the mobile phase (46%). $^1$H NMR (400 MHz, Chloroform-d) δ 10.71 (s, 1H), 9.17 (s, 1H), 7.97 (s, 1H), 7.65 (d, J=7.8 Hz, 1H), 7.43 (d, J=8.8 Hz, 1H), 7.26 (q, J=8.2, 6.9 Hz, 2H), 7.18 (t, J=7.4 Hz, 1H), 7.12 (t, J=7.3 Hz, 1H), 6.99 (s, 1H), 4.79 (dd, J=8.5, 2.8 Hz, 1H), 3.74 (s, 3H), 2.94-2.78 (m, 1H), 2.73-2.55 (m, 2H), 2.34-2.21 (m, 1H).

Example 44

This example provides a description of synthesis of (S)-1-(3-(1H-indol-2-yl)-1H-indazol-5-yl)-5-oxopyrrolidine-2-carboxylic acid (44).

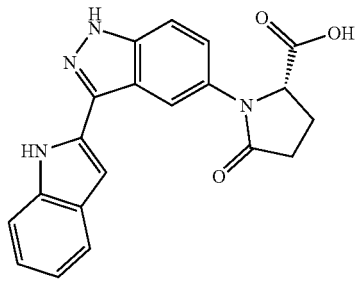 [SMILES: O=C(O)[C@@H]1CCC(=O)N1c1ccc2[nH]nc(-c3cc4ccccc4[nH]3)c2c1]

LiOH.H$_2$O (23 mg, 0.55 mmol) was added to a solution of Example 43 (41.5 mg, 0.11 mmol) in 1 mL THF and 1 mL H$_2$O. After stirring for 90 minutes, the reaction was quenched with 1N HCl dropwise until turbidity persisted. The reaction was poured into water and extracted twice with EtOAc. The combined organic layers were washed with brine, dried (Na$_2$SO$_4$), filtered and concentrated to a clear film. This was dissolved in a minimum amount of EtOAc and precipitated with heptane. The precipitate was collected by filtration and after drying afforded 28 mg of an off-white solid (69%). $^1$H NMR (600 MHz, DMSO-d6) δ 13.37 (s, 1H), 13.12 (s, 1H), 11.61 (s, 1H), 8.13 (s, 1H), 7.66-7.56 (m, 3H), 7.45 (d, J=7.9 Hz, 1H), 7.12 (t, J=7.3 Hz, 1H), 7.03 (d, J=7.3 Hz, 2H), 5.10-4.98 (m, 1H), 2.68-2.51 (m, 3H), 2.13 (d, J=11.9 Hz, 1H). $^{13}$C NMR (151 MHz, DMSO) δ 174.02, 173.62, 139.08, 137.54, 136.44, 132.48, 131.31, 128.45, 123.14, 121.69, 119.96, 119.70, 119.24, 113.71, 111.50, 110.64, 99.45, 61.85, 30.45, 22.57.

Example 45

The following is an example of a CaMKK1/2-biochemical assay. Compounds were tested for CaMKK1/2 inhibition using a $^{32}$P radiometric kinase assay as follows: A freshly prepared kinase reaction buffer (20 mM Hepes (pH 7.5), 10 mM MgCl$_2$, 1 mM EGTA, 0.02% Brij35, 0.02 mg/ml BSA, 0.1 mM Na$_3$VO$_4$, 2 mM DTT, 1% DMSO) was treated with Myelin Basic Protein (final concentration=20 μM), CaCl$_2$) (final concentration=1.5 mM), Calmodulin (final concentration=0.96 μM) and either CaMKK2 (final reaction concentration=120 nM) or CaMKK1 (final reaction concentration=150 nM) and gently mixed. Compounds were added as aliquots from 10 mM DMSO stock solutions such that the final compound concentration in the assay was either 10 μM, 0.5 μM or 0.2 μM. This mixture was allowed to incubate for 20 minutes at room temperature. $^{32}$P-ATP (specific activity 10 μCi/μL) was added and the mixture was allowed to incubate for 2 hours at room temperature. The reaction mixture was spotted onto P81 ion exchange paper. The kinase activity was detected by the filter binding method.

The following is an example of a CaMKK1/2 cellular signaling assay. HeLa cells purchased from ATCC were maintained in Dulbecco's Modified Eagle's Medium (DMEM) supplemented with 10% fetal bovine serum. 24 hours prior to compound treatment, cells were re-plated at a density of 100,000 cells/well in 12-well tissue culture treated plates. Compounds were resuspended in DMSO, applied to cells at the desired dose for 2 hours at 37° C. Prior to harvest, cells were treated with calcium-ionophore ionomycin (2 μM) for 5 minutes in order to increase the concentration of cytosolic calcium (Ca$^{2+}$), stimulating CAMKK2 activity. Cells were then quickly washed once with PBS and immediately lysed in situ using a denaturing lysis buffer (8 M urea, 4% CHAPS, 50 mM Tris pH 7.5) in order to preserve the phosphorylation state of CAMKK2 substrate proteins. Lysates were cleared of insoluble debris by centrifugation at 16,000×g for 10 min, combined with Laemmeli buffer containing reducing agent, boiled at 95° C. for 5 min and run on 4-12% Tris-Bis gradient precast gels. Proteins were transferred to PVDF membrane (overnight, 25 V, 4° C.), visualized with Ponceau S. Membranes were blocked with 5% BSA in TBS-T, probed with anti-p-AMPK and anti-actin antibodies (Cell Signaling; 1:2000, 1:4000 respectively) diluted in blocking buffer, blotted with an HRP-conjugated secondary anti-rabbit antibody (Roche), and developed using commercially available chemiluminescent reagents visualized by film. Example: FIG. 1.

TABLE 1

Inhibition of inhibitors of the present disclosure.

| | CaMKK2 % inhibition @ concentrations shown | | | IC$_{50}$ Data (nM) | | Cell based inhibition @ 10 μM |
|---|---|---|---|---|---|---|
| Example | 10 μM | 0.5 μM | 0.2 μM | CaMKK2 | CaMKK1 | pAMPK |
| 1 | 72% | | | | | |
| 2 | 98% | | | | 164 | |
| 3 | 100% | 94% | 80% | 70 | 141 | +++ |
| 4 | 98% | 81% | 55% | 190 | | − |
| 5 | 29% | | | | | |
| 6 | | 37% | | | | |
| 7 | | 29% | | | | |
| 8 | | 26% | | | | |
| 9 | | 89% | | | | + |
| 10 | | 72% | | | | − |
| 11 | | 80% | | | | + |
| 12 | | 52% | | | | − |
| 13 | | 33% | | | | |
| 14 | | 71% | | | | + |
| 15 | | 85% | | | | +++ |
| 16 | | 77% | | | | ++ |
| 17 | | 71% | | | | +++ |
| 18 | | 61% | | | | + |
| 19 | | 87% | | | | +++ |
| 20 | | 84% | | | | +++ |
| 21 | | 84% | | | | +++ |
| 22 | | 37% | | | | − |
| 23 | | 44% | | | | − |
| 24 | | 41% | | | | |
| 25 | | 67% | | | | + |
| 26 | | 36% | | | | − |
| 27 | | 59% | | | | − |
| 28 | | 44% | | | | − |
| 29 | | 63% | | | | ++ |
| 30 | | 75% | | | | +++ |
| 31 | | 81% | | 33 | 536 | +++ |
| 32 | | 84% | | | | ++ |

TABLE 1-continued

Inhibition of inhibitors of the present disclosure.

| | CaMKK2 % inhibition @ concentrations shown | | | IC$_{50}$ Data (nM) | | Cell based inhibition @ 10 µM |
|---|---|---|---|---|---|---|
| Example | 10 µM | 0.5 µM | 0.2 µM | CaMKK2 | CaMKK1 | pAMPK |
| 33 | | 90% | | | | +++ |
| 34 | | 73% | | | | + |
| 35 | | 68% | | | | +++ |
| 36 | | 57% | | | | +++ |
| 37 | | 74% | | | | ++ |
| 38 | | 50% | | | | +++ |
| 39 | | 72% | | | | + |
| 40 | | 37% | | | | + |
| 41 | | 12% | | | | − |
| 42 | | 56% | | | | ++ |
| 43 | | 38% | | | | +++ |
| 44 | | 78% | | | | − |

Example 46

This example provides a description of compounds of the present disclosure with reference to their activity.

"Lower activity" is defined as <50% CaMKK2 inhibition at 0.2 µM compound concentration. Cell based activity is defined relative to STO-609—the literature CaMKK2 inhibitor.

TABLE 2

Comparison of mechanistic activity in HeLa cells of compounds at 10 µM concentrations.

| Compound (at 10 µM) | Inhibition of p-AMPK | Example from blot below |
|---|---|---|
| STO-609 | ++ | STO = STO-609 |
| No Activity | − | CL-664 |
| Sub STO-609 potency | + | CL-665 |
| Equivalent to STO-609 | ++ | CL-670 |
| Superior to STO-609 (complete knockdown of pAMPK signal) | +++ | CL-576 |
| | | CL-673 |

TABLE 3

Poorly active compounds that are within in the generic structure.

| | | Biochemical Data | | Cell data Inh. of |
|---|---|---|---|---|
| ID | Structure | CaMKK1 | CaMKK2 | AMPKP |
| CL-599 | 3-phenyl-1H-indazol-5-yl oxazolidin-2-one | <5% inh @ 0.5 µM | 37% inh @ 0.5 µM | nd |
| CL-600 | 3-(pyridin-3-yl)-1H-indazol-5-yl oxazolidin-2-one | <5% inh @ 0.5 µM | 29% inh @ 0.5 µM | nd |
| CL-622 | 3-vinyl-1H-indazol-5-yl oxazolidin-2-one | 12% inh @ 0.5 µM | 26% inh @ 0.5 µM | nd |

TABLE 3-continued

Poorly active compounds that are within in the generic structure.

| ID | Structure | Biochemical Data | | Cell data Inh. of |
|---|---|---|---|---|
| | | CaMKK1 | CaMKK2 | AMPKP |
| CL-626 | | 14% inh @ 0.5 µM | 52% inh @ 0.5 µM | – |
| CL-627 | | 7% inh @ 0.5 µM | 33% inh @ 0.5 µM | nd |
| CL-628 | | <5% inh @ 0.5 µM | 22% inh @ 0.5 µM | nd |
| CL-629 | | <5% inh @ 0.5 µM | 20% inh @ 0.5 µM | nd |
| CL-662 | | <5% inh @ 0.2 µM | 37% inh @ 0.2 µM | – |
| CL-663 | | <5% inh @ 0.2 µM | 44% inh @ 0.2 µM | – |

TABLE 3-continued

Poorly active compounds that are within in the generic structure.

| ID | Structure | Biochemical Data | | Cell data Inh. of |
|---|---|---|---|---|
| | | CaMKK1 | CaMKK2 | AMPKP |
| CL-664 | | <5% inh @ 0.2 µM | 41% inh @ 0.2 µM | − |
| CL-666 | | <5% inh @ 0.2 µM | 15% inh @ 0.2 µM | − |
| CL-667 | | <5% inh @ 0.2 µM | 36% inh @ 0.2 µM | − |
| CL-669 | | <5% inh @ 0.2 µM | 55% inh @ 0.2 µM | − |
| CL-689 | | <5% inh @ 0.2 µM | 37% inh @ 0.2 µM | + |

TABLE 3-continued

Poorly active compounds that are within in the generic structure.

| ID | Structure | Biochemical Data | | Cell data Inh. of |
|---|---|---|---|---|
| | | CaMKK1 | CaMKK2 | AMPKP |
| CL-690 | [structure: 1H-indazole substituted at 3-position with 1H-indol-2-yl and at 5-position with 2-oxopiperidin-1-yl] | <5% inh @ 0.2 µM | 12% inh @ 0.2 µM | – |

TABLE 4

Prophetic examples of compounds of the present disclosure.

[Core structure: 1H-pyrazolo fused bicyclic with X in ring, R2 substituent, and vinyl-R1 at 3-position]

| ID | i | ii | iii | iv | v |
|---|---|---|---|---|---|
| R1 | 4-pyridinyl N-oxide | 4-methoxyphenyl | 4-methoxyphenyl | 4-methoxyphenyl | 4-methoxyphenyl |
| X | CH | N | CH | N | CH |
| R2 | oxazolidin-2-one (N-linked) | oxazolidin-2-one (N-linked) | (4-methyl)oxazolidin-2-one | (4-methyl)oxazolidin-2-one | (4-methoxymethyl)oxazolidin-2-one |

| ID | vi | vii | viii | ix |
|---|---|---|---|---|
| R1 | 4-methoxyphenyl | 2-fluoro-4-methoxyphenyl | 4-methoxyphenyl | 4-methoxyphenyl |
| X | N | N | CH | N |

TABLE 4-continued

TABLE 5

Compounds and prophetic compounds of the present disclosure consisting of ONE Indazole-3-Substituent, ONE Indazole Core and ONE Indazole 5-substituent.

| Indazole 3-Substituents (3 individuals per cell) | Indazole Cores (one core/cell) | Indazole 5-substituents (3 individuals per cell) |
| --- | --- | --- |

TABLE 5-continued

Compounds and prophetic compounds of the present disclosure consisting of ONE Indazole-3-Substituent,
ONE Indazole Core and ONE Indazole 5-substituent.

| Indazole 3-Substituents (3 individuals per cell) | Indazole Cores (one core/cell) | Indazole 5-substituents (3 individuals per cell) |
|---|---|---|

TABLE 5-continued

Compounds and prophetic compounds of the present disclosure consisting of ONE Indazole-3-Substituent, ONE Indazole Core and ONE Indazole 5-substituent.

| Indazole 3-Substituents (3 individuals per cell) | Indazole Cores (one core/cell) | Indazole 5-substituents (3 individuals per cell) |
|---|---|---|

X = CH or N; R = H, Cl, OCH$_3$

R = H, Cl, OCH$_3$

R = CH3, Cl, F

R = H, OCH$_3$

Although the present disclosure has been described with respect to one or more particular embodiments and/or examples, it will be understood that other embodiments and/or examples of the present disclosure may be made without departing from the scope of the present disclosure.

The invention claimed is:

1. A compound having the following structure:

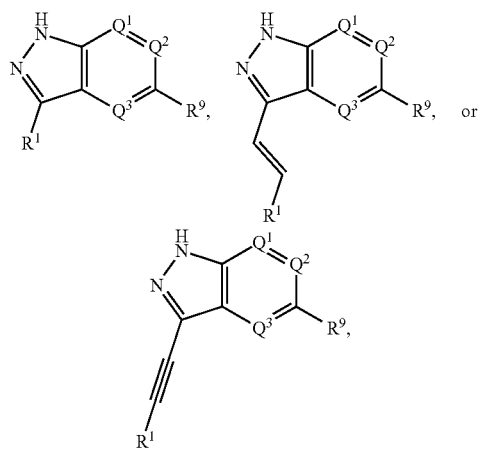

where $R^9$ is

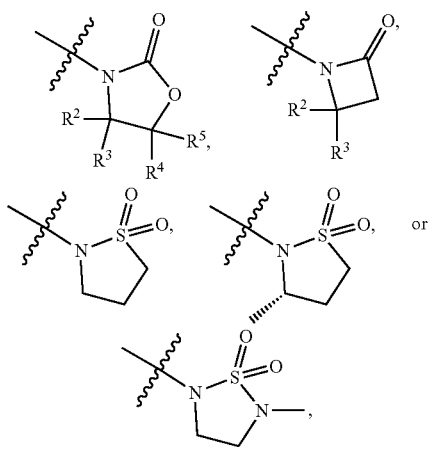

where $R^1$ is chosen from halogens, substituted or unsubstituted aliphatic groups, substituted or unsubstituted benzyl groups, substituted or unsubstituted cycloalkyl groups, substituted or unsubstituted heterocycloalkyl groups, substituted or unsubstituted aryl groups, substituted or unsubstituted heteroaryl groups, CH=CHR$^6$, —CCR$^6$, —COR$^6$, CO$_2$R$^7$, —CONHR$^7$, CONR$^7$R$^8$, and —NHR$^6$;

$Q^1$, $Q^2$, and $Q^3$ are independently chosen from C—H, C—F, or N;

$R^2$, $R^3$, $R^4$, and $R^5$ are independently chosen from hydrogen, —CH$_3$, —CH$_2$CH$_3$, benzyl groups, i-isopropyl groups, —CH$_2$OH, —CH$_2$NH$_2$, —CH$_2$NHR$^6$, —CH$_2$NR$^6$R$^7$, —CH$_2$CONH$_2$, —CH$_2$CONHMe, —OR$^6$, —(CH$_2$)$_x$OR$^6$, —CH$_2$CH$_2$CH$_3$, —CH$_2$CH$_2$OH, —CH$_2$CH$_2$NH$_2$, —CH$_2$CH$_2$NHR$^6$, —CH$_2$CH$_2$R$^6$R$^7$, —CH$_2$CH$_2$CONH$_2$, and —CH$_2$CH$_2$CONHMe, wherein x is 1, 2, 3, 4, or 5;

$R^6$ is chosen from hydrogen, OH, alkyl groups, cycloalkyl groups, aryl groups, and heteroaryl groups, wherein $R^6$ (except hydrogen) is optionally substituted with one or more $R^7$ group; and $R^7$ and $R^8$ are independently chosen from alkyl groups, hydroxyl groups, alkoxy groups, arylalkyl groups, substituted or unsubstituted heteroaryl groups, substituted or unsubstituted heterocyclyl groups, and substituted or unsubstituted heterocycloalkyoxy groups, wherein $R^7$ and $R^8$ can be combined to form a 3, 4, 5, 6, or 7 member ring.

2. The compound of claim 1, wherein $R^9$ is chosen from

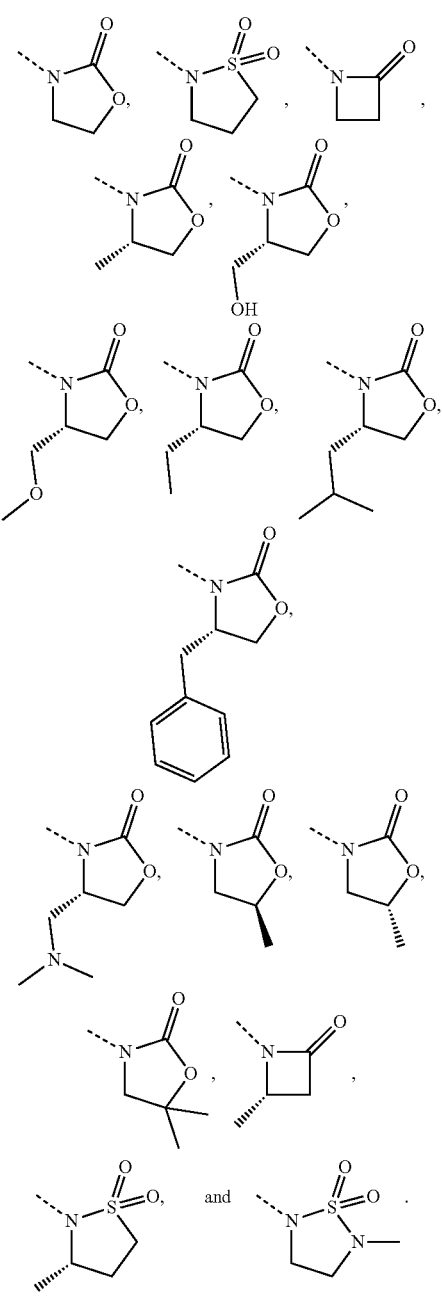

3. The compound of claim 1, wherein the compound has the following structure:

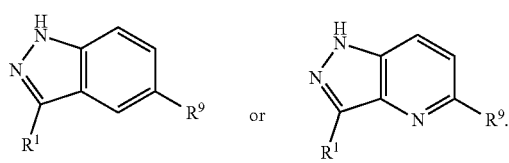
4. The compound of claim 1, wherein R¹ is chosen from:
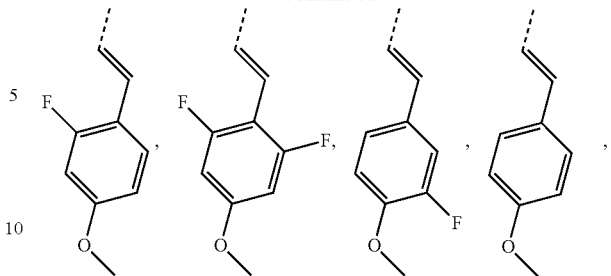
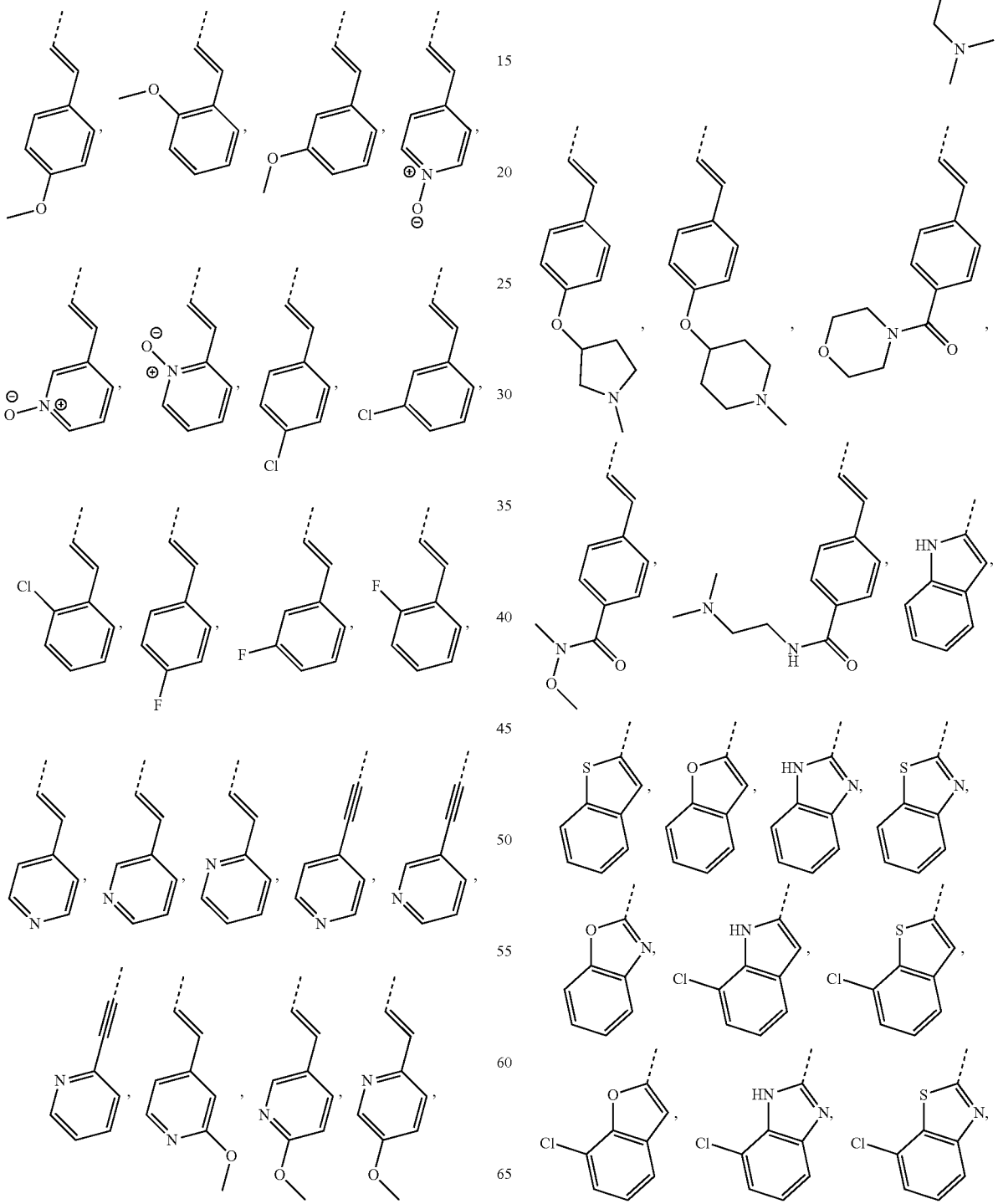

-continued
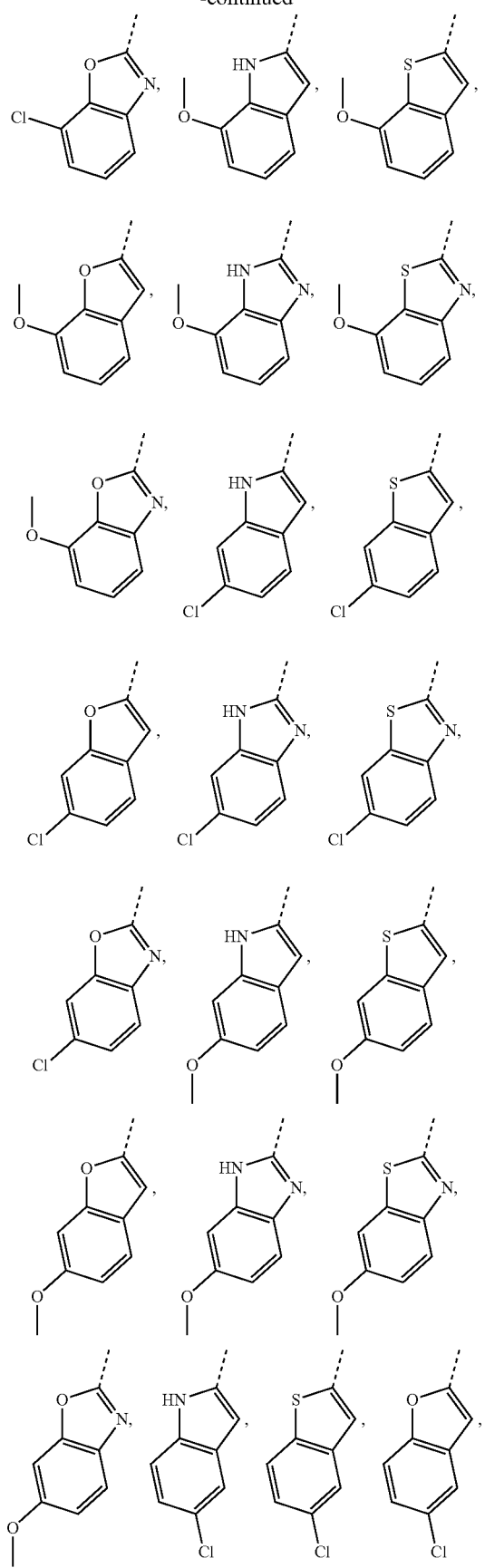
-continued
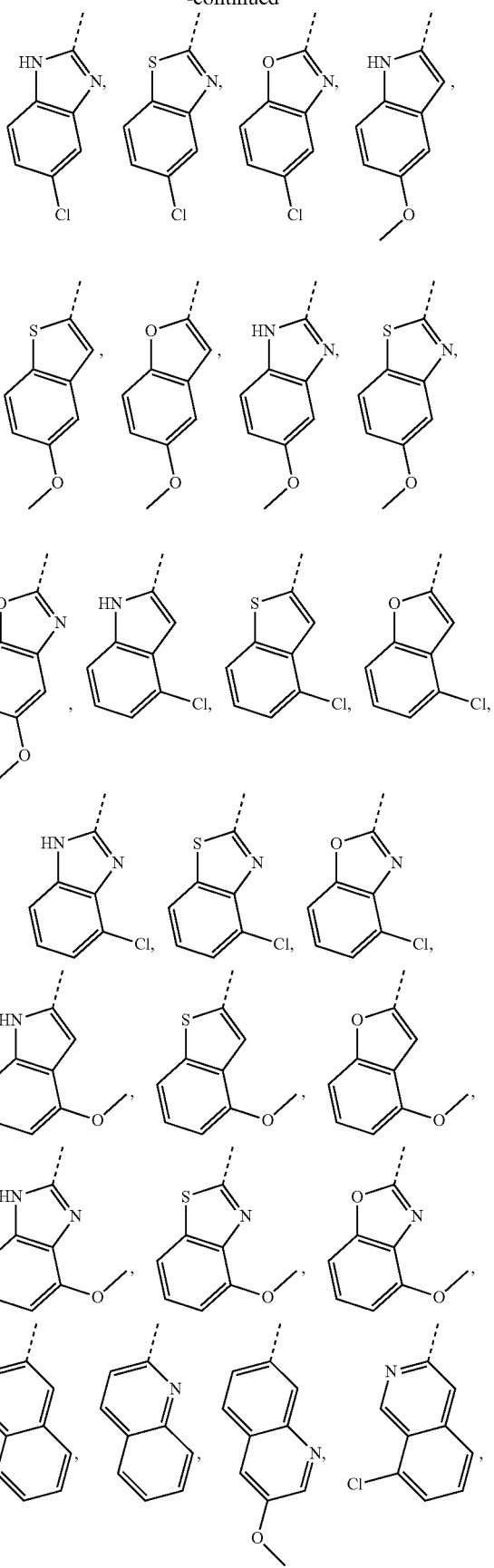

89
-continued
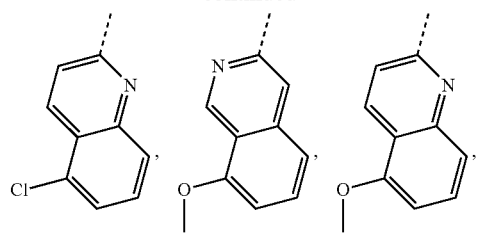
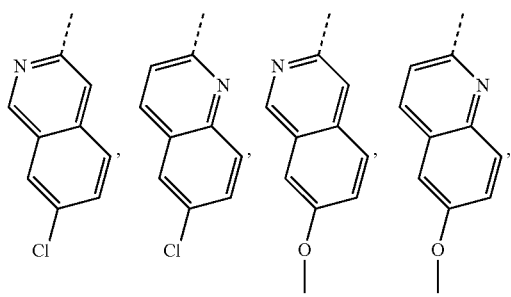
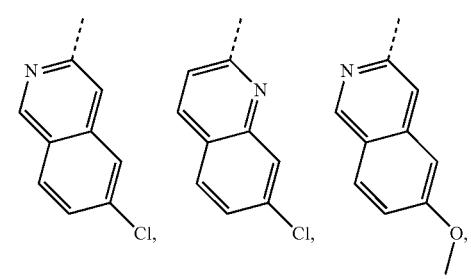
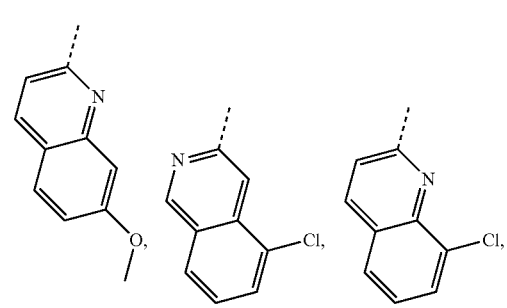
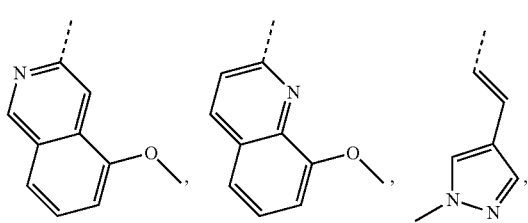
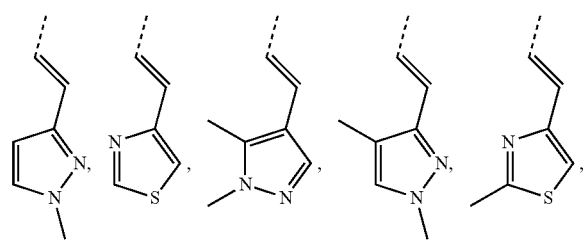
90
-continued
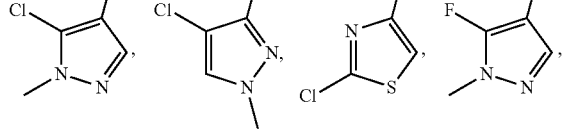
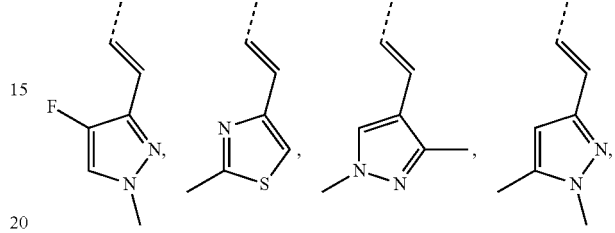
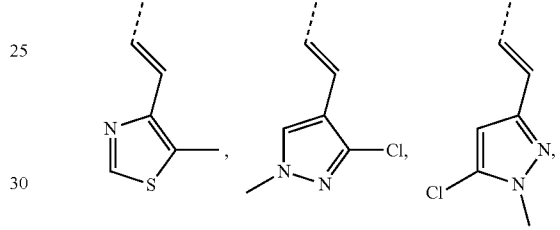
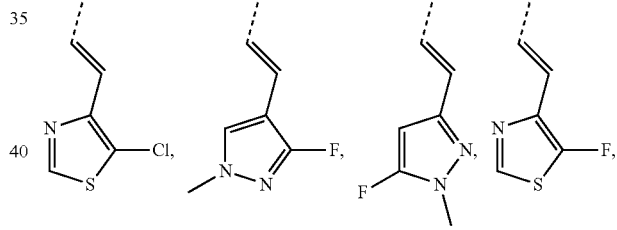
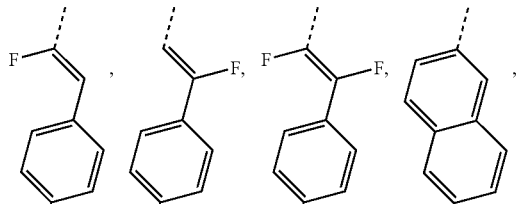
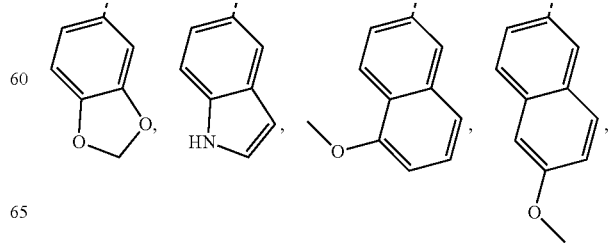

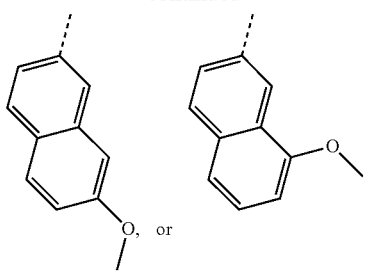
5. The compound of claim 1, wherein the compound has the following structure:
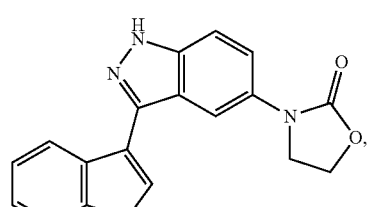
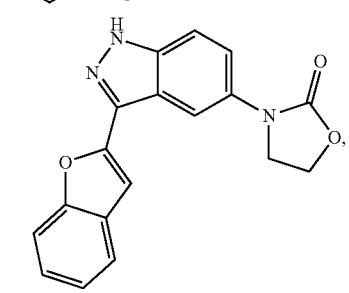
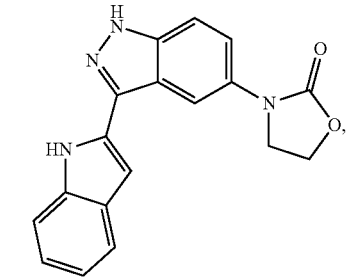
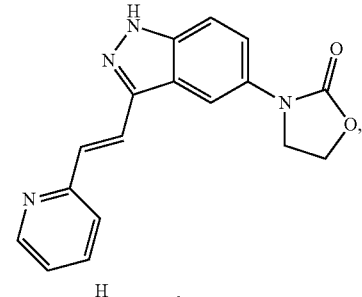
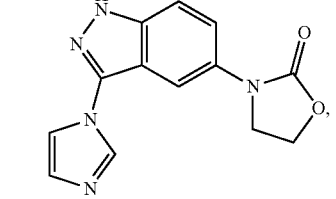
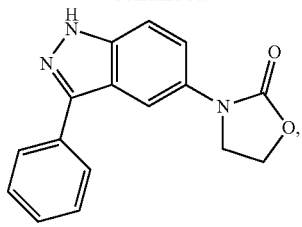
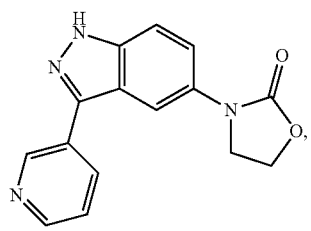
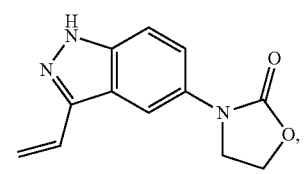
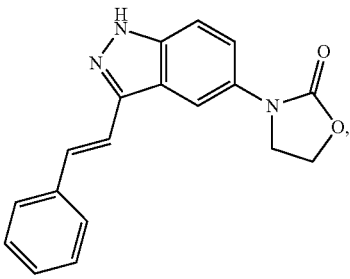
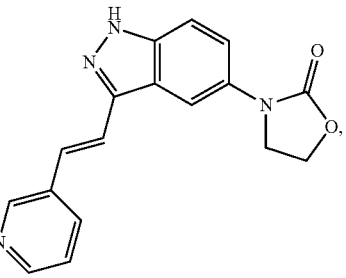
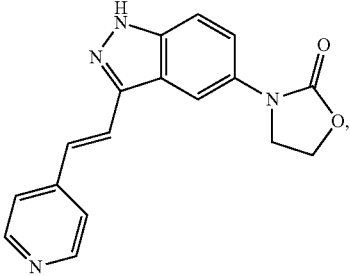

-continued
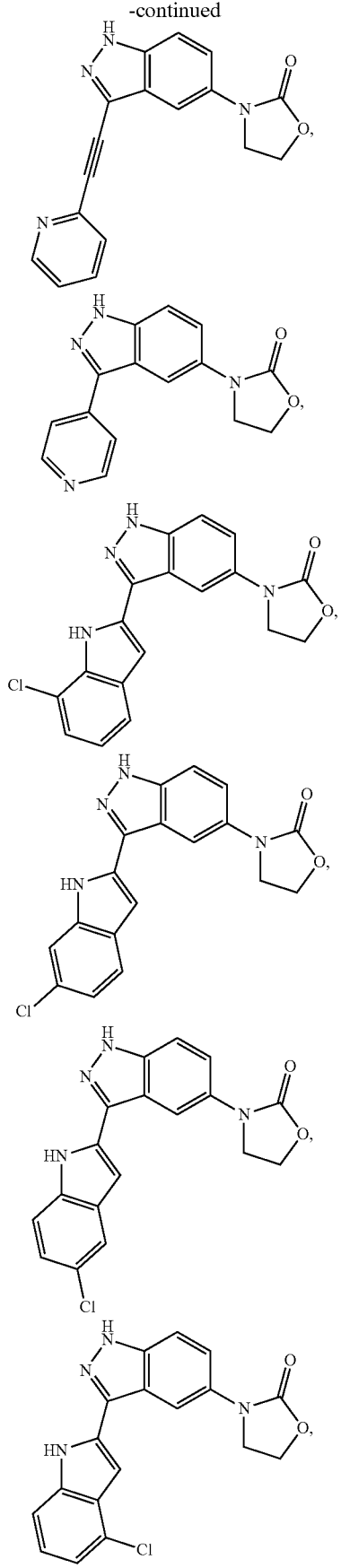
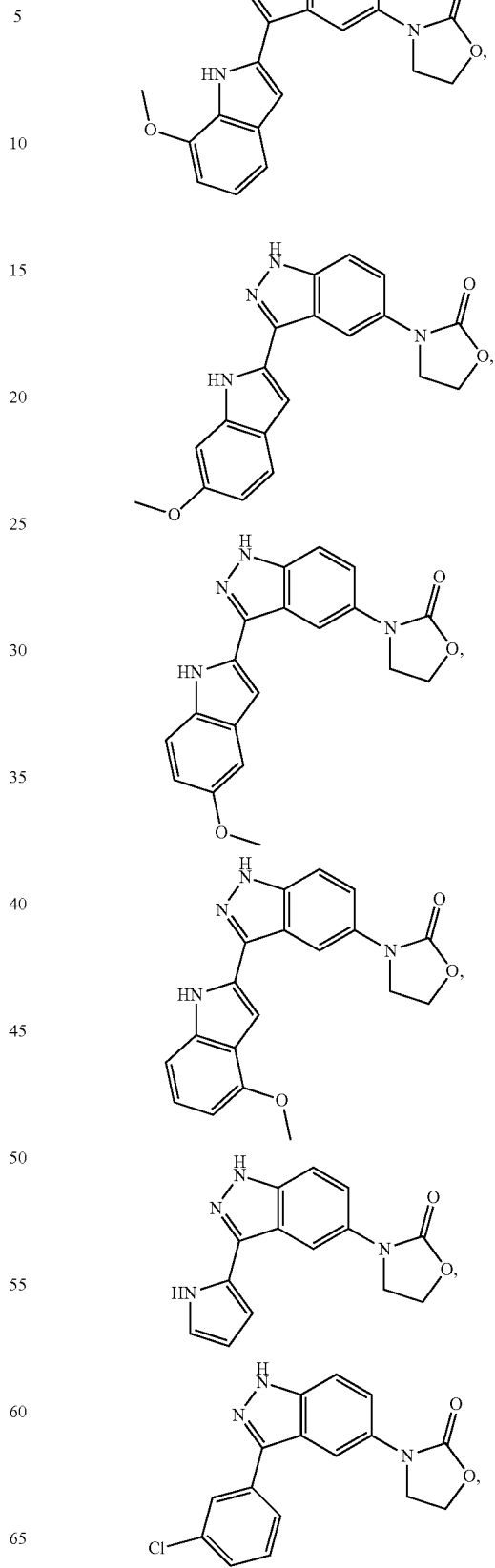

95
-continued
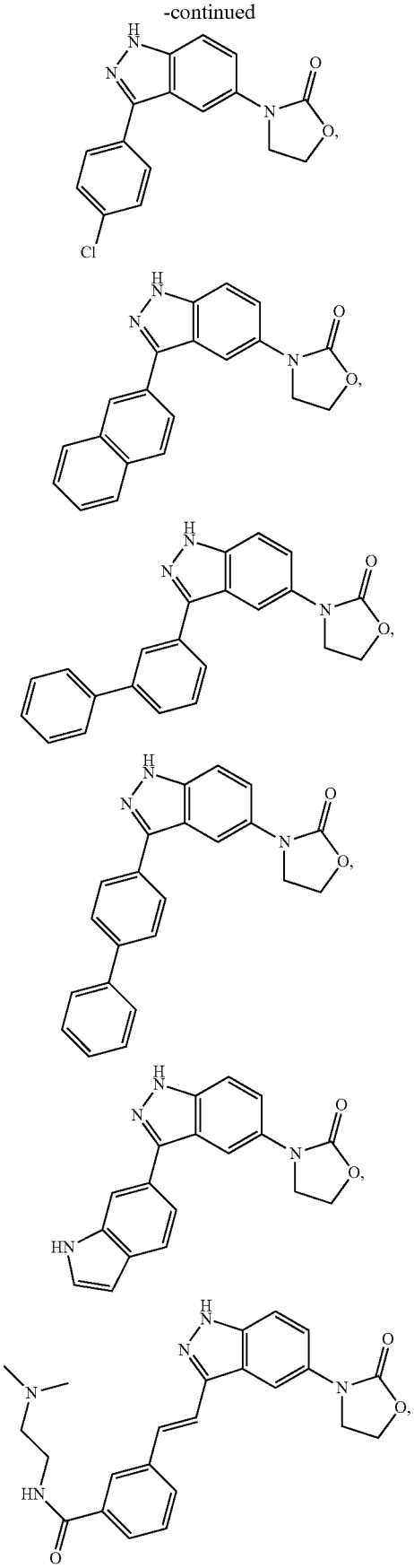
96
-continued
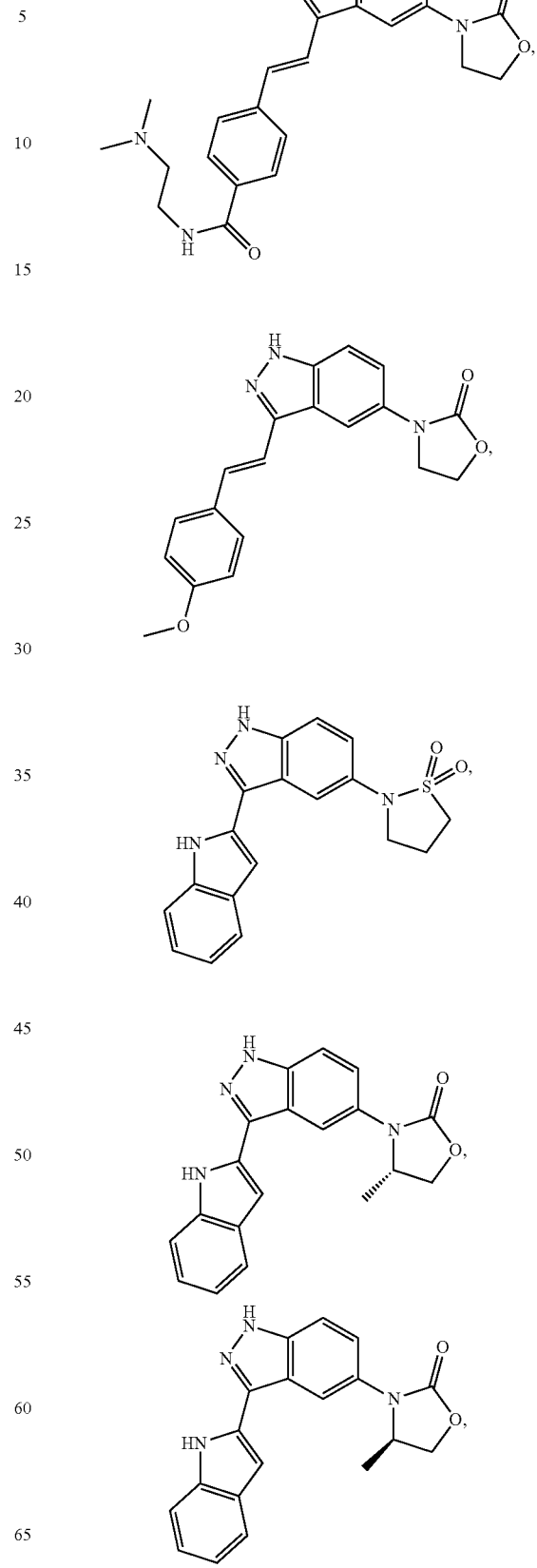

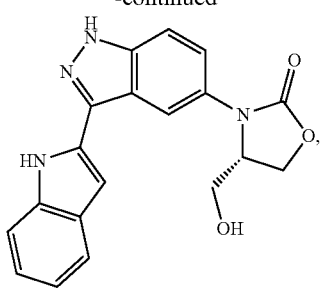
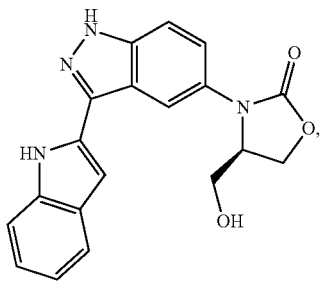
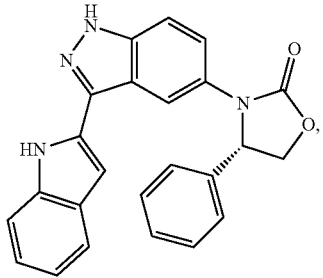
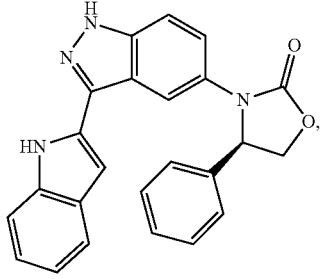
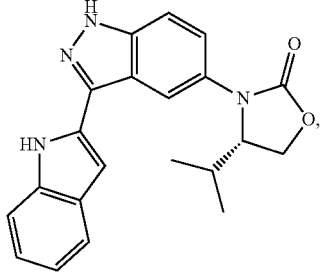
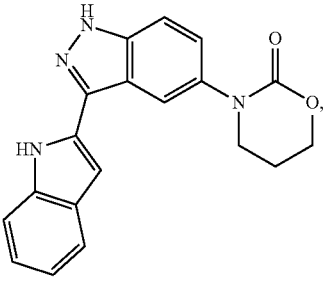
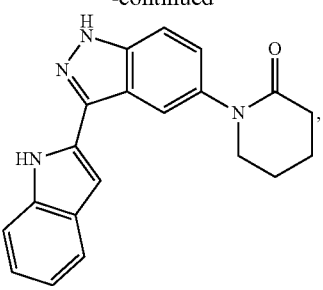
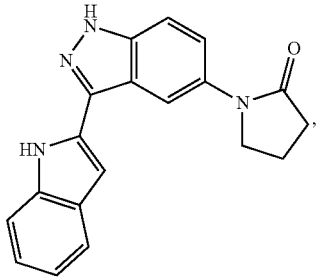
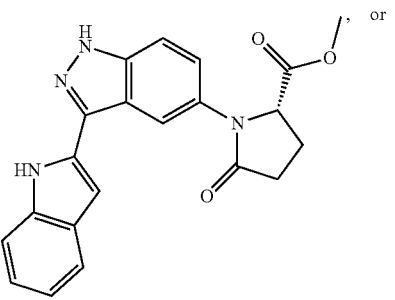
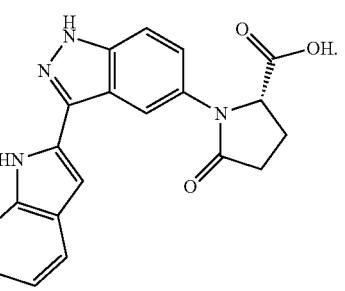
6. The compound of claim 3, wherein the compound has the following structure:
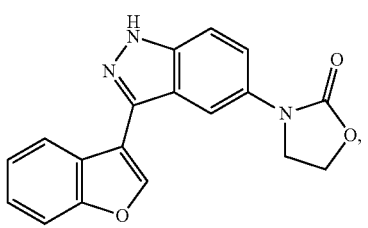

99
-continued
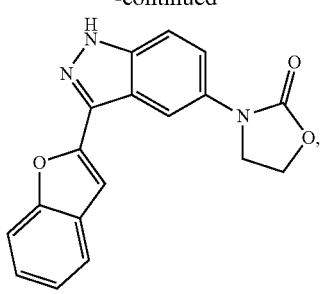
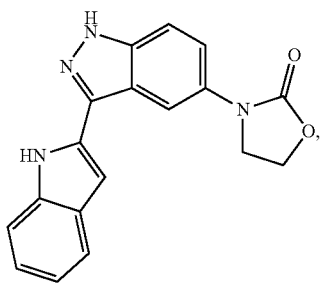
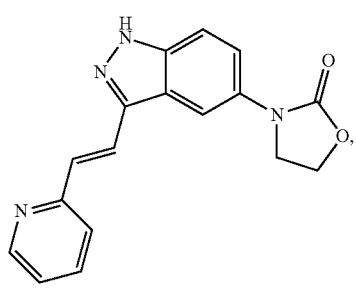
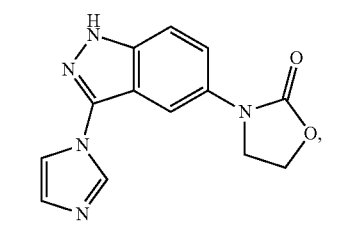
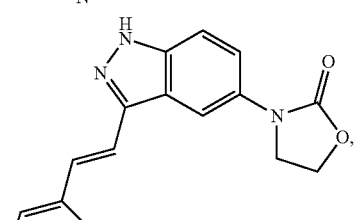
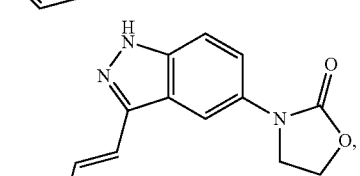
100
-continued
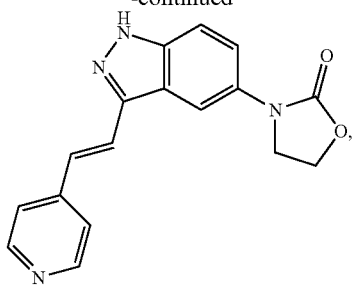
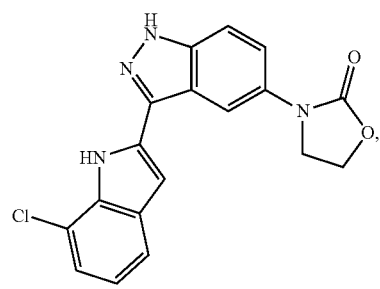
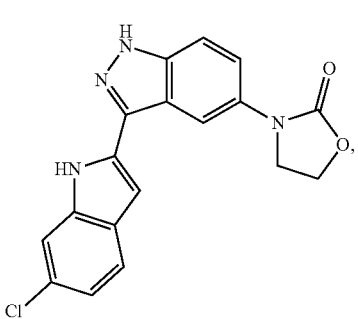
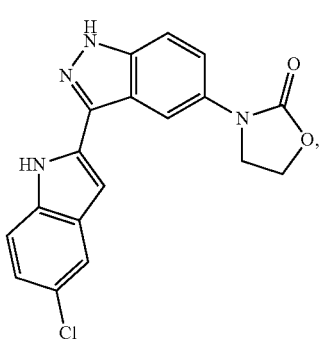
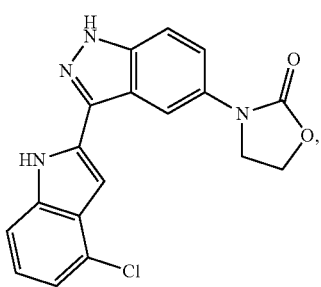

101
-continued
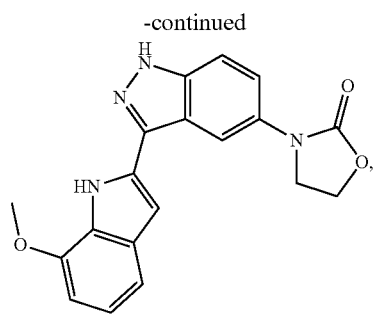
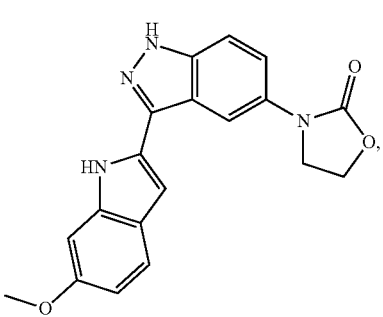
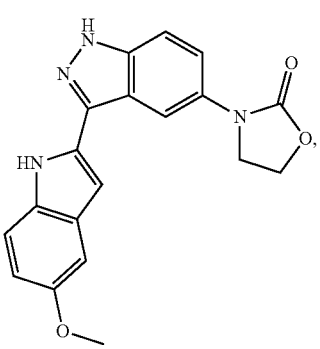
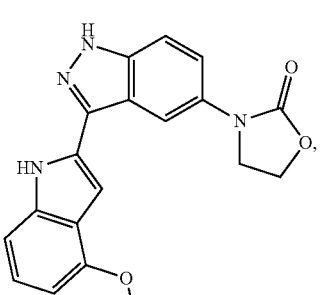
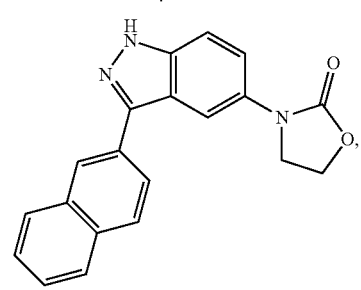
102
-continued
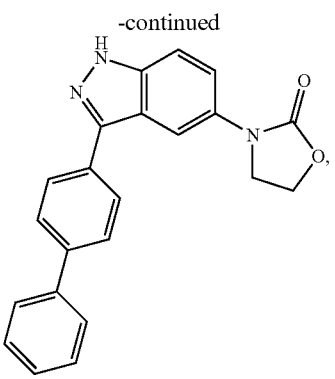
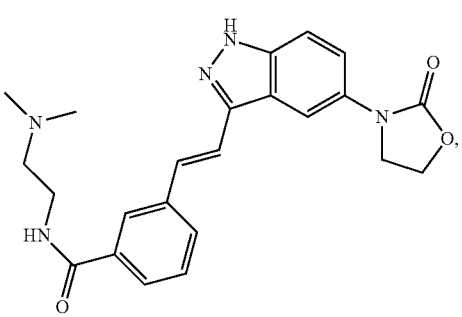
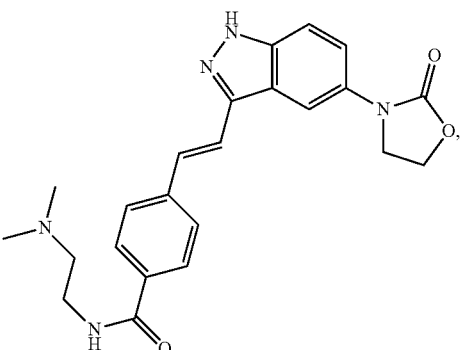
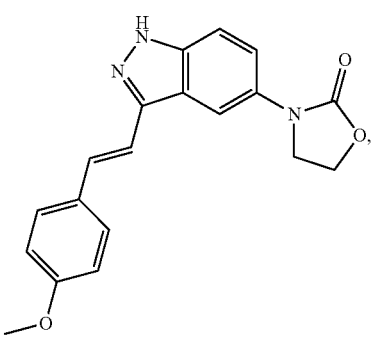
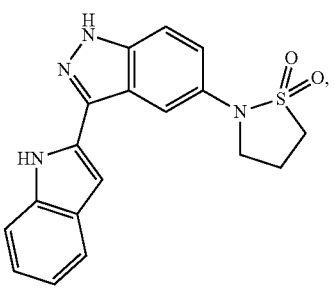

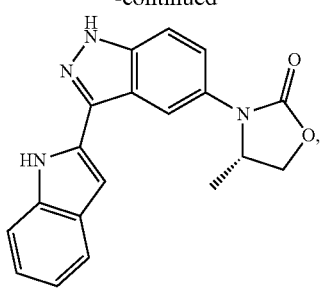
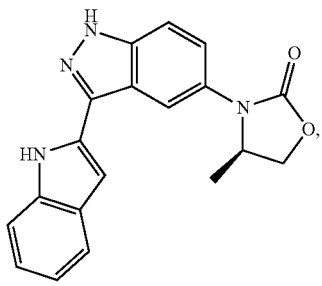
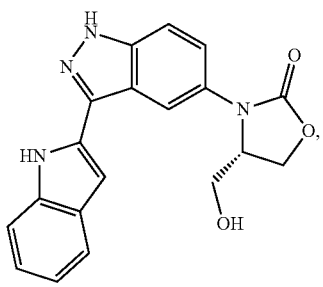
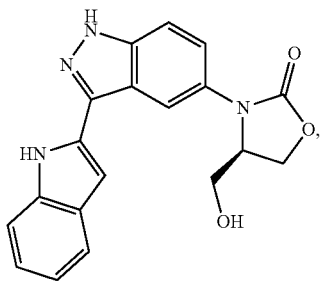
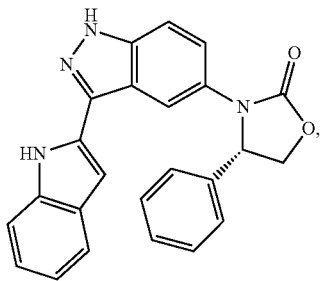
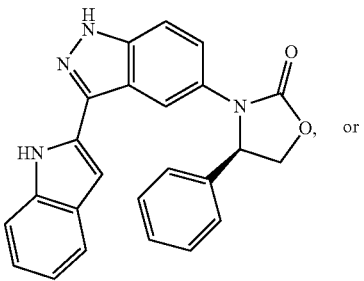
or
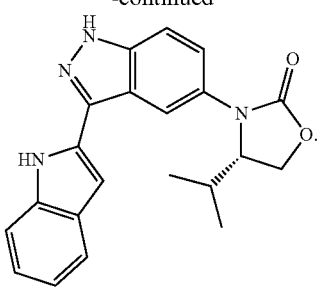
7. A compound of claim 1, wherein the compound has the following structure:
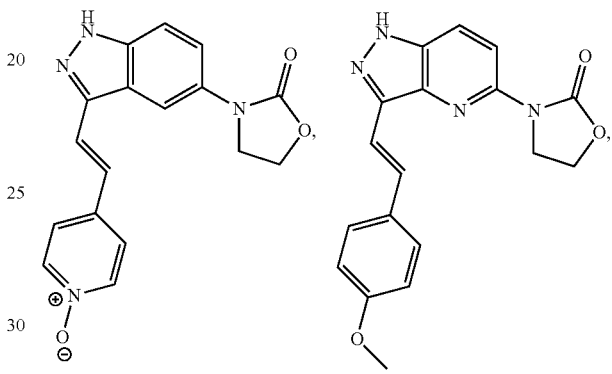
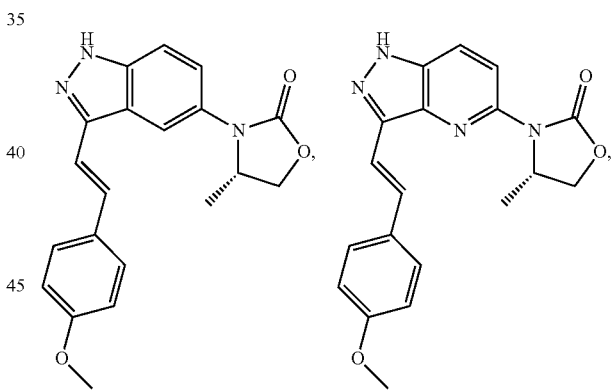
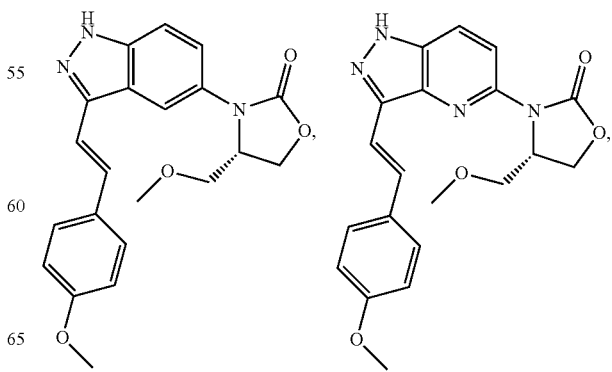

105
-continued
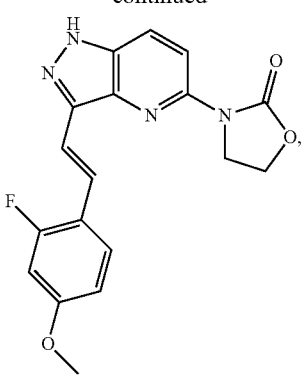
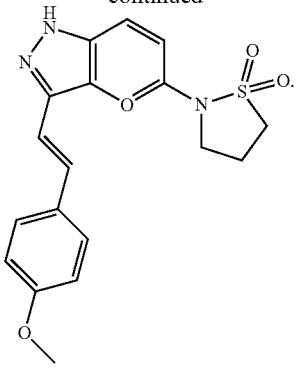
106
-continued
8. A composition comprising one or more compound of claim 1 and one or more pharmaceutically acceptable carrier.
9. The compound of claim 5, wherein the compound has the following structure:
* * * * *